United States Patent
Kawase

(10) Patent No.: US 6,326,503 B1
(45) Date of Patent: Dec. 4, 2001

(54) 16-ENE-VITAMIN D DERIVATIVES

(75) Inventor: Akira Kawase, Shizuoka-ken (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/640,800

(22) Filed: Aug. 18, 2000

Related U.S. Application Data (6262) Division of application No. 09/319,583, filed as application No. PCT/JP97/04715 on Dec. 19, 1997.

(30) Foreign Application Priority Data

Dec. 20, 1996 (JP) ..................................... 8-341786

(51) Int. Cl.$^7$ ................. C07J 31/00; C07J 1/00
(52) U.S. Cl. .................. 552/623; 552/523; 552/623; 552/632
(58) Field of Search ................. 552/523, 623, 552/632

(56) References Cited

U.S. PATENT DOCUMENTS 5,824,811 * 10/1998 Kubodera et al. ............... 552/653
5,827,883 * 10/1998 Barbier et al. ................... 514/546

FOREIGN PATENT DOCUMENTS

9414766 * 7/1994 (WO).

OTHER PUBLICATIONS

Baelen et al., "Activity of Vitamin D Analogs in Co-Transpected COS-7 Cells", *Proc. Workshop Vitam. D* pp. 77–78, (1994); (CA 123:160074).*

Skowronski et al., "Actions of Vitamin D Analogs on Human Prostate Cancer Cells Lines: Comparison with 1,25-Dihydroxyvitamin D", *Endocrinology*, vol. 138, No. 1, pp. 20–26, (1995).*

Jung et al., "1,25(OH)-16ENE-Vitamin D, is a Potent Antileukemic Agent with Low Potential to Cause Hypercalcemia", *LEUK. Res.*, vol. 18, No.6, pp. 453–463, (1994).*

Kubodera et al., "Synthetic Studies of Vitamin D Analogues, XI. Synthesis and Differentiation–Inducing Activity of 1,25–Dihydroxy–22oxavitamin D Analogues", *Chem. Pharm. Bull.*, vol. 40, No.6, pp. 1494–1499, (1992).*

Kawase et al., "Synthesis of 1 25–Dihydroxy–22–Thiavitamin D and Related Analogs", *Bioorganic & Medicinal Chemisrty Letters*, vol. 5, No.3, pp. 279–282, (1995).*

Patent Abstract of Japan, JP–06256300A, (1994), vol. 18, No. 656 (C–1286).*

Patent Absrtact of Japan, JP–06080626A, (1994), vol. 18, No. 337 (C–1217).*

Chemical Abstracts, XP–002115779, vol.115, No.3, (1991) (CA 115:28077X).*

Chemical Abstracts, XP–002115778, vol.122, NO.23, (1995)(CA 122:282993W).*

Norman et al. (Ca 130:282223, Abstract of WO 99164552).*

* cited by examiner

*Primary Examiner*—Sabiha Qazi
(74) *Attorney, Agent, or Firm*—Browdy and Neimark

(57) ABSTRACT

A compound having the formula (4): wherein

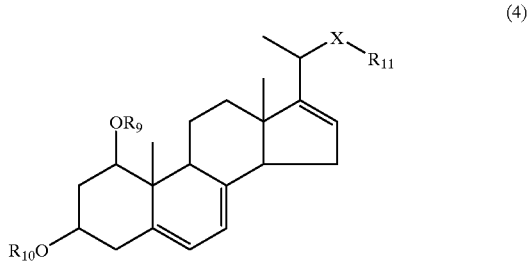

(4)

X is oxygen or sulfur, $R_9$ and $R_{10}$ are each a hydrogen or a protecting group, and $R_{11}$ is an aliphatic hydrocarbon, a —$COR_{12}$ group where $R_{12}$ is alkyl, aryl or alkoxy, or a group of formula

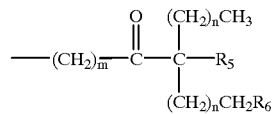

wherein $R_5$ and $R_6$ are each hydrogen or hydroxyl, m is 1 to 4, and n is 0–2.

5 Claims, 6 Drawing Sheets

16-ENE-VITAMIN D DERIVATIVES

This is a division of copending parent application Ser. No. 09/319,583, Jun. 9, 1999, the international application of which was filed Dec. 19, 1997 as a 371 of PCT/JP97/04715.

TECHNICAL FIELD

The present invention relates to novel vitamin D derivatives with high binding ability to vitamin D receptors and weak hypercalcemic activity, useful compounds as pharmaceutical agents such as antitumor agents, antirheumatic agents, etc., and novel synthetic intermediates which are useful for synthesis of said compounds.

BACKGROUND ART

Activated vitamins $D_3$ including 1α, 25-dihydroxy-vitamin $D_3$ are known to have many physiological activities such as calcium catabolism regulation, growth inhibition and differentiation induction of tumor cells, immunoregulation. However, some activated vitamins $D_3$ disadvantageously cause hypercalcemia during long-term and continuous administration so that they are not suitable for use as antitumor agents, antirheumatic agents or the like. Thus, a number of vitamin D derivatives have been synthesized and examined for the purpose of separating activities of these vitamins D.

For example, JPA No. 267550/86 discloses 1α,3β-dihydroxy-20(S)-(3-hydroxy-3-methylbutyloxy)-9,10-secopregna-5,7,10(19)-triene and JPA No. 330714/95 discloses a vitamin D derivative substituted by a sulfur atom at the 22-position.

Various vitamin D derivatives having a double bond at the 16-position are described in JPA No. 9861/90, JPA No. 17019/91, JPA No. 188159/95, JPA No. 40975/94, JPA No. 179418/95, U.S. Pat. No. 5,087,619 and U.S. Pat. No. 5,145,846, etc. However, none of these compounds are said to have weak hypercalcemic activity.

Many of these known vitamin D compounds have high binding ability to vitamin D receptors but strong hypercalcemic activity, or weak hypercalcemic activity but unsatisfactory binding ability to vitamin D receptors. Therefore, it would be desirable to develop promising compounds with high binding ability to vitamin D receptors and weak hypercalcemic activity.

DISCLOSURE OF INVENTION

As a result of careful studies of compounds with high binding ability to vitamin D receptors and weak hypercalcemic activity in view of the above problems, we found that compounds of general formula (1):

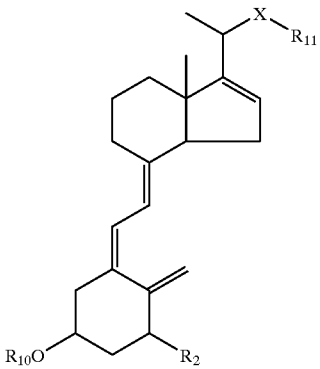

(1)

wherein X represents an oxygen or sulfur atom, $R_{11}$ represents a saturated or unsaturated aliphatic hydrocarbon group which may be substituted by a hydroxyl group or a protected hydroxyl group, or a —$COR_{12}$ group where $R_{12}$ represents an alkyl, aryl or alkoxy group, $R_2$ represents —$OR_9$ or a hydrogen atom, and $R_9$ and $R_{10}$ may be the same or different and each represent a hydrogen atom or a protecting group, have high binding ability to vitamin D receptors and weak hypercalcemic activity, and thus accomplished the present invention.

According to one aspect of the present invention, vitamin D derivatives of general formula (1):

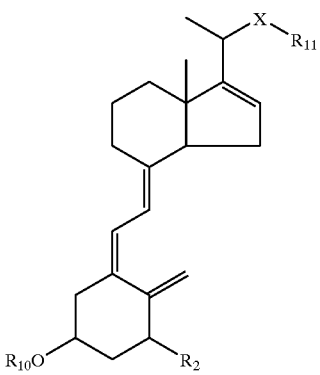

(1)

wherein X represents an oxygen or sulfur atom, $R_{11}$ represents a saturated or unsaturated aliphatic hydrocarbon group which may be substituted by a hydroxyl group or a protected hydroxyl group, or a —$COR_{12}$ group where $R_{12}$ represents an alkyl, aryl or alkoxy group, $R_2$ represents —$OR_9$ or a hydrogen atom, and $R_9$ and $R_{10}$ may be the same or different and each represent a hydrogen atom or a protecting group are provided.

In general formula (1), $R_2$ is preferably —$OR_9$.

In general formula (1), $R_{11}$ is preferably a saturated C1–C15 aliphatic hydrocarbon group which may be substituted by a hydroxyl group.

In general formula (1), $R_{11}$ is preferably an unsaturated C2–C15 aliphatic hydrocarbon group which may be substituted by a hydroxyl group.

In general formula (1), $R_{11}$ is preferably a group (2):

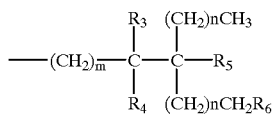

(2)

wherein $R_3$ and $R_4$ may be the same or different and each represent a hydrogen atom or a hydroxyl group, or are combined to represent =O, provided that $R_3$ and $R_4$ can not be a hydroxyl groups simultaneously, $R_5$ and $R_6$ each represent a hydrogen atom or a hydroxyl group, but $R_6$ can not be a hydroxyl group simultaneously with $R_3$ or $R_4$, m represents an integer of 1 to 4, and n represents an integer of 0 to 2; or a group (3):

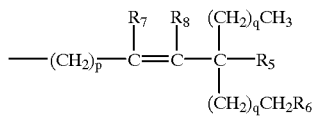

(3)

wherein $R_5$ and $R_6$ may be the same or different and each represent a hydrogen atom or a hydroxyl group, $R_7$ and $R_8$ each represent a hydrogen atom or are combined to represent a covalent bond, p represents an integer of 1 to 3, and q represents an integer of 0 to 2.

In general formula (1), $R_{11}$ is especially preferably a 3-hyroxy-3-methylbutyl group.

In an embodiment of compounds represented by general formula (1), the 20-position is in S-configuration.

In another embodiment of compounds represented by general formula (1), the 20-position is in R-configuration.

Specific examples of compounds represented by general formula (1) include 1,3-dihydroxy-20-(3-hydroxy-3-methylbutylthio)-9,10-secopregna-5,7,10(19),16-tetraene. Sterically defined examples of this compound include 1α,3β-dihydroxy-20(S)-(3-hydroxy-3-methylbutylthio)-9,10-secopregna-5,7,10(19),16-tetraene and 1α,3β-dihydroxy-20(R)-(3-hydroxy-3-methylbutylthio)-9,10-secopregna-5,7,10(19),16-tetraene.

Other specific examples of compounds represented by general formula (1) include 1α,3β-dihydroxy-20(R)-((E)-4-hydroxy-4-methyl-2-pentenylthio)-9,10-secopregna-5,7,10(19),16-tetraene and 1α,3β-dihydroxy-20(R)-((E)-4-ethyl-4-hydroxy-2-hexenylthio)-9,10-secopregna-5,7,10(19),16-tetraene.

Other specific examples of compounds represented by general formula (1) include 1α,3β-dihydroxy-20(S)-(2-hydroxy-2-methylpropylthio)-9,10-secopregna-5,7,10(19),16-tetraene; 1α,3β-dihydroxy-20(R)-(2-hydroxy-2-methylpropyl-thio)-9,10-secopregna-5,7,10(19),16-tetraene; 1α,3β-dihydroxy-20(S)-{2(S)-hydroxy-3-methylbutyloxy}-9,10-secopregna-5,7,10(19),16-tetraene; 1α,3β-dihydroxy-20(S)-{2(R)-hydroxy-3-methylbutyloxy}-9,10-secopregna-5,7,10(19),16-tetraene; 1α,3β-dihydroxy-20(S)-(2-ethyl-2-hydroxybutylthio)-9,10-secopregna-5,7,10(19),16-tetraene; and 1α,3β-dihydroxy-20(R)-(2-ethyl-2-hydroxybutylthio)-9,10-secopregna-5,7,10(19),16-tetraene.

According to another aspect of the present invention, compounds of general formula (4):

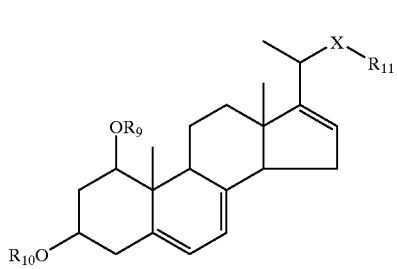

(4)

wherein X represents an oxygen or sulfur atom, $R_{11}$ represents a saturated or unsaturated aliphatic hydrocarbon group which may be substituted by a hydroxyl group or a protected hydroxyl group, or a —$COR_{12}$ group where $R_{12}$ represents an alkyl, aryl or alkoxy group, and $R_9$ and $R_{10}$ may be the same or different and each represent a hydrogen atom or a protecting group are provided.

In general formula (4), $R_{11}$ is preferably a saturated C1–C15 aliphatic hydrocarbon group which may be substituted by a hydroxyl group.

In general formula (4), $R_{11}$ is preferably an unsaturated C2–C15 aliphatic hydrocarbon group which may be substituted by a hydroxyl group.

In general formula (4), $R_{11}$ is preferably a group (2):

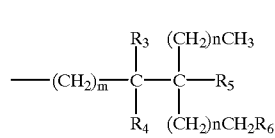

(2)

wherein $R_3$ and $R_4$ may be the same or different and each represent a hydrogen atom or a hydroxyl group, or are combined to represent =O, provided that $R_3$ and $R_4$ can not be a hydroxyl group simultaneously, $R_5$ and $R_6$ each represent a hydrogen atom or a hydroxyl group, but $R_6$ can not be a hydroxyl group simultaneously with $R_3$ or $R_4$, m represents an integer of 1 to 4, and n represents an integer of 0 to 2; or a group (3):

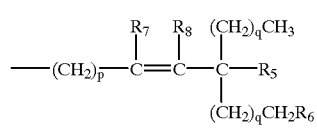

(3)

wherein $R_5$ and $R_6$ may be the same or different and each represent a hydrogen atom or a hydroxyl group, $R_7$ and $R_8$ each represent a hydrogen atom or are combined to represent a covalent bond, p represents an integer of 1 to 3, and q represents an integer of 0 to 2.

In general formula (4), $R_{11}$ is especially preferably a 3-hyroxy-3-methylbutyl group.

According to another aspect of the present invention, compounds of general formula (24):

(24)

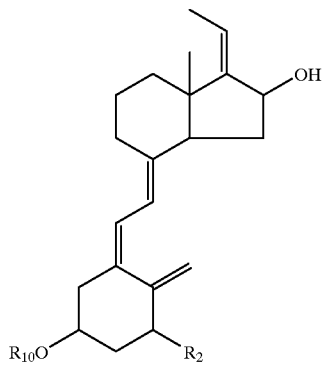

wherein $R_9$ and $R_{10}$ may be the same or different and each represent a hydrogen atom or a protecting group are provided.

According to still another aspect of the present invention, compounds of general formula (5):

(5)

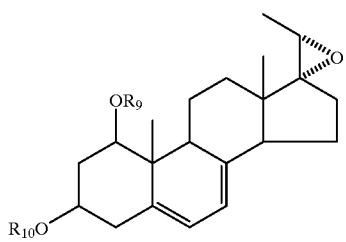

wherein $R_9$ and $R_{10}$ may be the same or different and each represent a hydrogen atom or a protecting group, and the conjugated double bond in the formula may be protected by a protecting group are provided.

According to still another aspect of the present invention, compounds of general formula (6):

(6)

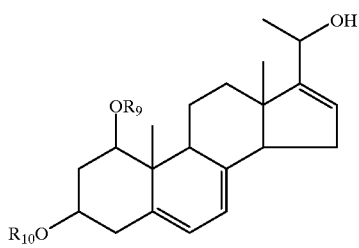

wherein $R_9$ and $R_{10}$ may be the same or different and each represent a hydrogen atom or a protecting group are provided.

According to still another aspect of the present invention, compounds of general formula (7):

(7)

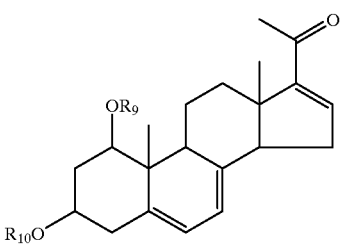

wherein $R_9$ and $R_{10}$ may be the same or different and each represent a hydrogen atom or a protecting group are provided.

According to still another aspect of the present invention, a process for preparing a vitamin D derivative of general formula (1):

(1)

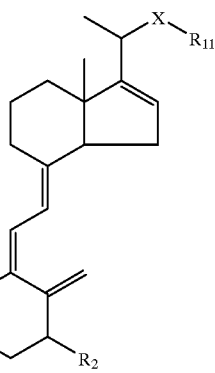

wherein X represents an oxygen or sulfur atom, $R_{11}$ represents a saturated or unsaturated aliphatic hydrocarbon group which may be substituted by a hydroxyl group or a protected hydroxyl group, or a —$COR_{12}$ group where $R_{12}$ represents an alkyl, aryl or alkoxy group, $R_2$ represents —$OR_9$ or a hydrogen atom, and $R_9$ and $R_{10}$ may be the same or different and each represent a hydrogen atom or a hydroxyl group is provided, which process comprises subjecting a compound of general formula (4a):

(4a)

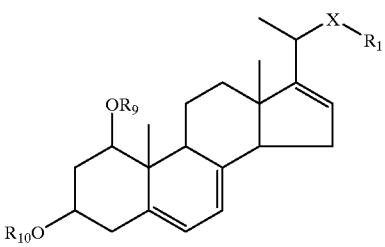

wherein X represents an oxygen or sulfur atom, $R_1$ represents a saturated or unsaturated aliphatic hydrocarbon group which may be substituted by a hydroxyl group or a protected hydroxyl group, or a —$COR_{12}$ group where $R_{12}$ represents an alkyl, aryl or alkoxy group, and $R_9$ and $R_{10}$ may be the same or different and each represent a hydrogen atom or a protecting group, to photoreaction, thermal isomerization and deprotection.

According to still another aspect of the present invention, pharmaceutical agents comprising a vitamin D derivative of general formula (1) are provided.

THE MOST PREFERRED EMBODIMENTS OF INVENTION

Figure 1:
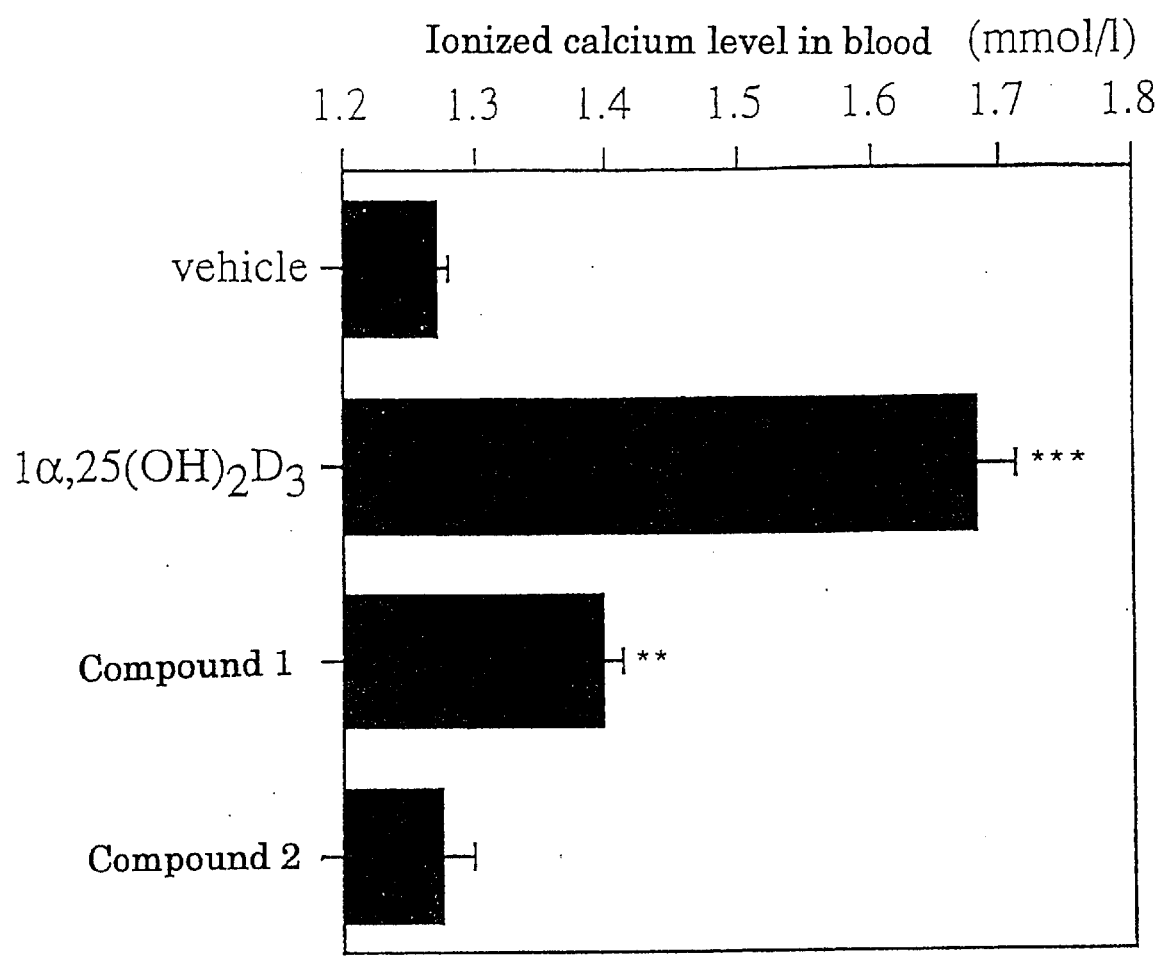
FIG. 1 is a graph showing assay results of the ionized calcium level in blood after administration of an activated vitamin $D_3$ or vitamin $D_3$ derivatives.

Terms as used herein have the following meanings unless otherwise specified.

The saturated aliphatic hydrocarbon group generally means a straight or branched alkyl group containing 1 to 15 carbon atoms, such as methyl, ethyl, n-propyl, i-propyl, n-butyl, s-butyl, i-butyl and t-butyl groups as well as pentyl, hexyl, heptyl, octyl, nonyl and decanyl groups, preferably 3-methylbutyl, 3-ethylpentyl, 4-methylpentyl, 3-(n-propyl) hexyl, 4-ethylhexyl, 5-methylhexyl, 6-methylheptyl, 5-ethylheptyl and 4-(n-propyl)heptyl groups or the like, more preferably 3-methylbutyl, 3-ethylpentyl and 4-methylpentyl groups or the like.

The unsaturated aliphatic hydrocarbon group generally means a straight or branched alkenyl or alkynyl group containing 2 to 15 carbon atoms, such as 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, 2-propynyl, 2-butynyl, 3-butynyl, 2-pentynyl, 3-pentynyl, 4-pentynyl, 2-hexynyl, 3-hexynyl, 4-hexynyl, 5-hexynyl, 2-heptynyl, 3-heptynyl, 4-heptynyl, 5-heptynyl and 6-heptynyl groups, in which any hydrogen atom may be substituted by one or more alkyl groups as mentioned above, and the double bond may be in either cis- or trans-configuration. Preferred are 4-methyl-2-pentynyl, 4-ethyl-2-hexynyl, 4-methyl-2-pentenyl and 4-ethyl-2-hexenyl groups or the like.

The saturated or unsaturated aliphatic hydrocarbon group which may be substituted by a hydroxyl group means said saturated or unsaturated hydrocarbon group in which any hydrogen atom may be substituted by one or more hydroxyl groups such as 0, 1, 2, 3 hydroxyl groups, preferably 1 or 2 hydroxyl groups, more preferably one hydroxyl group. Specific examples other than the aliphatic hydrocarbon groups as mentioned above include saturated aliphatic hydrocarbon groups such as 2-hydroxy-2-methylpropyl, 3-hydroxy-2-methylpropyl, 2,3-dihydroxy-2-methylpropyl, 2-ethyl-2-hydroxybutyl, 2-ethyl-3-hydroxybutyl, 2-ethyl-2,3-dihydroxybutyl, 2-hydroxy-2-(n-propyl)pentyl, 3-hydroxy-2-(n-propyl)pentyl, 2,3-dihydroxy-2-(n-propyl)pentyl, 2-hydroxy-3-methylbutyl, 3-hydroxy-3-methylbutyl, 4-hydroxy-3-methylbutyl, 2,3-dihydroxy-3-methylbutyl, 2,4-dihydroxy-3-methylbutyl, 3,4-dihydroxy-3-methylbutyl, 3-ethyl-2-hydroxypentyl, 3-ethyl-3-hydroxypentyl, 3-ethyl-4-hydroxypentyl, 3-ethyl-2,3-dihydroxypentyl, 3-ethyl-2,4-dihydroxypentyl, 3-ethyl-3,4-dihydroxypentyl, 2-hydroxy-3-(n-propyl)hexyl, 3-hydoxy-3-(n-propyl)hexyl, 4-hydroxy-3-(n-propyl)hexyl, 2,3-dihydroxy-3-(n-propyl)hexyl, 2,4-dihydroxy-3-(n-propyl) hexyl, 3,4-dihydroxy-3-(n-propyl)hexyl, 3-hydroxy-4-methylpentyl, 4-hydroxy-4-methylpentyl, 5-hydroxy-4-methylpentyl, 3,4-dihydroxy-4-methylpentyl, 3,5-dihydroxy-4-methylpentyl, 4,5-dihydroxy-4-methylpentyl, 4-ethyl-3-hydroxyhexyl, 4-ethyl-4-hydroxyhexyl, 4-ethyl-5-hydroxyhexyl, 4-ethyl-3,4-dihydroxyhexyl, 4-ethyl-3,5-dihydroxyhexyl, 4-ethyl-4,5-dihydroxyhexyl, 3-hydroxy-4-(n-propyl)heptyl, 4-hydroxy-4-(n-propyl)heptyl, 5-hydroxy-4-(n-propyl)heptyl, 3,4-dihydroxy-4-(n-propyl)heptyl, 3,5-dihydroxy-4-(n-propyl)heptyl, 4,5-dihydroxy-4-(n-propyl)heptyl, 4-hydroxy-5-methylhexyl, 5-hydroxy-5-methylhexyl, 6-hydroxy-5-methylhexyl, 4,5-dihydroxy-5-methylhexyl, 4,6-dihydroxy-5-methylhexyl, 5,6-dihydroxy-5-methylhexyl, 5-ethyl-4-hydroxyheptyl, 5-ethyl-5-hydroxyheptyl, 5-ethyl-6-hydroxyheptyl, 5-ethyl-4,5-dihydroxyheptyl, 5-ethyl-4,6-dihydroxyheptyl, 5-ethyl-5,6-dihydroxyheptyl, 4-hydroxy-5-(n-propyl)octyl, 5-hydroxy-5-(n-propyl)octyl, 6-hydroxy-5-(n-propyl)octyl, 4,5-dihydroxy-5-(n-propyl)octyl, 4,6-dihydroxy-5-(n-propyl) octyl, 5,6-dihydroxy-5-(n-propyl)octyl, 5-hydroxy-6-methylheptyl, 6-hydroxy-6-methylheptyl, 7-hydroxy-6-methylheptyl, 5,6-dihydroxy-6-methylheptyl, 5,7-dihydroxy-6-methylheptyl, 6,7-dihydroxy-6-methylheptyl, 6-ethyl-5-hydroxyoctyl, 6-ethyl-6-hydroxyoctyl, 6-ethyl-7-hydroxyoctyl, 6-ethyl-5,6-dihydroxyoctyl, 6-ethyl-5,7-dihydroxyoctyl, 6-ethyl-6,7-hydroxyoctyl, 5-hydroxy-6-(n-propyl)nonyl, 6-hydroxy-6-(n-propyl)nonyl, 7-hydroxy-6-(n-propyl)nonyl, 5,6-dihydroxy-6-(n-propyl)nonyl, 5,7-dihydroxy-6-(n-propyl)nonyl, 6,7-dihydroxy-6-(n-propyl) nonyl groups; and 4-hydroxy-4-methyl-2-pentenyl, 5-hydroxy-4-methyl-2-pentenyl, 4,5-dihydroxy-4-methyl-2-pentenyl, 4-ethyl-4-hydroxy-2-hexenyl, 4-ethyl-5-hydroxy-2-hexenyl, 4-ethyl-4,5-dihydroxy-2-hexenyl, 4-hydroxy-4-(n-propyl)-2-heptenyl, 5-hydroxy-4-(n-propyl)-2-heptenyl, 4,5-dihydroxy-4-(n-propyl)-2-heptenyl, 5-hydroxy-5-methyl-3-hexenyl, 6-hydroxy-5-methyl-3-hexenyl, 5,6-dihydroxy-5-methyl-3-hexenyl, 5-ethyl-5-hydroxy-3-heptenyl, 5-ethyl-6-hydroxy-3-heptenyl, 5-ethyl-5,6-dihydroxy- 3-heptenyl, 5-hydroxy-5-(n-propyl)-3-octenyl, 6-hydroxy-5-(n-propyl)-3-octenyl, 5,6-dihydroxy-5-(n-propyl)-3-octenyl, 4-hydroxy-5-methyl-2-hexenyl, 5-hydroxy-5-methyl-2-hexenyl, 6-hydroxy-5-methyl-2-hexenyl, 4,5-dihydroxy-5-methyl-2-hexenyl, 4,6-dihydroxy-5-methyl-2-hexenyl, 5,6-dihydroxy-5-methyl-2-hexenyl, 5-ethyl-4-hydroxy-2-heptenyl, 5-ethyl-5-hydroxy-2-heptenyl, 5-ethyl-6-hydroxy-2-heptenyl, 5-ethyl-4,5-dihydroxy-2-heptenyl, 5-ethyl-4,6-dihydroxy-2-heptenyl, 5-ethyl-5,6-dihydroxy-2-heptenyl, 4-hydroxy-5-(n-propyl)-2-octenyl, 5-hydroxy-5-(n-propyl)-2-octenyl, 6-hydroxy-5-(n-propyl)-2-octenyl, 4,5-dihydroxy-5-(n-propyl)-2-octenyl, 4,6-dihydroxy-5-(n-propyl)-2-octenyl, 5,6-dihydroxy-5-(n-propyl)-2-octenyl, 6-hydroxy-6-methyl-4-heptenyl, 7-hydroxy-6-methyl-4-heptenyl, 6,7-dihydroxy-6-methyl-4-heptenyl, 6-15 ethyl-6-hydroxy-4-octenyl, 6-ethyl-7- hydroxy-4-octenyl, 6-ethyl-6,7-dihydroxy-4-octenyl, 6-hydroxy-6-(n-propyl)-4-nonenyl, 7-hydroxy-6-(n-propyl)-4-nonenyl, 6,7-dihydroxy-6-(n-propyl)-4-nonenyl, 5-hydroxy-6-methyl-3-heptenyl, 6-hydroxy-6-methyl-3-heptenyl, 7-hydroxy-6-methyl-3-heptenyl, 5,6-dihydroxy-6-methyl-3-heptenyl, 5,7-dihydroxy-6-methyl-3-heptenyl, 6,7-dihydroxy-6-methyl-3-heptenyl, 6-ethyl-5-hydroxy-3-octenyl, 6-ethyl-6-hydroxy-3-octenyl, 6-ethyl-7-hydroxy-3-octenyl, 6-ethyl-5,6-dihydroxy-3-octenyl, 6-ethyl-5,7-dihydroxy-3-octenyl, 6-ethyl-6,7-dihydroxy-3-octenyl, 5-hydroxy-6-(n-propyl)-3-nonenyl, 6-hydroxy-6-(n-propyl)-3-nonenyl, 7-hydroxy-6-(n-propyl)-3-nonenyl, 5,6-dihydroxy-6-(n-propyl)-3-nonenyl, 5,7-dihydroxy-6-(n-propyl)-3-nonenyl, 6,7-dihydroxy-6-(n-propyl)-3-nonenyl, 5-hydroxy-6-methyl-2-heptenyl, 6-hydroxy-6-methyl-2-heptenyl, 7-hydroxy-6-methyl-2-heptenyl, 5,6-dihydroxy-6-methyl-2-heptenyl, 5,7-dihydroxy-6-methyl-2-heptenyl, 6,7-dihydroxy-6-methyl-2-heptenyl, 6-ethyl-5-hydroxy-2-octenyl, 6-ethyl-6-hydroxy-2-octenyl, 6-ethyl-7-hydroxy-2-octenyl, 6-ethyl-5,6-dihydroxy-2-octenyl, 6-ethyl-5,7-dihydroxy-2-octenyl, 6-ethyl-6,7-dihydroxy-2-octenyl, 5-hydroxy-6-(n-propyl)-2-nonenyl, 6-hydroxy-6-(n-propyl)-2-nonenyl, 7-hydroxy-6-(n-propyl)-2-nonenyl, 5,6-dihydroxy-6-(n-propyl)-2-nonenyl, 5,7-dihydroxy-6-(n-propyl)-2-nonenyl, 6,7-dihydroxy-6-(n-propyl)-2-nonenyl, 4-hydroxy-4-methyl-2-pentynyl, 5-hydroxy-4-methyl-2-pentynyl, 4,5-dihydroxy-4-methyl-2-pentynyl, 4-ethyl-4-hydroxy-2-hexynyl, 4-ethyl-5-hydroxy-2-hexynyl, 4-ethyl-4,5-dihydroxy-2-hexynyl, 4-hydroxy-4-(n-propyl)-2-heptynyl, 5-hydroxy-4-(n-propyl)-2-heptynyl, 4,5-dihydroxy-4-(n-propyl)-2-heptynyl, 5-hydroxy-5-methyl-3-hexynyl, 6-hydroxy-5-methyl-3-hexynyl, 5,6-dihydroxy-5-methyl-3-hexynyl, 5-ethyl-5-hydroxy-3-heptynyl, 5-ethyl-6-hydroxy-3-heptynyl, 5-ethyl-5,6-dihydroxy-3-heptynyl, 5-hydroxy-5-(n-propyl)-3-octynyl, 6-hydroxy-5-(n-propyl)-3-octynyl, 5,6-dihydroxy-5-(n-propyl)-3-octynyl, 4-hydroxy-5-methyl-2-hexynyl, 5-hydroxy-5-methyl-2-hexynyl, 6-hydroxy-5-methyl-2-hexynyl, 4,5-dihydroxy-5-methyl-2-hexynyl, 4,6-dihydroxy-5-methyl-2-hexynyl, 5,6-dihydroxy-5-methyl-2-hexynyl, 5-ethyl-4-hydroxy-2-heptynyl, 5-ethyl-5-hydroxy-2-heptynyl, 5-ethyl-6-hydroxy-2-heptynyl, 5-ethyl-4,5-dihydroxy-2-heptynyl, 5-ethyl-4,6-dihydroxy-2-heptynyl, 5-ethyl-5,6-dihydroxy-2-heptynyl, 4-hydroxy-5-(n-propyl)-2-octynyl, 5-hydroxy-5-(n-propyl)-2-octynyl, 6-hydroxy-5-(n-propyl)-2-octynyl, 4,5-dihydroxy-5-(n-propyl)-2-octynyl, 4,6-dihydroxy-5-(n-propyl)-2-octynyl, 5,6-dihydroxy-5-(n-propyl)-2-octynyl, 6-hydroxy-6-methyl-4-heptynyl, 7-hydroxy-6-methyl-4-heptynyl, 6,7-dihydroxy-6-methyl-4-heptynyl, 6-ethyl-6-hydroxy-4-octynyl, 6-ethyl-7-hydroxy-4-octynyl, 6-ethyl-6,7-dihydroxy-4-octynyl, 6-hydroxy-6-(n-propyl)-4-nonynyl, 7-hydroxy-6-(n-propyl)-4-nonynyl, 6,7-dihydroxy-6-(n-propyl)-4-nonynyl, 5-hydroxy-6-methyl-3-heptynyl, 6-hydroxy-6-methyl-3-heptynyl, 7-hydroxy-6-methyl-3-heptynyl, 5,6-dihydroxy-6-methyl-3-a heptynyl, 5,7-dihydroxy-6-methyl-3-heptynyl, 6,7-dihydroxy-6-methyl-3-heptynyl, 6-ethyl-5-hydroxy-3-octynyl, 6-ethyl-6-hydroxy-3-octynyl, 6-ethyl-7-hydroxy-3-octynyl, 6-ethyl-5,6-dihydroxy-3-octynyl, 6-ethyl-5,7-dihydroxy-3-octynyl, 6-ethyl-6,7-dihydroxy-3-octynyl, 5-hydroxy-6-(n-propyl)-3-nonynyl, 6-hydroxy-6-(n-propyl)-3-nonynyl, 7-hydroxy-6-(n-propyl)-3-nonynyl, 5,6-dihydroxy-6-(n-propyl)-3-nonynyl, 5,7-dihydroxy-6-(n-propyl)-3-nonynyl, 6,7-dihydroxy-6-(n-propyl)-3-nonynyl, 5-hydroxy-6-methyl-2-heptynyl, 6-hydroxy-6-methyl-2-heptynyl, 7-hydroxy-6-methyl-2-heptynyl, 5,6-dihydroxy-6-methyl-2-heptynyl, 5,7-dihydroxy-6-methyl-2-heptynyl, 6,7-dihydroxy-6-methyl-2-heptynyl, 6-ethyl-5-hydroxy-2-octynyl, 6-ethyl-6-hydroxy-2-octynyl, 6-ethyl-7-hydroxy-2-octynyl, 6-ethyl-5,6-dihydroxy-2-octynyl, 6-ethyl-5,7-dihydroxy-2-octynyl, 6-ethyl-6,7-dihydroxy-2-octynyl, 5-hydroxy-6-(n-propyl)-2-nonynyl, 6-hydroxy-6-(n-propyl)-2-nonynyl, 7-hydroxy-6-(n-propyl)-2-nonynyl, 5,6-dihydroxy-6-(n-propyl)-2-nonynyl, 5,7-dihydroxy-6-(n-propyl)-2-nonynyl, 6,7-dihydroxy-6-(n-propyl)-2-nonynyl groups or the like, preferably 3-hydroxy-3-methylbutyl, 4-hydroxy-3-methylbutyl, 3,4-dihydroxy-3-methylbutyl, 3-ethyl-3-hydroxypentyl, 3-ethyl-4-hydroxypentyl, 3-ethyl-3,4-dihydroxypentyl, 4-hydroxy-4-methylpentyl, 5-hydroxy-4-methylpentyl, 4,5-dihydroxy-4-methylpentyl, 4-ethyl-4-hydroxyhexyl, 4-ethyl-5-hydroxyhexyl, 4-ethyl-4,5-dihydroxyhexyl, 4-hydroxy-4-methyl-2-pentenyl, 5-hydroxy-4-methyl-2-pentenyl, 4,5-dihydroxy-4-methyl-2-pentenyl, 4-ethyl-4-hydroxy-2-hexenyl, 4-ethyl-5-hydroxy-2-hexenyl, 4-ethyl-4,5-dihydroxy-2-hexenyl, 4-hydroxy-4-methyl-2-pentynyl, 5-hydroxy-4-methyl-2-pentynyl, 4,5-dihydroxy-4-methyl-2-pentynyl, 4-ethyl-4-hydroxy-2-hexynyl, 4-ethyl-5-hydroxy-2-hexynyl, 4-ethyl-4,5-dihydroxy-2-hexynyl groups or the like.

As used herein, the alkyl group generally means a straight or branched alkyl group containing 1 to 15, preferably 1 to 8 carbon atoms; the aryl group generally means an aryl group containing 6 to 20, preferably 6 to 14 carbon atoms; and the alkoxy group generally means a straight or branched alkoxy group containing 1 to 15, preferably 1 to 8 carbon atoms.

The protecting group includes acyl, substituted silyl and substituted alkyl groups or the like, preferably acyl and substituted silyl groups.

The acyl group means a substituted carbonyl group where the substituent on the carbonyl group includes a hydrogen atom, an optionally substituted lower alkyl group, an optionally substituted aryl group, an optionally substituted lower alkyloxy group, an optionally substituted aryloxy group, an optionally substituted aralkyloxy group or the like. The acyl group preferably includes a formyl group, a lower alkylcarbonyl group, an optionally substituted phenylcarbonyl group, a lower alkyloxycarbonyl group, an optionally substituted phenylalkyloxycarbonyl group or the like, more preferably formyl, acetyl, propionyl, butyryl, pivaloyl, benzoyl, methoxycarbonyl, ethoxycarbonyl, t-butoxycarbonyl, benzyloxycarbonyl groups or the like.

The substituted silyl group means a silyl group substituted by a lower alkyl group which may have one or more substituents or an optionally substituted aryl group or the like, preferably a tri-substituted silyl group. Preferred examples of the substituted silyl group include trimethylsilyl, triethylsilyl, triisopropylsilyl, t-butyldiphenylsilyl, t-butyldimethylsilyl groups or the like.

The substituted alkyl group means an alkyl group substituted by one or more substituents preferably including an optionally substituted alkyloxy group and an optionally substituted aryl group, especially an optionally substituted alkyloxy group. The alkyl group substituted by an optionally substituted alkyloxy group such as an alkyloxy group includes, for example, methoxymethyl, 2-methoxyethoxymethyl and tetrahydropyran-2-yl groups or the like. Examples of the substituent include halogen atoms and cyano, nitro, amino, hydroxyl, alkyl, alkyloxy, acyloxy and sulfonyl groups or the like.

Compounds of general formula (1) of the present invention wherein X is a sulfur atom can be prepared from, for example, a compound of formula (8) described in JPA No.

330714/95 as shown by the following scheme:

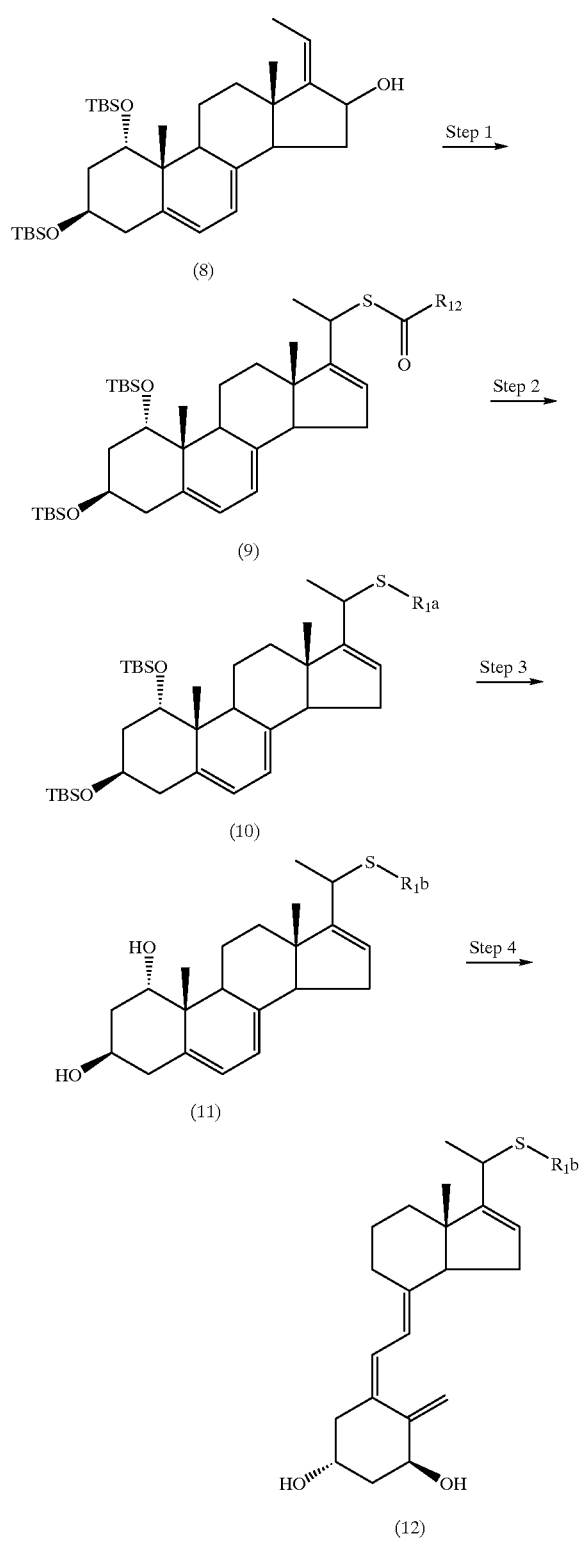

wherein TBS represents a t-butyldimethylsilyl group, $R_{12}$ represents an alkyl, aryl or alkoxy group, $R_{1a}$ represents a saturated or unsaturated aliphatic hydrocarbon group which may be substituted by a hydroxyl group or a protected hydroxyl group, and $R_{1b}$ represents a saturated or unsaturated aliphatic hydrocarbon group substituted by a hydroxyl group.

In the above scheme, the compound of general formula (8) obtained by the same procedure as described in JPA No. 330714/95 may be reacted with an alkyl halothioformate or an aryl halothioformate in an appropriate solvent in the presence of a base to give a compound of general formula (9) through an o-alkyl thiocarbonate or alkyl dithiocarbonate (step 1).

The alkyl halothioformate or aryl halothioformate used in the above step 1 includes, for example, phenyl chlorothionoformate, tolyl chlorothionoformate, 4-tert-butylphenyl chlorothionoformate, 4-fluorophenyl chlorothionoformate, 3-chlorophenyl chlorothionoformate, 4-chlorophenyl chlorothionoformate, 3,4-dichlorophenyl chlorothionoformate, 2,4,6-trichlorophenyl chlorothionoformate, pentafluorophenyl chlorothionoformate, methyl chlorodithioformate, ethyl chlorodithioformate, isopropyl chlorodithioformate, phenyl chlorodithioformate, tolyl chlorodithioformate, 2,4,6-trimethylphenyl chlorodithioformate, 4-fluorophenyl chlorodithioformate, pentafluorophenyl chlorodithioformate, 2-chlorophenyl chlorodithioformate, 3-chlorophenyl chlorodithioformate, 4-chlorophenyl chlorodithioformate, 2,4,5-trichlorophenyl chlorodithioformate, pentachlorophenyl chlorodithioformate, 4-methoxyphenyl chlorodithioformate, 4-cyanophenyl chlorodithioformate, 4-nitrophenyl chlorodithioformate or the like, preferably phenyl chlorothionoformate, tolyl chlorothionoformate, 4-tert-butylphenyl chlorothionoformate, 4-fluorophenyl chlorothionoformate, 4-chlorophenyl chlorothionoformate, 2,4,6-trichlorophenyl chlorothionoformate, pentafluorophenyl chlorothionoformate, phenyl chlorodithioformate or the like, more preferably phenyl chlorothionoformate.

Suitable solvents for use in the above step 1 include hydrocarbon-, ether-, halogen-based solvents or the like, such as benzene, toluene, diethyl ether, tetrahydrofuran, 1,2-dimethoxyethane, dichloromethane, chloroform, carbon tetrachloride, preferably dichloromethane, toluene or the like, more preferably dichloromethane.

Suitable bases for use in the above step 1 include pyridine compounds, amine compounds, imidazole compounds, alkali metal hydroxides, metal hydrides, alkali metal compounds, metal amides or the like, such as pyridine, collidine, lutidine, 2,6-di-tert-butylpyridine, 4-methyl-2,6-di-tert-butylpyridine, 4-dimethylaminopyridine, triethylamine, diisopropylethylamine, imidazole, sodium hydroxide, potassium hydroxide, sodium hydride, potassium hydride, methyl lithium, n-butyl lithium, ethyl magnesium bromide, lithium diisopropylamide, lithium bistrimethylsilylamide, preferably pyridine, collidine, lutidine, 2,6-di-tert-butylpyridine, 4-methyl-2,6-di-tert-butylpyridine, 4-dimethylaminopyridine, triethylamine, diisopropylethylamine, more preferably pyridine.

The reaction temperature of the above step 1 is in the range from 0 to 100° C., preferably room temperature, though it is not specifically limited so far as the reaction proceeds. This reaction allows selective synthesis of thiol carbonates having 20S configuration from 16α-OH isomers and thiol carbonates having 20R configuration from 16β-OH isomers, respectively.

The compound of general formula (9) forms a part of the intermediate of general formula (4).

The compound of general formula (9) may be subjected to alkali solvolysis and S-alkylation to give a compound of general formula (10) in which a side chain has been introduced (step 2).

The base used for the alkali solvolysis and S-alkylation in the above step 2 includes lithium hydroxide, sodium hydroxide, potassium hydroxide, sodium methoxide, potassium tert-butoxide or the like, preferably sodium hydroxide, potassium hydroxide, sodium methoxide or the like. The reaction can be carried out in water or an alcoholic solvent such as methanol, ethanol, propanol, butanol, alone or mixed with an etheric solvent such as diethyl ether, tetrahydrofuran, 1,2-dimethoxyethane, 1,4-dioxane, diglyme, etc.

Suitable alkylating agents include compounds of general formula (13) corresponding to the side chain:

$$Y-R_{1a} \qquad (13)$$

wherein Y represents a halogen atom or a leaving group such as mesyloxy, tosyloxy, trifluoromethanesulfonyloxy, and $R_{1a}$ has the same meaning as above, or epoxides such as isobutyrene oxide, 1,2-epoxy-2-ethylbutane, 1,2-epoxy-3-methylbutane, 1,2-epoxy-3-ethylpentane.

The compound of general formula (10) forms a part of the intermediate of general formula (4).

Suitable compounds of general formula (13) include alkylating agents corresponding to $R_1$ in the compound of general formula (1) of the present invention, such as 4-bromo-2-methyl-2-butanol, 1-bromo-4-methyl-4-triethylsilyloxypentane, 6-bromo-2-methyl-2-hexanol, 5-bromo-3-ethyl-3-pentanol, 6-bromo-3-ethyl-3-hexanol.

The reaction of the above step 2 is carried out at a temperature of −40 to 100° C., preferably 0 to 50° C., more preferably room temperature.

The compound of general formula (10) can be converted into a compound of general formula (11) by a conventional deprotection procedure (step 3).

Suitable reagents for use in the reaction of the above step 3 include hydrochloric acid, acidic ion exchange resin, tetrabutylammonium fluoride, hydrogen fluoride/pyridine, hydrogen fluoride/triethylamine, hydrofluoric acid, preferably tetrabutylammonium fluoride.

Suitable solvents for use in the above step 3 typically include etheric solvents, preferably tetrahydrofuran.

The reaction temperature ranges from room temperature to 65° C., depending on the type of the substrate.

The deprotected compound of general formula (11) also forms a part of the intermediate of general formula (4).

The compound of general formula (11) may be subjected to photoreaction and thermal isomerization to give a compound (12) which corresponds to a compound of general formula (1) of the present invention wherein X represents a sulfur atom and $R_1$ represents a saturated aliphatic hydrocarbon group which may be substituted by a hydroxyl group (step 4). The photoreaction and thermal isomerization here can be carried out by a conventional procedure.

The compound of general formula (9) which has not been deprotected may be subjected to photoreaction and thermal isomerization to give a compound of general formula (1) wherein the hydroxyl group is protected. The order of steps 1, 2, 3 and 4 is not specifically limited, but step 2 can not precede step 1. The process can not be carried out in the order of steps 4→3→1→2. When the side chain has a protecting group, step 3 can be carried out if desired.

Compounds of general formula (1) of the present invention wherein X is an oxygen atom can be obtained from, for example, a known compound (14) described in JPA No. 330714/95 as shown by the following scheme:

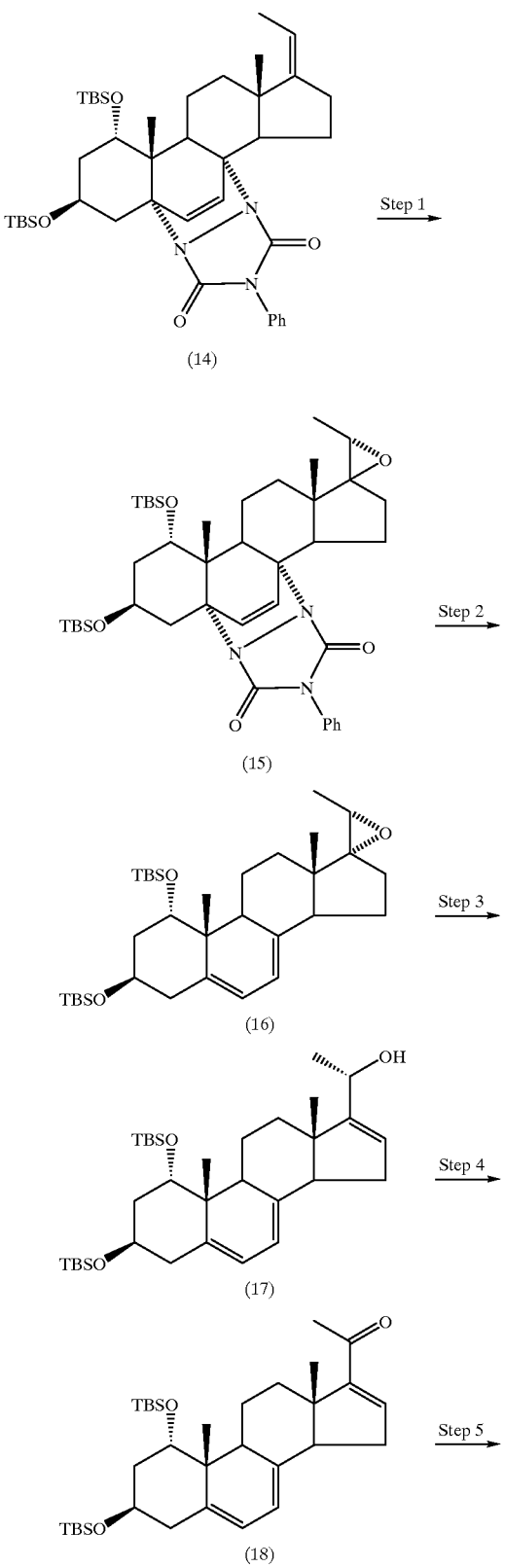

-continued

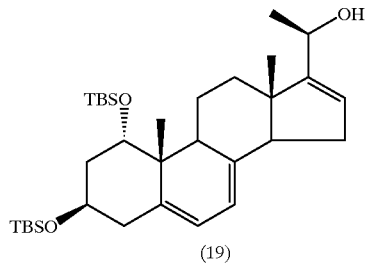

wherein TBS represents a t-butyldimethylsilyl group.

In the above scheme, the compound of formula (14) obtained by the same procedure as described in JPA No. 330714/95 may be oxidized to give a compound of formula (15) (step 1).

Suitable oxidizing agents for use in the above step 1 include m-chloroperbenzoic acid, magnesium monoperoxyphthalate, hydrogen peroxide or the like, preferably m-chloroperbenzoic acid.

Suitable solvents for use in the above step 1 include toluene, benzene, dichloromethane, chloroform, carbon tetrachloride or the like, preferably toluene or dichloromethane. The reaction may be carried out in the presence of a neutralizing agent such as sodium bicarbonate or sodium dihydrogenphosphate in the reaction system.

The reaction temperature of the above step 1 is −78 to 110° C., preferably −40° C. to room temperature.

The compound of formula (15) can be deprotected by a conventional procedure described in, for example, Journal of Organic Chemistry, 57, 5019 (1992), to give a compound of formula (16) (step 2).

The compound of formula (15) or (16) forms a part of the compound of general formula (5).

The step for obtaining a 20S-allylalcohol intermediate of formula (17) from the compound of formula (16) (step 3) may be performed with a simple metal amide such as lithium diethylamide, but preferably with a dialkylaluminium dialkylamide prepared from the corresponding metal amide and dialkylaluminium halide in an inert solvent to give an intended compound at a higher yield in view of the regioselectivity in deprotonation reaction.

Suitable metal amides for use in the above step 3 include lithium diethylamide, lithium diisopropylamide, lithium bistrimethylsilylamide, sodium bistrimethylsilylamide, potassium bistrimethylsilylamide, lithium-2,2,6,6-tetramethylpiperidide or the like, preferably lithium diisopropylamide, lithium bistrimethylsilylamide, more preferably lithium diisopropylamide. Suitable dialkylaluminium halides include dimethylaluminium chloride, diethylaluminium chloride, diisobutylaluminium chloride, diethylaluminium iodide or the like, preferably dimethylaluminium chloride, diethylaluminium chloride, diIsobutylaluminium chloride, more preferably diethylaluminium chloride.

Suitable solvents for use in the above step 3 include hydrocarbon- or halogen-based solvents or the like, such as hexane, benzene, toluene, dichloromethane, chloroform, preferably benzene and toluene. The reaction temperature is −40 to 50° C., preferably 0° C. to room temperature, more preferably 0° C.

The 20S-allylalcohol intermediate of formula (17) may be oxidized to give a compound of formula (18) (step 4), which is further reduced to give a 20R-allylalcohol intermediate of formula (19) (step 5).

The compounds of formulae (17) and (19) form a part of the compound of general formula (6), and the compound of formula (18) forms a part of the compound of general formula (7).

Oxidization conditions in the oxidization reaction of the above step 4 involve using a metal oxidizing agent such as chromium compounds, manganese compounds, osmium compounds, ruthenium compounds; dimethyl sulfoxide; carbonyl compounds (Oppenauer oxidization); quinone compounds, etc. Specific examples include pyridinium chlorochromate, pyridinium dichromate, manganese dioxide, osmium tetraoxide, ruthenium trichloride, tetrapropylammonium perruthenate, oxalyl chloride/dimethyl sulfoxide, triphosgen/dimethyl sulfoxide, sulfur trioxide pyridine complex/dimethyl sulfoxide, acetone/aluminium truisopropoxide, cyclohexanone/aluminium truisopropoxide or the like, preferably pyridinium chlorochromate, pyridinium dichromate, manganese dioxide, tetrapropylammonium perruthenate (catalyst)/4-methyl-morpholine N-oxide, oxalylchloride/dimethyl sulfoxide, etc.

Reduction conditions in the reduction reaction of the above step 5 involve using metal hydrides, metal hydride complex compounds, etc. Specific examples include borane, thexylborane, 9-borabicyclo[3,3,1]nonane, catecholborane, diisobutylaluminium hydride, lithium borohydride, zinc borohydride, sodium borohydride, sodium trimethoxyborohydride, sodium cyanoborohydride, sodium triacetoxyborohydride, lithium tri-s-butylborohydride, potassium tri-s-butylborohydride, lithium trisiamylborohydride, potassium trisiamylborohydride, lithium triethylborohydride, potassium triphenylborohydride, lithium n-butylborohydride, lithium aluminium hydride, lithium trimethoxyaluminohydride, lithium tri-t-butoxyaluminohydride, sodium bis(2-methoxyethoxy)aluminohydride or the like, preferably diisobutylaluminium hydride, sodium borohydride/cerium chloride, lithium n-butylborohydride, lithium triethylborohyhdride, lithium tri-t-butoxyaluminohydride or the like, more preferably sodium borohydride/cerium chloride, lithium n-butylborohydride, lithium triethylborohydride.

To thus obtained 20S- and 20R-allylalcohol intermediates is introduced a side chain corresponding to the compound of general formula (1) or (4) and the obtained compounds may be subjected to a sequence of reactions to give a compound of general formula (23) of the present invention as shown by the following scheme:

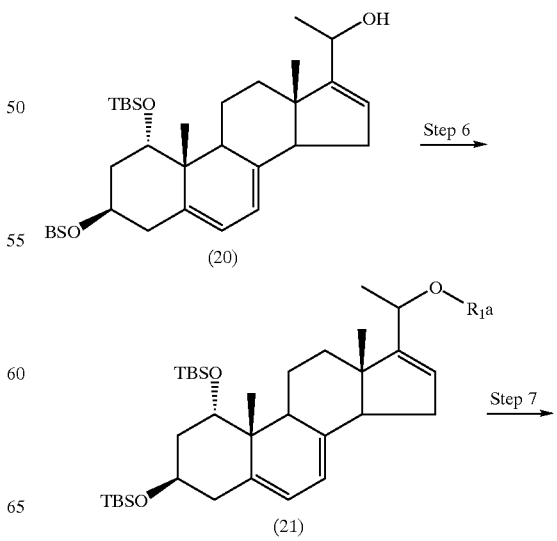

-continued

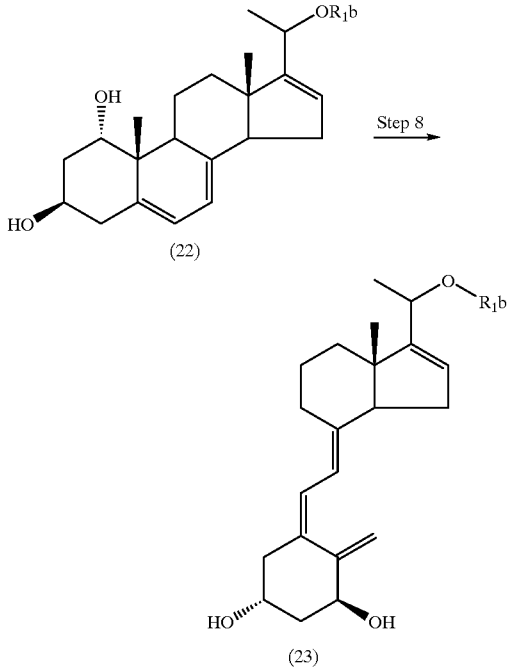

wherein TBS represents a t-butyldimethylsilyl group, $R_{1a}$ represents a saturated or unsaturated aliphatic hydrocarbon group which may be substituted by a hydroxyl group or a protected hydroxyl group, and $R_{1b}$ represents a saturated or unsaturated aliphatic hydrocarbon group substituted by a hydroxyl group.

A side chain may be introduced into the 20S- or 20R-allylalcohol of general formula (20) to give a compound of general formula (21) (step 6). The side chain can be introduced by reacting a compound of general formula (13) corresponding to the side chain:

wherein $R_{1a}$ and Y have the same meanings as above, with the allylalcohol intermediate mentioned above in the presence of a base.

Suitable bases for use in the above step 6 include alkali metal hydrides, alkali metal alkoxides, metal dialkylamides, alkyl metals or the like, preferably sodium hydride, potassium hydride, potassium t-butoxide, lithium diisopropylamide, lithium bistrimethylsilylamide, methyllithium, n-butyllithium, ethylmagnesium bromide or the like, more preferably sodium hydride, potassium hydride. This reaction may be performed in the presence of a catalytic amount of a crown ether. Suitable crown ethers include 15-crown-5, 18-crown-6, dibenzo-18-crown-6, preferably 15-crown-5.

Suitable solvents for use in the above step 6 include hydrocarbon-, ether- and amide-based solvents, such as benzene, toluene, diethyl ether, tetrahydrofuran, 1,2-dimethoxyethane, 1,4-dioxane, N,N-dimethylacetoamide, N,N-dimethylformamide, 1,3-dimethyl-2-imidazolidinone, 1,3-dimethyl-3,4,5,6-tetrahydro-2(1H)-pyrimidinone or the like, preferably tetrahydrofuran, 1,2-dimethoxyethane, N,N-dimethylformamide, 1,3-dimethyl-2-imidazolidinone, more preferably tetrahydrofuran.

The reaction temperature of the above step 6 is 0° C. to the boiling point or decomposition point of the solvent used, preferably room temperature to 100° C., more preferably 50 to 80° C.

The side chain may alternatively be introduced by, for example, alkylation with 1-bromo-2,3-epoxy-3-methylbutane as an alkyl halide in the presence of a base as mentioned above followed by ring-opening of the epoxide with a reducing agent such as lithium aluminium hydride, lithium borohydride, lithium tri-s-butylborohydride, lithium triethylborohydride. This process may be performed either in two steps or one step.

Instead of the alkyl halide, epoxides such as isobutyrene oxide, 1,2-epoxy-2-ethylbutane, 1,2-epoxy-3-methylbutane, 1,2-epoxy-3-ethylpentane may be used to introduce the side chain. The reaction conditions involve those described in, for example, JPA No. 80626/94 (Japanese Patent Application No. 158483/92), preferably using potassium t-butoxide as a base in the presence of dibenzo-18-crown-6 in toluene at 100 to 110° C.

The compound of general formula (21), which itself is among compounds of the present invention, can be converted into a compound of general formula (22) by deprotection (step 7). This removal of a t-butyldimethylsilyl group is carried out by a conventional procedure. Namely, the reagent used for the reaction includes hydrochloric acid, acidic ion exchange resin, tetrabutylammonium fluoride, hydrogen fluoride/pyridine, hydrogen fluoride/triethylamine, hydrofluoric acid, preferably tetrabutylammonium fluoride. Suitable solvents typically include etheric solvents, preferably tetrahydrofuran. The reaction temperature typically ranges from room temperature to 65° C., depending on the type of the substrate.

The compound of general formula (22) may be further subjected to photoreaction and thermal isomerization to give a compound of general formula (23) (step 8).

Steps 6, 7 and 8 may be carried out in the order described above, or in the order of step 6→step 8→step 7 or the order of step 8→step 6→step 7 (i.e. the order is not specifically limited, though step 7 can not precede step 6).

In the preparation process described above, each intermediate and final product can be purified and isolated by ordinary means such as silica gel column chromatography, thin layer chromatography, recrystallization.

Thus obtained compounds of general formula (1) are useful compounds as pharmaceutical agents such as antitumor agent or antirheumatic agent with weak hypercalcemic activity, as will be demonstrated in the examples.

The present invention encompasses compounds of general formula (1) having a steric configuration of either R or S at the 20-position or α or β in the hydroxyl group. The present invention also encompasses geometrical isomers in cis- and trans-configurations of the compound of general formula (1) wherein $R_1$ represents an unsaturated aliphatic hydrocarbon group which may be substituted by a hydroxyl group and which includes a double bond, as well as possible optical isomers and geometrical isomers.

More preferred compounds of general formula (1) of the present invention are those wherein $R_1$ represents an alkyl group substituted by a hydroxyl group, particularly 3-hydroxy-3-methylbutyl group. Preferred compounds are those substituted at the 1-position by a hydroxyl group, the hydroxyl group more preferably having α-configuration. Compounds having R-configuration at the 20-position are also preferred because of their strong differentiation-inducing activity. Compounds wherein X represents a sulfur atom can also be among preferred embodiments.

Specifically, compounds of general formula (1) of the present invention preferably include 1,3-dihydroxy-20-(3-hydroxy-3-methylbutylthio)-9,10-secopregna-5,7,10(19),16-tetraene, 1α,3β-dihydroxy-20(S)-(3-hydroxy-3- methylbutyl-thio)-9,10-secopregna-5,7,10(19),16-tetraene, 1α,3β-dihydroxy-20(R)-(3-hydroxy-3-methylbutylthio)-9,10-secopregna-5,7,10(19),16-tetraene.

More preferred specific compounds of general formula (1) of the present invention include 1α,3β-dihydroxy-20(R)-((E)- 4-hydroxy-4-methyl-2-pentenylthio)-9,10-secopregna-5,7,10(19),16-tetraene; 1α,3β-dihydroxy-20(R)-((E)-4-ethyl-4-hydroxy-2-hexenylthio)-9,10-secopregna-5,7,10(19),16-tetraene; 1α,3β-dihydroxy-20(S)-(2-hydroxy-2-methylpropyl-thio)-9,10-secopregna-5,7,10(19),16-tetraene; 1α,3β-dihydroxy-20(R)-(2-hydroxy-2-methylpropylthio)-9,10-secopregna-5,7,10(19),16-tetraene; 1α,3β-dihydroxy-20(S)-{2(S)-hydroxy-3-methylbutyloxy}-9,10-secopregna-5,7,10(19),16-tetraene; 1α,3β-dihydroxy-20(S)-{2(R)-hydroxy-3-methylbutyloxy}-9,10-secopregna-5,7,10(19),16-tetraene; 1α,3β-dihydroxy-20(S)-(2-ethyl-2-hydroxylbutylthio)-9,10-secopregna-5,7,10(19),16-tetraene; 1α,3β-dihydroxy-20(R)-(2-ethyl-2-hydroxylbutylthio)-9,10-secopregna-5,7,10(19),16-tetraene, etc.

Compounds of general formulae (4) to (7) for preparing these preferred compounds may also be among more preferred useful compounds as synthetic intermediates.

Compounds of the present invention are preferably formulated and used in appropriate dosage forms such as tablets, granules, parvules, capsules, powders, injections, solutions, suspensions, emulsions, transdermal absorbents, suppositories in combination with pharmaceutically acceptable carriers, excipients, disintegrants, lubricants, binders, perfumes, colorants, etc.

The dosage of compounds of the present invention can be appropriately chosen depending on the target disease, the condition, body type, constitution, age and sex of the patient, and the administration route, dosage form or other factors, but typically at least in the range of 0.001 $\mu$g to 0.1 $\mu$g, preferably about 0.01 $\mu$g daily and at most in the range of 100 $\mu$g to 10000 $\mu$g, preferably 200 $\mu$g to 1000 $\mu$g daily, which may be divided into 1 to 3 doses.

The following examples further illustrate the present invention, but are not construed as limiting the same.

EXAMPLES

In the following examples, the infrared absorption spectrum (IR) was measured by HITACHI 270-30. The $^1$H NMR was measured by JEOL FX-200 (200 MHz) or JEOL EX-270 (270 MHz) using tetramethylsilane as an internal standard in a CDCl$_3$ solvent. The mass spectrum (MS) was measured by SHIMADZU GCMS-QP 1000 in EI mode at an ionization voltage of 70 eV. The UV absorption spectrum (UV) was measured by SHIMADZU UV-240 in ethanol. Column chromatography was run on Merck Kieselgel 60 F254 Art. 9385 and preparative thin layer chromatography was run on Merck Kieselgel 60 F254 Art. 5744 (silica gel thickness 0.5 mm, 20×20 cm) or Art. 5715 (silica gel thickness 0.25 mm, 20×20 cm).

Example 1

Preparation of 1α,3β-bis(tert-butyldimethylsilyloxy)-20(S)-phenoxycarbonylthiopregna-5,7,16-triene To a solution of 1α,3β-bis(tert-butyldimethylsilyloxy)-16α-hydroxypregna-5,7,17(E)-triene (150 mg, 0.27 mmol) in dichloromethane (5 ml) were added pyridine (0.13 ml, 1.61 mmol) and phenyl chlorothionoformate (0.11 ml, 0.81 mmol), and the mixed solution was stirred at room temperature for one hour and then concentrated under reduced pressure. The residue was diluted with hexane and washed with ice-cooled 1N hydrochloric acid, saturated aqueous sodium bicarbonate solution and brine successively, and the organic layer was dried over magnesium sulfate. The solvent was removed under reduced pressure, and the resulting residue was purified by preparative thin layer chromatography (0.5 mm×4, hexane:ethyl acetate=9:1, developed once) to give the title compound as a colorless solid (160 mg, 85%).

IR(KBr): 2920, 2850, 1720, 1490, 1460, 1370, 1245, 1180, 1155, 1095, 1000 cm$^{-1}$. $^1$H NMR δ: 0.06(s, 3H), 0.07(s, 6H), 0.11(s, 3H), 0.89(s, 21H), 0.95(s, 3H), 1.60(d, J=7.3 Hz, 3H), 3.72(brs, 1H), 3.94–4.24(m, 2H), 5.41(brs, 1H), 5.61(d, J=5.4 Hz, 1H), 5.77(brs, 1H), 7.09–7.44(m, 5H). MS m/z: 694(M$^+$), 505(100%). UV $\lambda_{max}$ nm: 205, 270, 282, 293.

Example 2

Preparation of 1α-(tert-butyldimethylsilyloxy)-3β-hydroxy-20(S)-phenoxycarbonylthiopregna-5,7,16-triene In the same manner as in Example 1, 1α,3β-bis(tert-butyldimethylsilyloxy)-16α-hydroxypregna-5,7,17(E)-triene (1.50 g, 2.68 mmol), pyridine (1.30 ml, 16.1 mmol) and phenyl thionochloroformate (1.11 ml, 8.04 mmol) were reacted in dichloromethane (50 ml) and worked up, then the residue was dissolved in tetrahydrofuran (50 ml) without purification and stirred with Amberlyst 15 (3.00 g) at room temperature for 36 hours. The resin was filtered and washed with tetrahydrofuran, then the filtrate was concentrated under reduced pressure and the residue was purified by column chromatography (hexane:ethyl acetate=7:1→5:1) to give the title compound as a colorless oil (1.07 g, 69%).

IR(neat): 3250, 2920, 2850, 1720, 1490, 1460, 1370, 1260, 1190, 1165, 1100 cm$^{-1}$. $^1$H NMR δ: 0.08(s, 3H), 0.12(s, 3H), 0.88(s, 9H), 0.95(s, 3H), 0.96(s, 3H), 1.60(d, J=6.8 Hz, 3H), 3.76(brs, 1H), 3.99–4.24(m, 2H), 5.37–5.46 (m, 1H), 5.60–5.68(m, 1H), 5.78(brs, 1H), 7.12–7.45(m, 5H). MS m/z: 580 (M$^+$), 277 (100%). UV $\lambda_{max}$ nm: 205, 270, 282, 293.

Example 3

Preparation of 1α-(tert-butyldimethylsilyloxy)-3β-hydroxy-20((S)-(3-hydroxy-3-methylbutylthio)pregna-5,7,16-triene To a solution of 1α-(tert-butyldimethylsilyloxy)-3β-hydroxy-20(S)-phenoxycarbonylthiopregna-5,7,16-triene (81.6 mg, 0.140 mmol) and 4-bromo-2-methyl-2-butanol (117 mg, 0.700 mmol) in tetrahydrofuran (1 ml) was added 1M KOH solution in methanol (1 ml), and the mixed solution was stirred at room temperature for 30 minutes, then concentrated under reduced pressure. The residue was diluted with hexane, washed with brine and dried over magnesium sulfate, and then the solvent was distilled off under reduced pressure. The resulting residue was purified by preparative thin layer chromatography (0.5 mm×2, dichloromethane:ethyl acetate=8:1, developed once) to give the title compound as a colorless oil (60.3 mg, 79%).

IR(neat): 3400, 2950, 2850, 1460, 1370, 1250, 1200, 1150, 1060 cm$^-$. $^1$H NMR δ: 0.08(s, 3H), 0.13(s, 3H), 0.88(s, 9H), 0.93(s, 3H), 0.94(s, 3H), 1.22(s, 6H), 1.43(d, J=6.9 Hz, 3H), 3.51(q, J=6.9 Hz, 1H), 3.75(brs, 1H), 3.95–4.17(m, 1H), 5.37–5.45(br, 1H), 5.59–5.69(br, 2H). MS m/z: 546 (M$^+$), 278 (100%). UV $\lambda_{max}$ nm: 270, 281, 293.

Example 4

Preparation of 1α-(tert-butyldimethylsilyloxy)-3β-hydroxy-20(S)-(4-methyl-4-triethylsilyloxypentylthio)pregna-5,7,16-triene Under the same conditions as in Example 3, 1α-(tert-butyldimethylsilyloxy)-3β-hydroxy-20(S)-phenoxycarbonyl-thiopregna-5,7,16-triene (82.4 mg, 0.142 mmol), 1-bromo-4-methyl-4-triethylsilyloxypentane (209 mg, 0.709 mmol), tetrahydrofuran (1 ml) and 1M KOH solution in methanol (1 ml) were reacted and worked up, and then the residue was purified by preparative thin layer chromatography (0.5 mm×2, hexane:ethyl acetate=3:2, developed once) to give the title compound as a colorless oil (56.1 mg, 59%).

IR(neat): 3350, 2950, 2850, 1460, 1365, 1255, 1150, 1050 cm$^{-1}$. $^1$H NMR δ: 0.08(s, 3H), 0.13(s, 3H), 0.56(q, J=7.7 Hz, 6H), 0.81–1.03(m, 24H), 1.19(s, 6H), 1.42(d, J=6.9 Hz, 3H), 3.46(q, J=6.9 Hz, 1H), 3.76(brs, 1H), 4.00–4.16(m, 1H), 5.39–5.47(m, 1H), 5.59–5.71(m, 2H). MS m/z: 674(M$^+$), 277(100%). UV λ$_{max}$ nm: 270, 281, 293.

Example 5
Preparation of 1α-(tert-butyldimethylsilyloxy)-3β-hydroxy-20(S)-(5-hydroxy-5-methylhexylthio)pregna-5,7,16-triene Under the same conditions as in Example 3, 1α-(tert-butyldimethylsilyloxy)-3β-hydroxy-20(S)-phenoxycarbonyl-thiopregna-5,7,16-triene (82.6 mg, 0.142 mmol), 6-bromo-2-methyl-2-hexanol (139 mg, 0.710 mmol), tetrahydrofuran (1 ml) and 1M KOH solution in methanol (1 ml) were reacted and worked up, and then the residue was purified by preparative thin layer chromatography (0.5 mm×2, dichloromethane:ethyl acetate=8:1, developed once) to give 87.2 mg of a product, which was directly used in the subsequent reaction because it was difficult to separate from 6-bromo-2-methyl-2-hexanol.

Example 6
Preparation of 1α-(tert-butyldimethylsilyloxy)-3β-hydroxy-20(S)-(2-hydroxy-2-methylpropylthio)pregna-5,7,16-triene Under the same conditions as in Example 3, 1α-(tert-butyldimethylsilyloxy)-3β-hydroxy-20(S)-phenoxycarbonyl-thiopregna-5,7,16-triene (83.0 mg, 0.143 mmol), isobutylene oxide (113 mg, 1.56 mmol), tetrahydrofuran (0.5 ml) and 1M KOH solution in methanol (0.5 ml) were reacted and worked up, and then the residue was purified by preparative thin layer chromatography (0.5 mm×2, hexane:ethyl acetate=1:1, developed once) to give the title compound as a colorless oil (62.3 mg, 82%).

IR(neat): 3400, 2950, 2850, 1460, 1370, 1250, 1200, 1150, 1060 cm$^{-1}$. $^1$H NMR δ: 0.08(s, 3H), 0.12(s, 3H), 0.88(s, 9H), 0.94(s, 6H), 1.26(s, 3H), 1.27(s, 3H), 1.44(d, J=6.9 Hz, 3H), 3.49(q, J=6.9 Hz, 1H), 3.76(brs, 1H), 4.00–4.17(m, 1H), 5.36–5.47(m, 1H), 5.59–5.69(m, 2H). MS m/z: 532(M$^+$), 278(100%). UV λ$_{max}$ nm: 270, 281, 293.

Example 7
Preparation of 1α-(tert-butyldimethylsilyloxy)-3β-hydroxy-20(S)-(3-ethyl-3-hydroxypentylthio)pregna-5,7,16-triene Under the same conditions as in Example 3, 1α-(tert-butyldimethylsilyloxy)-3β-hydroxy-20(S)-phenoxycarbonyl-thiopregna-5,7,16-triene (82.8 mg, 0.143 mmol), 5-bromo-3-ethyl-3-pentanol (139 mg, 0.715 mmol), tetrahydrofuran (1 ml) and 1M KOH solution in methanol (1 ml) were reacted and worked up, and then the residue was purified by preparative thin layer chromatography (0.5 mm×2, dichloromethane:ethyl acetate=8:1, developed once) to give 99.6 mg of a product, which was directly used in the subsequent reaction because it was difficult to separate from 5-bromo-3-ethyl-3-pentanol.

Example 8
Preparation of 1α-(tert-butyldimethylsilyloxy)-3β-hydroxy-20(S)-(4-ethyl-4-hydroxyhexylthio)pregna-5,7,16-triene Under the same conditions as in Example 3, 1α-(tert-butyldimethylsilyloxy)-3β-hydroxy-20(S)-phenoxycarbonyl-thiopregna-5,7,16-triene (84.3 mg, 0.145 mmol), 6-bromo-3-ethyl-3-hexanol (152 mg, 0.725 mmol), tetrahydrofuran (1 ml) and 1M KOH solution in methanol (1 ml) were reacted and worked up, and then the residue was purified by preparative thin layer chromatography (0.5 mm×2, hexane:ethyl acetate=2:1, developed twice) to give 76.4 mg of a product, which was directly used in the subsequent reaction because it was difficult to separate from 6-bromo-3-ethyl-3-hexanol.

Example 9
Preparation of 1α,3β-dihydroxy-20(S)-(3-hydroxy-3-methylbutylthio)pregna-5,7,16-triene To a solution of 1α-(tert-butyldimethylsilyloxy)-3β-hydroxy-20(S)-(3-hydroxy-3-methylbutylthio)pregna-5,7,16-triene (58.5 mg, 0.107 mmol) in tetrahydrofuran (3 ml) was added 1M tetra-n-butylammonium fluoride solution in tetrahydrofuran (2 ml), and the mixed solution was heated under reflux for 4 hours. After completion of the reaction, the reaction solution was diluted with ethyl acetate, and washed with ice-cooled 0.5 N hydrochloric acid, saturated aqueous sodium bicarbonate solution and brine successively, and the organic layer was dried over magnesium sulfate. The solvent was removed under reduced pressure, and the resulting residue was purified by preparative thin layer chromatography (0.5 mm×2, dichloromethane:ethanol=7:1, developed once) to give the title compound as a pale yellow oil (41.8 mg, 90%).

IR (neat): 3400, 2950, 1460, 1370, 1210, 1150, 1060 cm$^{-1}$. $^1$H NMR δ: 0.93(s, 3H), 0.96(s, 3H), 1.22(s, 6H), 1.42(d, J=6.8 Hz, 3H), 3.52(q, J=6.8 Hz, 1H), 3.77(brs, 1H), 3.96–4.16(m, 1H), 5.38–5.48(m, 1H), 5.59–5.65(brs, 1H), 5.66–5.76(m, 1H). MS m/z: 432(M$^+$), 312(100%). UV λ$_{max}$ nm: 270, 281, 293.

Example 10
Preparation of 1α,3β-di-hydroxy-20(S)-(4-hydroxy-4-methylpentylthio)pregna-5,7,16-triene Under the same conditions as in Example 9, 1α-(tert-butyldimethylsilyloxy)-3β-hydroxy-20(S)-(4-methyl-4-triethylsilyloxypentylthio)pregna-5,7,16-triene (55.7 mg, 0.0825 mmol), tetrahydrofuran (2 ml) and 1M tetra-n-butylammonium fluoride solution in tetrahydrofuran (2 ml) were reacted and worked up, and then the residue was purified by preparative thin layer chromatography (0.5 mm×2, dichloromethane:ethanol=7:1, developed once) to give the title compound as a colorless oil (34.1 mg, 92%).

IR(neat): 3400, 2950, 2850, 1460, 1370, 1200, 1150, 1100, 1160 cm$^{-1}$. $^1$H NMR δ: 0.92(s, 3H), 0.97(s, 3H), 1.21(s, 6H), 1.42(d, J=6.9 Hz, 3H), 3.47(q, J=6.9 Hz, 1H), 3.77(brs, 1H), 3.98–4.16(m, 1H), 5.39–5.50(m, 1H), 5.62 (brs, 1H), 5.69–5.77(m, 1H). MS m/z: 446(M$^+$), 312(100%). UV λ$_{max}$ nm: 270, 281, 293.

Example 11
Preparation of 1α,3β-dihydroxy-20(S)-(5-hydroxy-5-methylhexylthio)pregna-5,7,16-triene Under the same conditions as in Example 9, the crude 1α-(tert-butyldimethylsilyloxy)-3β-hydroxy-20(S)-(5-hydroxy-5-methylhexylthio)pregna-5,7,16-triene (73.2 mg) obtained in Example 5, tetrahydrofuran (2 ml) and 1M tetra-n-butylammonium fluoride solution in tetrahydrofuran (2 ml) were reacted and worked up, and then the residue was purified by preparative thin layer chromatography (0.5 mm×2, dichloromethane:ethanol=7:1, developed once) to give the title compound as a pale yellow oil (36.1 mg, 55%, 2 steps).

IR(neat): 3400, 2950, 1460, 1370, 1200, 1145, 1050 cm$^{-1}$. $^1$H NMR δ: 0.93(s, 3H), 0.98(s, 3H), 1.08(s, 6H), 1.42(d, J=6.9 Hz, 3H), 3.46(q, J=6.9 Hz, 1H), 3.78(brs, 1H), 3.98–4.16(m, 1H), 5.41–5.50(m, 1H), 5.61(brs, 1H), 5.69–5.78(m, 1H). MS m/z: 460(M$^+$), 312(100%). UV $\lambda_{max}$ nm: 270, 281, 293.

Example 12

Preparation of 1α,3β-dihydroxy-20(S)-(2-hydroxy-2-methylpropylthio)pregna-5,7,16-triene Under the same conditions as in Example 9, 1α-(tert-butyldimethylsilyloxy)-3β-hydroxy-20(S)-(5-hydroxy-5-methylhexylthio)pregna-5,7,16-triene (60.1 mg, 0.113 mmol), tetrahydrofuran (2 ml) and 1M tetra-n-butylammonium fluoride solution in tetrahydrofuran (2 ml) were reacted and worked up, and then the residue was purified by preparative thin layer chromatography (0.5 mm×2, dichloromethane:ethanol 7:1, developed once) to give the title compound as a colorless oil (36.3 mg, 77%).

IR(neat): 3400, 2950, 1460, 1370, 1250, 1210, 1150, 1060 cm$^{-1}$. $^1$H NMR δ: 0.94(s, 3H), 0.97(s, 3H), 1.26(s, 3H), 1.27(s, 3H), 1.43(d, J=6.8 Hz, 3H), 3.50(q, J=6.8 Hz, 1H), 3.77(brs, 1H), 3.96–4.16(m, 1H), 5.40–5.51(m, 1H), 5.64 (brs, 1H), 5.68–5.98(m, 1H). MS m/z: 418(M$^+$), 312(100%). UV $\lambda_{max}$ nm: 270, 281, 293.

Example 13

Preparation of 1α,3β-dihydroxy-20(S)-(3-ethyl-3-hydroxypentylthio)pregna-5,7,16-triene Under the same conditions as in Example 9, the crude 1α-(tert-butyldimethylsilyloxy)-3β-hydroxy-20(S)-(3-ethyl-3-hydroxypentylthio)pregna-5,7,16-triene obtained in Example 7, tetrahydrofuran (2 ml) and 1M tetra-n-butylammonium fluoride solution in tetrahydrofuran (2 ml) were reacted and worked up, and then the residue was purified by preparative thin layer chromatography (0.5 mm×2, dichloromethane:ethanol=7:1, developed once) to give the title compound as a colorless oil (42.0 mg, 64%, 2 steps).

IR(neat): 3400, 2950, 1460, 1370, 1150, 1060 cm$^{-1}$. $^1$H NMR δ: 0.85(t, J=7.3 Hz, 6H), 0.94(s, 3H), 0.96(s, 3H), 1.43(d, J=6.8 Hz, 3H), 1.46(q, J=7.3 Hz, 4H), 3.51(q, J=6.8 Hz, 1H), 3.78(brs, 1H), 3.90–4.09(m, 1H), 5.38–5.49(m, 1H), 5.63(brs, 1H), 5.66–5.78(m, 1H). MS m/z: 460(M$^+$), 312(100%). UV $\lambda_{max}$ nm: 270, 281, 293.

Example 14

Preparation of 1α,3β-dihydroxy-20(S)-(4-ethyl-4-hydroxyhexylthio)pregna-5,7,16-triene Under the same conditions as in Example 9, the crude 1α-(tert-butyldimethylsilyloxy)-3β-hydroxy-20(S)-(4-ethyl-4-hydroxyhexylthio)pregna-5,7,16-triene (71.4 mg) obtained in Example 8, tetrahydrofuran (2 ml) and 1M tetra-n-butylammonium fluoride solution in tetrahydrofuran (2 ml) were reacted and worked up, and then the residue was purified by preparative thin layer chromatography (0.5 mm×2, dichloromethane:ethanol=7:1, developed once) to give the title compound as a colorless oil (45.8 mg, 67%, 2 steps).

IR(neat): 3400, 2950, 1450, 1370, 1050 cm$^{-1}$. $^1$H NMR δ: 0.85(t, J=7.3 Hz, 6H), 0.94(s, 3H), 0.98(s, 3H), 3.51(q, J=6.8 Hz, 1H), 3.78(brs, 1H), 3.98–4.16(m, 1H), 5.38–5.50(m, 1H), 5.63(brs, 1H), 5.69–5.78(m, 1H). MS m/z: 474(M$^+$), 312(100%). UV $\lambda_{max}$ nm: 270, 281, 293.

Example 15

Preparation of 1α,3β-dihydroxy-20(S)-(3-hydroxy-3-methylbutylthio)-9,10-secopregna-5,7,10(19),16-tetraene In ethanol (200 ml) was dissolved 1α,3β-dihydroxy-20 (S)-(3-hydroxy-3-methylbutylthio)pregna-5,7,16-triene (40.2 mg, 0.0929 mmol) and irradiated with a 400 W high pressure mercury lamp through a vicol filter for 3.5 minutes while argon was bubbled with stirring at 0° C., and then the solution was heated under reflux for 1.5 hours. After cooling to room temperature, the solvent was removed under reduced pressure and the resulting residue was purified by preparative thin layer chromatography (0.5 mm×1, dichloromethane:ethanol=7:1, developed once, then 0.5 mm×1, hexane:ethyl acetate:ethanol=10:10:1, developed three times) to give the title compound as a colorless oil (3.66 mg, 9.1%).

IR(neat): 3400, 2920, 1440, 1365, 1200, 1140, 1060 cm$^{-1}$. $^1$H NMR δ: 0.83(s, 3H), 1.23(s, 6H), 1.42(d, J=7.3 Hz, 3H), 3.49(q, J=7.3 Hz, 1H), 4.18–4.32(m, 1H), 4.39–4.52(m, 1H), 5.01(brs, 1H), 5.34(brs, 1H), 5.61(brs, 1H), 6.10(d, J=11.2 Hz, 1H), 6.37(d, J=11.2 Hz, 1H). MS m/z: 432(M$^+$), 312 (100%). UV $\lambda_{max}$ nm: 263.

Example 16

Preparation of 1α,3β-dihydroxy-20(S)-(4-hydroxy-4-methylpentylthio)-9,10-secopregna-5,7,10(19),16-tetraene Using 1α,3β-dihydroxy-20(S)-(4-hydroxy-4-methylpentylthio)pregna-5,7,16-triene (33.4 mg, 0.0748 mmol) and ethanol (200 ml), the reaction was performed by the same procedure as in Example 15 (irradiation for 2 minutes and heating under reflux for 2 hours), and then the residue was purified by preparative thin layer chromatography (0.5 mm×2, dichloromethane:ethanol=7:1, developed once, then 0.5 mm×1, hexane:ethyl acetate:ethanol=10:10:1, developed three times) to give the title compound as a colorless oil (3.10 mg, 9.3%).

IR(neat): 3400, 2930, 1450, 1370, 1220, 1150, 1060 cm$^{-1}$. $^1$H NMR δ: 0.83(s, 3H), 1.21(s, 6H), 1.41(d, J=6.8 Hz, 3H), 3.44(q, J=6.8 Hz, 1H), 4.18–4.32(m, 1H), 4.40–4.52(m, 1H), 5.01(brs, 1H), 5.34(brs, 1H), 5.59(brs, 1H), 6.10(d, J=11.2 Hz, 1H), 6.38(d, J=11.2 Hz, 1H). MS m/z: 446(M$^+$), 312 (100%). UV $\lambda_{max}$ nm: 263.

Example 17

Preparation of 1α,3β-dihydroxy-20(S)-(5-hydroxy-5-methylhexylthio)-9,10-secopregna-5,7,10(19),16-tetraene Using 1α,3β-dihydroxy-20(S)-(5-hydroxy-5-methylhexylthio)pregna-5,7,16-triene (35.7 mg, 0.0749 mmol) and ethanol (200 ml), the reaction was performed by the same procedure as in Example 15 (irradiation for 2.75 minutes and heating under reflux for 2 hours), and then the residue was purified by preparative thin layer chromatography (0.5 mm×2, dichloromethane:ethanol=8:1, developed once, then 0.5 mm×1, hexane:ethyl acetate:ethanol=12:8:1, developed three times) to give the title compound as a colorless oil (2.94 mg, 8.2%).

IR(neat): 3400, 2930, 1460, 1370, 1200, 1140, 1050 cm$^{-1}$. $^1$H NMR δ: 0.83(s, 3H), 1.21(s, 6H), 1.41(d, J=6.8 Hz, 3H), 3.44(q, J=6.8 Hz, 1H), 4.18–4.32(m, 1H), 4.40–4.52(m, 1H), 5.02(brs, 1H), 5.34(brs, 1H), 5.59(brs, 1H), 6.10(d, J=11.2 Hz, 1H), 6.38(d, J=11.2 Hz, 1H). MS m/z: 460(M$^+$), 312 (100%). UV $\lambda_{max}$ nm: 263.

Example 18

Preparation of 1α,3β-dihydroxy-20(S)-(2-hydroxy-2-methylpropylthio)-9,10-secopregna-5,7,10(19),16-tetraene Using 1α,3β-dihydroxy-20(S)-(2-hydroxy-2-methylpropylthio)pregna-5,7,16-triene (36.0 mg, 0.0860 mmol) and ethanol (200 ml), the reaction was performed by the same procedure as in Example 15 (irradiation for 2.75 minutes and heating under reflux for 2 hours), and then the residue was purified by preparative thin layer chromatography (0.5 mm×1, dichloromethane:ethanol=7:1, developed once, then 0.5 mm×1, hexane:ethyl acetate:ethanol=10:10:1, developed three times) to give the title compound as a colorless oil (2.60 mg, 7.2%).

IR(neat): 3400, 2930, 1460, 1370, 1200, 1140, 1060 cm$^{-1}$. $^1$H NMR δ: 0.84(s, 3H), 1.25(s, 3H), 1.26(s, 3H), 1.43(d, J=6.9 Hz, 3H), 3.47(q, J=6.9 Hz, 1H), 4.16–4.30(m, 1H), 4.38–4.50(m, 1H), 5.01(brs, 1H), 5.34(brs, 1H), 5.62(brs, 1H), 6.11(d, J=11.2 Hz, 1H), 6.37(d, J=11.2 Hz, 1H). MS m/z: 418(M$^+$), 312(100%). UV λ$_{max}$ nm: 263.

Example 19
Preparation of 1α,3β-dihydroxy-20(S)-(3-ethyl-3-hydroxypentylthio)-9,10-secopregna-5,7,10(19),16-tetraene Using 1α,3β-dihydroxy-20(S)-(3-ethyl-3-hydroxypentylthio)pregna-5,7,16-triene (41.7 mg, 0.0905 mmol) and ethanol (200 ml), the reaction was performed by the same procedure as in Example 15 (irradiation for 2.25 minutes and heating under reflux for 2 hours), and then the residue was purified by preparative thin layer chromatography (0.5 mm×1, dichloromethane:ethanol=7:1, developed once, then 0.5 mm×1, hexane:ethyl acetate:ethanol=12:8:1, developed three times, then 0.5mm×1, dichloromethane:ethyl acetate:ethanol=28:12:1) to give the title compound as a colorless oil (3.78 mg, 9.1%).

IR(neat): 3400, 2930, 1450, 1370, 1060 cm$^{-1}$. $^1$H NMR δ: 0.83(s, 3H), 0.86(t, J=7.3 Hz, 6H), 1.42(d, J=6.8 Hz, 3H), 1.47(q, J=7.3 Hz, 4H), 3.49(q, J=6.8 Hz, 1H), 4.27–4.32(m, 1H), 4.38–4.52(m, 1H), 5.02(brs, 1H), 5.34(brs, 1H), 5.61 (brs, 1H), 6.10(d, J=11.2 Hz, 1H), 6.37(d, J=11.2 Hz, 1H). MS m/z: 460(M$^+$), 312(100%). UV λ$_{max}$ nm: 263.

Example 20
Preparation of 1α,3β-dihydroxy-20(S)-(4-ethyl-4-hydroxyhexylthio)-9,10-secopregna-5,7,10(19),16-tetraene Using 1α,3β-dihydroxy-20(S)-(4-ethyl-4-hydroxyhexylthio)pregna-5,7,16-triene (44.7 mg, 0.0942 mmol) and ethanol (200 ml), the reaction was performed by the same procedure as in Example 15 (irradiation for 2.25 minutes and heating under reflux for 2 hours), and then the residue was purified by preparative thin layer chromatography (0.5 mm×2, dichloromethane:ethyl acetate:ethanol= 14:6:1, developed three times, then 0.5 mm×1, hexane:ethyl acetate:ethanol=12:8:1, developed three times) to give the title compound as a colorless oil (3.62 mg, 8.1%).

IR(neat): 3400, 2930, 1450, 1370, 1050 cm$^{-1}$. $^1$H NMR δ: 0.83(s, 3H), 0.91(t, J=7.3 Hz, 6H), 3.48(q, J=6.8 Hz, 1H), 4.18–4.36(m, 1H), 4.38–4.53(m, 1H), 5.01(brs, 1H), 5.34 (brs, 1H), 5.60(brs, 1H), 6.10(d, J=11.2 Hz, 1H), 6.37(d, J=11.2 Hz, 1H). MS m/z: 474(M$^+$), 312(100%). UV λ$_{max}$ nm: 263.

Example 21
Preparation of 1α-(tert-butyldimethylsilyloxy)-3β-hydroxy-20(S)-(4-hydroxy-4-methyl-2-pentynylthio)pregna-5,7,16-triene Under the same conditions as in Example 3, 1α-(tert-butyldimethylsilyloxy)-3β-hydroxy-20(S)-phenoxycarbonylthiopregna-5,7,16-triene (59.4 mg, 0.102 mmol), 5-bromo-2-methyl-3-pentyn-2-ol (90.5 mg, 0.511 mmol), tetrahydrofuran (1 ml) and 1M KOH solution in methanol (1 ml) were reacted and worked up, and then the residue was purified by preparative thin layer chromatography (0.5 mm×2, dichloromethane:ethyl acetate=5:1, developed twice) to give the title compound as a colorless oil (41.6 mg, 73%).

IR(neat): 3400, 2950, 2850, 1460, 1370, 1250, 1150, 1060 cm$^{-1}$. $^1$H NMR δ: 0.08(s, 3H), 0.12(s, 3H), 0.88(s, 9H), 0.93(s, 3H), 0.94(s, 3H), 1.46(d, J=7.3 Hz, 3H), 1.51(s, 6H), 3.18(d, J=16.6 Hz, 1H), 3.22(d, J=16.6 Hz, 1H), 3.67(q, J=7.3 Hz, 1H), 3.76(brs, 1H), 3.96–4.10(m, 1H), 5.32–5.44 (m, 1H), 5.56–5.71(m, 2H). MS m/z: 556(M$^+$), 188(100%). UV λ$_{max}$ nm: 270, 281, 293.

Example 22
Preparation of 1α-(tert-butyldimethylsilyloxy)-3β-hydroxy-20(S)-{(E)-4-hydroxy-4-methyl-2-pentenylthio}pregna-5,7,16-triene Under the same conditions as in Example 3, 1α-(tert-butyldimethylsilyloxy)-3β-hydroxy-20(S)-phenoxycarbonylthiopregna-5,7,16-triene (33.5 mg, 0.0577 mmol), (E)-5-bromo-2-methyl-3-penten-2-ol (41.2 mg, 0.230 mmol), tetrahydrofuran (0.5 ml) and 1M KOH solution in methanol (0.5 ml) were reacted and worked up, and then the residue was purified by preparative thin layer chromatography (0.5 mm×1, dichloromethane:ethyl acetate=5:1, developed twice) to give 26.2 mg of a product, which was directly used in the subsequent reaction because it was difficult to separate from (E)-5-bromo-2-methyl-3-penten-2-ol.

Example 23
Preparation of 1α,3β-bis(tert-butyldimethylsilyloxy)-20(S)-{(Z)-4-methyl-4-triethylsilyloxy-2-pentenylthio}pregna-5,7,16-triene Under the same conditions as in Example 3, 1α,3β-bis (tert-butyldimethylsilyloxy)-20(S)-phenoxycarbonylthiopregna-5,7,16-triene (91.2 mg, 0.131 mmol), (Z)-1-bromo-4-methyl-4-triethylsilyloxy-2-pentene (192 mg, 0.655 mmol), tetrahydrofuran (1.5 ml) and 1M KOH solution in methanol (1.5 ml) were reacted and worked up, and then the residue was purified by preparative thin layer chromatography (0.5 mm×2, hexane:dichloromethane:ethyl acetate=160:40:1, developed once) to give the title compound as a colorless oil (66.3 mg, 64%).

IR(neat): 2950, 2850, 1460, 1170, 1250, 1160, 1080 cm$^{-1}$. $^1$H NMR δ: 0.06(s, 3H), 0.07(s, 6H), 0.11(s, 3H), 0.60(g, J=7.3 Hz, 6H), 0.89(s, 18H), 0.90–1.04(m, 15H), 1.37(s, 6H), 1.44(d, J=6.8 Hz, 3H), 3.33(dd, J=13.0, 6.8 Hz, 1H), 3.41–3.60(m, 2H), 3.72(brs, 1H), 3.96–4.16(m, 1H), 5.23–5.52(m, 3H), 5.55–5.68(m, 2H). MS m/z: 786(M$^+$), 278(100%). UV λ$_{max}$ nm: 270, 281, 293.

Example 24
Preparation of 1α-(tert-butyldimethylsilyloxy)-3β-hydroxy-20(S)-(4-ethyl-4-hydroxy-2-hexynylthio)pregna-5,7,16-triene Under the same conditions as in Example 3, 1α-(tert-butyldimethylsilyloxy)-3β-hydroxy-20(S)-phenoxycarbonylthiopregna-5,7,16-triene (60.8 mg, 0.105 mmol), 6-bromo-3-ethyl-4-hexyn-3-ol (108 mg, 0.525 mmol), tetrahydrofuran (1 ml) and 1M KOH solution in methanol (1 ml) were reacted and worked up, and then the residue was purified by preparative thin layer chromatography (0.5 mm×2, dichloromethane:ethyl acetate=5:1, developed twice) to give the title compound as a colorless oil (38.4 mg, 63%).

IR(neat): 3400, 2950, 2850, 1460, 1370, 1250, 1150, 1060 cm$^{-1}$. $^1$H NMR δ: 0.08(s, 3H), 0.12(s, 3H), 0.88(s, 9H), 0.92(s, 3H), 0.94(s, 3H), 1.03(t, J=7.3 Hz, 6H), 1.46(d, J=6.8 Hz, 3H), 1.66(q, J=7.3 Hz, 4H), 3.20(d, J=16.6 Hz, 1H), 3.24(d, J=16.6 Hz, 1H), 3.68(q, J=6.8 Hz, 1H), 3.75(brs, 1H), 3.96–4.12(m, 1H), 5.35–5.44(m, 1H), 5.57–5.71(m, 2H). MS m/z: 566(M$^+$-H$_2$O), 187 (100%). UV λ$_{max}$ nm: 270, 281, 293.

Example 25
Preparation of 1α-(tert-butyldimethylsilyloxy)-3β-hydroxy-20(S)-{(E)-4-ethyl-4-hydroxy-2-hexenylthio}pregna-5,7,16-triene Under the same conditions as in Example 3, 1α-(tert-butyldimethylsilyloxy)-3β-hydroxy-20(S)-phenoxycarbonylthiopregna-5,7,16-triene (33.1 mg, 0.0570 mmol), (E)-6-bromo-3-ethyl-4-hexen-3-ol (47.4 mg, 0.229 mmol), tetrahydrofuran (0.5 ml) and 1M KOH solution in methanol (0.5 ml) were reacted and worked up, and then the residue was purified by preparative thin layer chromatography (0.5 mm×1, dichloromethane:ethyl acetate=5:1, developed twice) to give the title compound as a colorless oil (28.2 mg, 84%).

IR(neat): 3400, 2920, 2850, 1460, 1370, 1250, 1150, 1060 cm$^{-1}$. $^1$H NMR δ: 0.08(s, 3H), 0.12(s, 3H), 0.87(t, J=7.3 Hz, 6H), 0.88(s, 9H), 1.42(d, J=6.8 Hz, 3H), 1.54(q, J=7.3 Hz, 4H), 3.10(dd, J=12.6, 5.5 Hz, 1H), 3.12(dd, J=12.6, 5.5 Hz, 1H), 3.45(q, J=6.8 Hz, 1H), 3.75(brs, 1H), 3.96–4.15(m, 1H), 5.35–5.44(m, 1H), 5.45–5.73(m, 4H). MS m/z: 586 (M$^+$), 277(100%). UV $\lambda_{max}$ nm: 270, 281, 293.

Example 26

Preparation of 1α-(tert-butyldimethylsilyloxy)-3β-hydroxy-20(S)-{(Z)-4-ethyl-4-triethylsilyloxy-2-hexenylthio}pregna-5,7,16-triene Under the same conditions as in Example 3, 1α-(tert-butyldimethylsilyloxy)-3β-hydroxy-20(S)-phenoxycarbonylthiopregna-5,7,16-triene (33.0 mg, 0.0568 mmol), (Z)-1-bromo-4-ethyl-4-triethylsilyloxy-2-hexene (91.0 mg, 0.284 mmol), tetrahydrofuran (0.5 ml) and 1M KOH solution in methanol (0.5 ml) were reacted and worked up, and then the residue was purified by preparative thin layer chromatography (0.5 mm×1, hexane:ethyl acetate=2:1, developed once) to give the title compound as a pale yellow oil (23.8 mg, 60%).

IR(neat): 3400, 2950, 2850, 1460, 1350, 1250, 1140, 1060 cm$^{-1}$. $^1$H NMR δ: 0.08(s, 3H), 0.12(s, 3H), 0.62(q, J=7.5 Hz, 6H), 0.80–1.05(m, 30H), 1.44(d, J=6.8 Hz, 3H), 1.57(q, J=7.3 Hz, 4H), 3.28–3.59(m, 3H), 3.76(brs, 1H), 3.97–4.28 (m, 1H), 5.23(d, J=11.2 Hz, 1H), 5.35–5.53(m, 2H), 5.56–5.72(m, 2H). MS m/z: 700(M$^+$), 278(100%). UV $\lambda_{max}$ nm: 270, 281, 293.

Example 27

Preparation of 1α-(tert-butyldimethylsilyloxy)-3β-hydroxy-20(S)-(4-hydroxy-4-methyl-2-pentynylthio)-2,10-secopregna-5,7,10(19),16-tetraene Using 1α-(tert-butyldimethylsilyloxy)-3β-hydroxy-20 (S)-(4-hydroxy-4-methyl-2-pentynylthio)pregna-5,7,16-triene (41.6 mg, 0.0747 mmol) and ethanol (200 ml), the reaction was performed by the same procedure as in Example 15 (irradiation for 2 minutes and heating under reflux for 1.5 hours), and then the residue was purified by preparative thin layer chromatography (0.5 mm×1, dichloromethane:ethyl acetate=6:1, developed three times, then 0.5 mm×1, hexane:ethyl acetate=3:1, developed three times) to give the title compound as a colorless oil (3.8 mg, 9.1%).

IR(neat): 3400, 2930, 2850, 1460, 1360, 1245, 1160, 1060 cm$^{-1}$. $^1$H NMR δ: 0.09(s, 6H), 0.82(s, 3H), 0.90(s, 9H), 1.45(d, J=7.3 Hz, 3H), 1.51(s, 6H), 3.18(d, J=16.6 Hz, 1H), 3.21(d, J=16.6 Hz, 1H), 3.66(q, J=7.3 Hz, 1H), 4.16–4.28(m, 1H), 4.34–4.43(m, 1H), 4.92(brs, 1H), 5.27(brs, 1H), 5.64 (brs, 1H), 6.11(d, J=11.2 Hz, 1H), 6.32(d, J=11.2 Hz, 1H). MS m/z: 556(M$^+$), 248(100%). UV $\lambda_{max}$ nm: 264.

Example 28

Preparation of 1α-(tert-butyldimethylsilyloxy)-3β-hydroxy-20(S)-{(E)-4-hydroxy-4-methyl-2-pentenylthio}-9,10-secopregna-5,7,10(19),16-tetraene Using the crude 1α-(tert-butyldimethylsilyloxy)-3β-hydroxy-20(S)-{(E)-4-hydroxy-4-methyl-2-pentenylthio}pregna-5,7,16-triene (25.8 mg) obtained in Example 22 and ethanol (200 ml), the reaction was performed by the same procedure as in Example 15 (irradiation for 2 minutes and heating under reflux for 2 hours), and then the residue was purified by preparative thin layer chromatography (0.5 mm×1, dichloromethane:ethyl acetate=6:1, developed four times) to give a crude purification product (3.1 mg) and recovered raw materials (10.5 mg). The recovered raw materials (10.5 mg) were irradiated for 2 minutes and heated under reflux for 2 hours again, and the residue was purified by preparative thin layer chromatography (0.5 mm×1, dichloromethane:ethyl acetate=6:1, developed four times) to give a crude purification product (1.8 g), which was combined with the previously obtained one and purified by preparative thin layer chromatography (0.5 mm×1, hexane:ethyl acetate=4:1, developed four times) to give the title compound as a colorless oil (2.0 mg, 6.2%, 2 steps).

IR(neat): 3400, 2930, 1460, 1370, 1250, 1060 cm$^{-1}$. $^1$H NMR δ: 0.09(s, 6H), 0.82(s, 3H), 0.90(s, 9H), 1.32(s, 6H), 1.41(d, J=6.8 Hz, 3H), 2.99–3.19(m, 2H), 3.41(q, J=6.8 Hz, 1H), 4.16–4.28(m, 1H), 4.32–4.43(m, 1H), 4.93(brs, 1H), 5.27(brs, 1H), 5.58(brs, 1H), 5.10–5.78(m, 2H), 6.10(d, J=11.2 Hz, 1H), 6.33 (d, J=11.2 Hz, 1H). MS m/z: 558(M$^+$), 160(100%). UV $\lambda_{max}$ nm: 263.

Example 29

Preparation of 1α,3β-bis(tert-butyldimethylsilyloxy)-20(S)-{(Z)-4-methyl-4-triethylsilyloxy-2-pentenylthio}-9,10-secopregna-5,7,10(19),16-tetraene Using 1α,3β-bis(tert-butyldimethylsilyloxy)-20(S)-{(Z)-4-methyl-4-triethylsilyloxy-2-pentenylthio}pregna-5,7,16-triene (66.1 mg, 0.0839 mol) and ethanol (200 ml), the reaction was performed by the same procedure as in Example 15 (irradiation for 3 minutes and heating under reflux for 2 hours), and then the residue was purified by preparative thin layer chromatography (0.5 mm×3, hexane:dichloromethane=4:1, developed twice) to give 20.9 mg of a compound, which was directly used in the subsequent reaction because it was difficult to separate from raw materials.

Example 30

Preparation of 1α-(tert-butyldimethylsilyloxy)-3β-hydroxy-20(S)-(4-ethyl-4-hydroxy-2-hexynylthio)-9,10-secopregna-5,7,10(19),16-tetraene Using 1α-(tert-butyldimethylsilyloxy)-3β-hydroxy-20 (S)-(4-ethyl-4-hydroxy-2-hexynylthio)pregna-5,7,16-triene (21.9 mg, 0.0374 mmol) and ethanol (200 ml), the reaction was performed by the same procedure as in Example 15 (irradiation for 3.45 minutes and heating under reflux for 1.5 hours), and then the residue was purified by preparative thin layer chromatography (0.5 mm×1, dichloromethane:ethyl acetate=6:1, developed twice, then 0.5 mm×1, hexane:ethyl acetate=3:1, developed four times) to give the title compound as a colorless oil (1.8 mg, 8.2%).

IR(neat): 3400, 2930, 2850, 1460, 1370, 1250, 1060 cm$^{-1}$. $^1$H NMR δ: 0.09(s, 3H), 0.81(s, 3H), 0.89(s, 9H), 1.03(t, J=7.3 Hz, 6H), 1.45(d, J=6.8 Hz, 3H), 1.67(q, J=7.3 Hz, 4H), 3.20(d, J=16.8 Hz, 1H), 3.23(d, J=16.8 Hz, 1H), 3.67(q, J=6.8 Hz, 1H), 4.14–4.28(m, 1H), 4.32–4.43(m, 1H), 4.93 (brs, 1H), 5.27(brs, 1H), 5.63(brs, 1H), 6.10(d, J=11.2 Hz, 1H), 6.32(d, J=11.2 Hz, 1H). MS m/z: 584(W), 248(100%). UV $\lambda_{max}$ nm: 264.

Example 31

Preparation of 1α-(tert-butyldimethylsilyloxy)-3β-hydroxy-20(S)-{(E)-4-ethyl-4-hydroxy-2-hexenylthio}-9,10-secopregna-5,7,10(19),16-tetraene Using 1α-(tert-butyldimethylsilyloxy)-3β-hydroxy-20 (S)-{(E)-4-ethyl-4-hydroxy-2-hexenylthio}pregna-5,7,16-triene (26.3 mg, 0.0448 mmol) and ethanol (200 ml), the reaction was performed by the same procedure as in Example (irradiation for 3 minutes and heating under reflux for 1.5 hours), and then the residue was purified by preparative thin layer chromatography (0.5 mm×1, dichloromethane:ethyl acetate=6:1, developed three times, then 0.5 mm×1, hexane:ethyl acetate=3:1, developed three times) to give the title compound as a colorless oil (2.1 mg, 8.0%).

IR(neat): 3400, 2930, 2850, 1460, 1375, 1255, 1060 cm$^{-1}$. $^1$H NMR δ: 0.09(s, 6H), 0.82(s, 3H), 0.84–0.98(m, 15H), 1.41(d, J=6.8 Hz, 3H), 1.54(q, J=7.3 Hz, 4H), 3.07–3.18(m, 2H), 3.42(g, J=6.8 Hz, 1H), 4.15–4.29(m, 1H), 4.33–4.44(m, 1H), 4.93(brs, 1H), 5.27(brs, 1H), 5.44–5.76(m, 3H), 6.10(d, J=11.2 Hz, 1H), 6.32(d, J=11.2 Hz, 1H). MS m/z: 586(M$^+$), 426(100%). UV λ$_{max}$ nm: 263.

Example 32
Preparation of 1α-(tert-butyldimethylsilyloxy)-3β-hydroxy-20(S)-{(Z)-4-ethyl-4-triethylsilyloxy-2-hexenylthio}-9,10-secopregna-5,7,10(19),16-tetraene Using 1α-(tert-butyldimethylsilyloxy)-3β-hydroxy-20 (S)-{(Z)-4-ethyl-4-triethylsilyloxy-2-hexenylthio}pregna-5, 7,16-triene (23.7 mg, 0.0338 mmol) and ethanol (200 ml), the reaction was performed by the same procedure as in Example 15 (irradiation for 3.5 minutes and heating under reflux for 1.5 hours), and then the residue was purified by preparative thin layer chromatography (0.5 mm×1, dichloromethane:ethyl acetate=6:1, developed three times) to give the title compound as a colorless oil (1.3 mg, 5.5%).

IR(neat): 3400, 2925, 2850, 1460, 1370, 1250, 1050 cm$^{-1}$. $^1$H NMR δ: 0.09(s, 6H), 0.62(q, J=7.5 Hz, 6H), 0.76–1.05 (m, 27H), 1.43(d, J=6.8 Hz, 3H), 1.56(q, J=7.5 Hz, 4H), 3.28–3.60(m, 3H), 4.16–4.29(m, 1H), 4.32–4.43(m, 1H), 4.93(brs, 1H), 5.18–5.30(m, 2H), 5.32–5.55(m, 1H), 5.59 (brs, 1H), 6.11(d, J=11.2 Hz, 1H), 6.32(d, J=11.2 Hz, 1H). MS m/z: 700(M$^+$), 202(100%). UV λ$_{max}$ nm: 263.

Example 33
Preparation of 1α,3β-dihydroxy-20(S)-(4-hydroxy-4-methyl-2-pentynylthio}-9,10-secopregna-5,7,10(19),16-tetraene To a solution of 1α-(tert-butyldimethylsilyloxy)-3β-hydroxy-20(S)-(4-hydroxy-4-methyl-2-pentynylthio)- 9,10-secopregna-5,7,10(19),16-tetraene (3.4 mg, 0.00611 mmol) in tetrahydrofuran (2 ml) was added 1M tetra-n-butylammonium fluoride solution in tetrahydrofuran (1 ml), and the mixed solution was reacted at room temperature for 13 hours. The reaction solution was diluted with ethyl acetate and washed with ice-cooled 0.5 N hydrochloric acid, saturated aqueous sodium bicarbonate solution and brine successively, and the organic layer was dried over magnesium sulfate, then the solvent was removed under reduced pressure. The resulting residue was purified by preparative thin layer chromatography (0.25 mm×1, hexane:ethyl acetate:ethanol=12:8:1, developed three times) to give the title compound as a colorless oil (0.653 mg, 24%).

IR(neat): 3400, 2930, 1450, 1370, 1250, 1160, 1050 cm$^{-1}$. $^1$H NMR δ: 0.84(s, 3H), 1.45(d, J=7.3 Hz, 3H), 1.51(s, 6H), 3.17(d, J=16.6 Hz, 1H), 3.20(d, J=16.6 Hz, 1H), 3.66(q, J=7.3 Hz, 1H), 4.28–4.31(m, 1H), 4.38–4.49(m, 1H), 5.01 (brs, 1H), 5.34(brs, 1H), 5.65(brs, 1H), 6.10(d, J=11.2 Hz, 1H), 6.37(d, J=11.2 Hz, 1H). MS m/z: 442(M$^+$), 311(100%). UV λ$_{max}$ nm: 263.

Example 34
Preparation of 1α,3β-dihydroxy-20(S)-{(E)-4-hydroxy-4-methyl-2-pentenylthio}-9,10-secopregna-5,7,10(19),16-tetraene By the same procedure as in Example 33, 1α-(tert-butyldimethylsilyloxy)-3β-hydroxy-20(S)-{(E)-4-hydroxy-4-methyl-2-pentenylthio}-9,10-secopregna-5,7,10(19),16-tetraene (2.0 mg, 0.00358 mmol), tetrahydrofuran (1 ml) and 1M tetra-n-butylammonium fluoride solution in tetrahydrofuran (0.5 ml) were reacted (3 days) and worked up, and then the residue was purified by preparative thin layer chromatography (0.25 mm×1, hexane:ethyl acetate:ethanol=12:8:1, developed three times) to give the title compound as a colorless oil (0.744 mg, 47%).

IR(neat): 3400, 2920, 1460, 1370, 1060 cm$^{-1}$. $^1$H NMR δ: 0.88(s, 3H), 1.32(s, 6H), 1.41(d, J=6.8 Hz, 3H), 2.96–3.20 (m, 2H), 3.40(d, J=6.8 Hz, 1H), 4.17–4.32(m, 1H), 4.39–4.49(m, 1H), 5.02(brs, 1H), 5.34(brs, 1H), 5.60–5.77 (m, 2H), 6.10(d, J=11.2 Hz, 1H), 6.37(d, J=11.2 Hz, 1H). MS m/z: 426(M$^+$-H$_2$O), 105(100%). UV λ$_{max}$ nm: 264.

Example 35
Preparation of 1α,3β-dihydroxy-20(S)-{(Z)-4-hydroxy-4-methyl-2-pentenylthio}-9,10-secopregna-5,7,10(19),16-tetraene By the same procedure as in Example 33, the crude 1α,3β-bis(tert-butyldimethylsilyloxy)-20(S)-{(Z)-4-methyl-4-triethylsilyloxy-2-pentenylthio}-9,10-secopregna-5,7,10(19),16-tetraene (20.9 mg) obtained in Example 29, tetrahydrofuran (3 ml) and 1M tetra-n-butylammonium fluoride solution in tetrahydrofuran (2 ml) were reacted (40 hours) and worked up, and then the residue was purified by preparative thin layer chromatography (0.5 mm×1, hexane:ethyl acetate:ethanol=12:8:1, developed five times) to give the title compound as a colorless oil (1.67 mg, 14%, 2 steps).

IR(neat): 3400, 2930, 1450, 1370, 1210, 1150, 1060 cm$^{-1}$. $^1$H NMR δ: 0.84(s, 3H), 1.36(s, 6H), 1.44(d, Z=7.3 Hz, 3H), 3.34(dd, J=12.2, 6.8 Hz, 1H), 3.62–3.77(m, 2H), 4.17–4.32 (m, 1H), 4.38–4.50(m, 1H), 5.01(brs, 1H), 5.34(brs, 1H), 5.35–5.58(m, 2H), 5.60(brs, 1H), 6.10(d, J=11.2 Hz, 1H), 6.37(d, J=11.2 Hz, 1H). MS m/z: 444(M$^+$), 312(100%). UV λ$_{max}$ nm: 264.

Example 36
Preparation of 1α,3β-dihydroxy-20(S)-(4-ethyl-4-hydroxy-2-hexynylthio)-9,10-secopregna-5,7,10(19),16-tetraene By the same procedure as in Example 33, 1α-(tert-butyldimethylsilyloxy)-3β-hydroxy-20(S)-(4-ethyl-4-hydroxy-2-hexynylthio)-9,10-secopregna-5,7,10(19),16-tetraene (1.8 mg, 0.00308 mmol), tetrahydrofuran (2 ml) and 1M tetra-n-butylammonium fluoride solution in tetrahydrofuran (2 ml) were reacted (40 hours) and worked up, and then the residue was purified by preparative thin layer chromatography (0.25 mm×1, hexane:ethyl acetate:ethanol 12:8:1, developed three times) to give the title compound as a colorless oil (0.699 mg, 48%).

IR(neat): 3400, 2930, 1450, 1370, 1230, 1150, 1060 cm$^{-1}$. $^1$H NMR δ: 0.82(s, 3H), 1.02(t, J=7.3 Hz, 6H), 1.44(d, J=6.8 Hz, 3H), 1.65(q, J=7.3 Hz, 4H), 3.28(d, J=16.7 Hz, 1H), 3.32(d, J=16.7 Hz, 1H), 3.66(q, J=6.8 Hz, 1H), 4.16–4.31(m, 1H), 4.36–3.52(m, 1H), 4.99(brs, 1H), 5.32(brs, 1H), 5.61 (brs, 1H), 6.07(d, J=11.2 Hz, 1H), 6.35(d, J=11.2 Hz, 1H). MS m/z: 452(M$^+$-H$_2$O), 91(100%). UV λ$_{max}$ nm: 264.

Example 37
Preparation of 1α,3β-dihydroxy-20(S)-{(E)-4-ethyl-4-hydroxy-2-hexenylthio}-9,10-secopregna-5,7,10(19),16-tetraene By the same procedure as in Example 33, 1α-(tert-butyldimethylsilyloxy)-3β-hydroxy-20(S)-{(E)-4-ethyl-4-hydroxy-2-hexenylthio}-9,10-secopregna-5,7,10(19),16-tetraene (1.9 mg, 0.00324 mmol), tetrahydrofuran (2 ml) and 1M tetra-n-butylammonium fluoride solution in tetrahydrofuran (2 ml) were reacted (40 hours) and worked up, and then the residue was purified by preparative thin layer chromatography (0.25 mm×1, hexane:ethyl acetate:ethanol= 12:8:1, developed three times) to give the title compound as a colorless oil (0.748 mg, 49%).

IR(neat): 3400, 2920, 1450, 1370, 1270, 1050 cm$^{-1}$. $^1$H NMR δ: 0.86(t, J=7.3 Hz, 6H), 0.88(s, 3H), 1.41(d, J=6.8 Hz, 3H), 1.53(q, J=7.3 Hz, 4H), 3.07–3.17(m, 2H), 3.42(q, J=6.8 Hz, 1H), 4.17–4.29(m, 1H), 4.38–4.50(m, 1H), 5.02 (brs, 1H), 5.34(brs, 1H), 5.43–5.80(m, 3H), 6.10(d, J=11.2 Hz, 1H), 6.38(d, J=11.2 Hz, 1H). MS m/z: 454(M$^+$-H$_2$O), 161(100%). UV λ$_{max}$ nm: 264.

Example 38
Preparation of 1α,3β-dihydroxy-20(S)-{(Z)-4-ethyl-4-hydroxy-2-hexenylthio}-9,10-secopregna-5,7,10(19),16-tetraene By the same procedure as in Example 33, 1α-(tert-butyldimethylsilyloxy)-3β-hydroxy-20(S)-{(Z)-4-ethyl-4-triethylsilyloxy-2-hexenylthio}-9,10-secopregna-5,7,10(19),16-tetraene (1.2 mg, 0.00171 mmol), tetrahydrofuran (2 ml) and 1M tetra-n-butylammonium fluoride solution in tetrahydrofuran (2 ml) were reacted (40 hours) and worked up, and then the residue was purified by preparative thin layer chromatography (0.25 mm×1, hexane:ethyl acetate:ethanol=12:8:1, developed twice) to give the title compound as a colorless oil (0.357 mg, 44%).

IR(neat): 3400, 2920, 1450, 1370, 1060 cm$^{-1}$. $^1$H NMR δ: 0.84(s, 3H), 0.91(t, J=7.5 Hz, 6H), 1.44(d, J=6.8 Hz, 3H), 1.57(g, J=7.5 Hz, 4H), 3.27–3.58(m, 3H), 4.17–4.31(m, 1H), 4.40–4.52(m, 1H), 5.01(brs, 1H), 5.23–5.37(m, 2H), 5.44–5.70(m, 2H), 6.10(d, J=11.2 Hz, 1H), 6.37(d, J=11.2 Hz, 1H). MS m/z: 454(M$^+$-H$_2$O), 312(100%). UV λ$_{max}$ nm: 263.

Example 39
Preparation of 1α,3β-bis(tert-butyldimethylsilyloxy)-16α-hydroxy-9,10-secopregna-5,7,10(19),17(E)-tetraene Using 1α,3β-bis(tert-butyldimethylsilyloxy)-16α-hydroxypregna-5,7,17(E)-triene (103 mg, 0.184 mmol) and ethanol (200 ml), the reaction was performed by the same procedure as in Example 15 (irradiation for 5 minutes and heating under reflux for 2 hours), and then the residue was purified by preparative thin layer chromatography (0.5 mm×3, hexane:ethyl acetate=9:1, developed four times, then 0.5 mm×2, hexane:ethyl acetate=9:1, developed four times) to give the title compound as a colorless oil (24.1 mg, 23%).

IR(neat): 3350, 2930, 2855, 1460, 1380, 1255, 1080 cm$^{-1}$. $^1$H NMR δ: 0.06(s, 12H), 0.74(s, 3H), 0.88(s, 18H), 1.74(d, J=7.3 Hz, 3H), 4.12–4.28(m, 1H), 4.32–4.52(m, 2H), 4.86(d, J=2.0 Hz, 1H), 5.19(d, J=2.0 Hz, 1H), 5.64(q, J=7.3 Hz, 1H), 6.00(d, J=11.2 Hz, 1H), 6.23(d, J=11.2 Hz, 1H). MS m/z: 558(M$^+$), 248(100%). UV λ$_{max}$ nm: 262.

Example 40
Preparation of 1α,3β-bis(tert-butyldimethylsilyloxy)-20(S)-phenoxycarbonylthio-9,10-secopregna-5,7,10(19),16-tetraene Under the same conditions as in Example 1, 1α,3β-bis(tert-butyldimethylsilyloxy)-16α-hydroxy-9,10-secopregna-5,7,10(19),17(E)-tetraene (24.0 mg, 0.0430 mmol), dichloromethane (2.5 ml), pyridine (0.0209 ml, 0.258 mmol) and phenyl chlorothionoformate (0.0178 ml, 0.129 mmol) were reacted and worked up, and then the residue was purified by preparative thin layer chromatography (0.5 mm×1, hexane:ethyl acetate=9:1, developed once) to give the title compound as a colorless oil (17.9 mg, 60%).

IR(neat): 2925, 2850, 1730, 1490, 1470, 1255, 1190, 1160, 1100 cm$^{-1}$. $^1$H NMR δ: 0.07(s, 12H), 0.85(s, 3H), 0.88(s, 18H), 1.59(d, J=6.8 Hz, 3H), 4.04–4.28(m, 2H), 4.39(t, J=4.9 Hz, 1H), 4.88(d, J=2.0 Hz, 1H), 5.19(d, J=2.0 Hz, 1H), 5.74(brs, 1H), 6.09(d, J=11.2 Hz, 1H), 6.24(d, J=11.2 Hz, 1H), 7.12–7.44(m, 5H). MS m/z: 694(M$^+$), 248(100%). UV λ$_{max}$ nm: 210, 263.

Example 41
Preparation of 1α,3β-bis(tert-butyldimethylsilyloxy)-20(S)-(3-hydroxy-3-methylbutylthio)-9,10-secopregna-5,7,10(19),16-tetraene Under the same conditions as in Example 3, 1α,3β-bis(tert-butyldimethylsilyloxy)-20(S)-phenoxycarbonylthio-9,10-secopregna-5,7,10(19),16-tetraene (2.0 mg, 0.00288 mmol), 4-bromo-2-methyl-2-butanol (2.4 mg, 0.0144 mmol), tetrahydrofuran (0.25 ml) and 1M KOH solution in methanol (0.25 ml) were reacted and worked up, and then the residue was purified by preparative thin layer chromatography (0.25 mm×1, hexane:ethyl acetate=3:1, developed once) to give the title compound as a colorless oil (1.5 mg, 79%).

IR(neat): 3400, 2920, 2850, 1460, 1360, 1250, 1080 cm$^{-1}$. $^1$H NMR δ: 0.07(s, 12H), 0.81(s, 3H), 0.87(s, 9H), 0.88(s, 9H), 1.23(s, 6H), 1.42(d, J=6.8 Hz, 3H), 3.49(q, J=6.8 Hz, 1H), 4.11–4.24(m, 1H), 4.26–4.31(m, 1H), 4.84(brs, 1H), 5.19(brs, 1H), 5.60(brs, 1H), 6.10(d, J=11.2 Hz, 1H), 6.24(d, J=11.2 Hz, 1H). MS m/z: 660(M$^+$), 248(100%). UV λ$_{max}$ nm: 263.

Example 42
Preparation of 1α,3β-dihydroxy-20(S)-(3-hydroxy-3-methylbutylthio)-9,10-secopregna-5,7,10(19),16-tetraene By the same procedure as in Example 9, 1α,3β-bis(tert-butyldimethylsilyloxy)-20(S)-(3-hydroxy-3-methylbutylthio)-9,10-secopregna-5,7,10(19),16-tetraene (1.5 mg, 0.00227 mmol), tetrahydrofuran (1 ml) and 1M tetra-n-butylammonium fluoride solution in tetrahydrofuran (0.5 ml) were reacted (1.5 hours) and worked up, and then the residue was purified by preparative thin layer chromatography (0.25 mm×1, hexane:ethyl acetate:ethanol=12:8:1, developed three times) to give the title compound as a colorless oil (0.511 mg, 52%). Each spectrum of the compound obtained here was consistent with that of the compound obtained in Example 15.

Example 43
Preparation of 1α,3β-bis(tert-butyldimethylsilyloxy)-16-oxopregna-5,7,17(E)-triene To a solution of 1α,3β-bis(tert-butyldimethylsilyloxy)-16α-hydroxypregna-5,7,17(E)-triene (2.01 g, 3.60 mmol) in chloroform (150 ml) was added manganese dioxide (40 g), and the mixed solution was reacted for 2 hours under ultrasonication. The reaction solution was filtered and the filtrate was concentrated, and then the residue was purified by column chromatography (hexane:dichloromethane:ethyl acetate=18:2:1) to give the title compound as a colorless solid (1.45 g, 73%).

IR(KBr): 2950, 2850, 17;30, 1650, 1460, 1380, 1255, 1100 cm$^{-1}$. $^1$H NMR δ: 0.06(s, 3H), 0.07(s, 3H), 0.08(s, 3H), 0.12(s, 3H), 0.89(s, 18H), 0.97(s, 3H), 0.99(s, 3H), 1.88(d, J=7.3 Hz, 3H), 3.73(brs, 1H), 3.96–4.16(m, 1H), 5.30–5.39 (m, 1H), 5.56–5.65(m, 1H), 6.56(q, J=7.3 Hz, 1H). MS m/z: 556(M$^+$), 367(100%). UV λ$_{max}$ nm: 242, 258, 270, 281, 293.

Example 44
Preparation of 1α,3β-bis(tert-butyldimethylsilyloxy)-16β-hydroxypregna-5,7,17(E)-triene To a solution of 1α,3β-bis(tert-butyldimethylsilyloxy)-16-oxopregna-5,7,17(E)-triene (1.45 g, 2.60 mmol) and cerium (III) chloride heptahydrate (1.45 g, 3.90 mmol) in methanol (20 ml) and tetrahydrofuran (80 ml) cooled at 0° C. was added sodium borohydride (490 mg, 13.0 mmol) by portions. The reaction solution was stirred at room temperature for one hour, then concentrated under reduced pressure, and the residue was taken into water and extracted with ethyl acetate. The organic layer was washed with brine and then dried over magnesium sulfate, and the solvent was distilled off under reduced pressure. The resulting residue was purified by column chromatography (hexane:ethyl acetate=10:1) to give the title compound as a colorless solid (1.29 g, 89%) and 1α,3β-bis(tert-butyldimethylsilyloxy)-16α-hydroxypregna-5,7,17(E)-triene (85 mg, 5.8%).

Title compound: IR(KBr): 3300, 2950, 2850, 1460, 1370, 1245, 1100, 1000 cm$^{-1}$. $^1$H NMR δ: 0.05(s, 3H), 0.07(s, 6H), 0.11(s, 3H), 0.88(s, 18H), 0.93(s, 3H), 1.00(s, 3H), 1.76(dd, J=7.3, 2.0 Hz, 3H), 3.71(brs, 1H), 3.93–4.16(m, 1H), 4.49(t, J=7.8 Hz, 1H), 5.33–5.42(m, 1H), 5.47–5.64(m, 2H). MS m/z: 558(M$^+$), 369(100%). UV λ$_{max}$ nm: 270, 281, 293.

Example 45

Preparation of 1α,3β-bis(tert-butyldimethylsilyloxy)-16β-hydroxy-9,10-secopregna-5,7,10(19),17(E)-tetraene Using 1α,3β-bis(tert-butyldimethylsilyloxy)-16β-hydroxypregna-5,7,17(E)-triene (115 mg, 0.205 mmol) and ethanol (200 ml), the reaction was performed by the same procedure as in Example 15 (irradiation for 5.5 minutes and heating under reflux for 2 hours), and then the residue was purified by preparative thin layer chromatography (0.5 mm×3, hexane:ethyl acetate=8:1, developed three times) to give the title compound as a colorless oil (27.0 mg, 23%).

IR(neat): 3400, 2950, 2850, 1470, 1370, 1250, 1075 cm$^{-1}$. $^1$H NMR δ: 0.06(s, 6H), 0.07(s, 6H), 0.88(s, 18H), 0.91(s, 3H), 1.74(dd, J=6.8, 1.5 Hz, 3H), 4.13–4.29(m, 1H), 4.32–4.55(m, 2H), 4.87(d, J=1.9 Hz, 1H), 5.20(d, J=1.9 Hz, 1H), 5.57(dq, J=6.8, 1.5 Hz, 1H), 6.04(d, J=11.2 Hz, 1H), 6.21(d, J=11.2 Hz, 1H). MS m/z: 558(M$^+$), 427(100%). UV λ$_{max}$ nm: 263.

Example 46

Preparation of 1α,3β-bis(tert-butyldimethylsilyloxy)-20(R)-phenoxycarbonylthio-9,10-secopregna-5,7,10(19),16-tetraene Under the same conditions as in Example 1, 1α,3β-bis(tert-butyldimethylsilyloxy)-16β-hydroxy-9,10-secopregna-5,7,10(19),17(E)-tetraene (53.1 mg, 0.0950 mmol), dichloromethane (5 ml), pyridine (0.0461 ml, 0.570 mmol) and phenyl chlorothionoformate (0.0394 ml, 0.285 mmol) were reacted and worked up, and then the residue was purified by preparative thin layer chromatography (0.5 mm×2, hexane ethyl acetate=8:1, developed once) to give the title compound as a colorless oil (55.4 mg, 84%).

IR(neat): 2930, 2850, 1730, 1490, 1470, 1370, 1255, 1190, 1160, 1100, 1010 cm$^{-1}$. $^1$H NMR δ: 0.06(s, 12H), 0.73(s, 3H), 0.87(s, 9H), 0.88(s, 9H), 1.61(d, J=6.8 Hz, 3H), 4.08(q, J=6.8 Hz, 1H), 4.12–4.28(m, 1H), 4.32–4.44(m, 1H), 4.88(d, J=1.9 Hz, 1H), 5.19(d, J=1.9 Hz, 1H), 5.72(brs, 1H), 6.10(d, J=11.2 Hz, 1H), 6.24(d, J=11.2 Hz, 1H), 7.07–7.48 (m, 5H). MS m/z: 694 (M$^+$), 248 (100%). UV λ$_{max}$ nm: 215, 263.

Example 47

Preparation of 1α,3β-dihydroxy-20(R)-(3-hydroxy-3-methylbutylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (3.3 mg, 0.00475 mmol), 4-bromo-2-methyl-2-butanol (4.0 mg, 0.0238 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 3.6 mg of a product, to which were added tetrahydrofuran (1 ml) and 1M tetra-n-butylammonium fluoride solution in tetrahydrofuran (0.3 ml). By the same procedure as in Example 9, the mixed solution was reacted (1.5 hours) and worked up, and then the residue was purified by preparative thin layer chromatography (0.25 mm×1, hexane:ethyl acetate:ethanol 12:8:1, developed three times) to give the title compound as a colorless oil (1.15 mg, 56%).

IR(neat): 3400, 2920, 1450, 1370, 1200, 1060 cm$^{-1}$. $^1$H NMR δ: 0.74(s, 3H), 1.24(s, 6H), 1.47(d, J=6.8 Hz, 3H), 3.40(q, J=6.8 Hz, 1H), 4.14–4.29(m, 1H), 4.34–4.48(m, 1H), 5.01(brs, 1H), 5.34(brs, 1H), 5.29(brs, 1H), 6.10(d, J=11.2 Hz, 1H), 6.37(d, Z=11.2 Hz, 1H). MS m/z: 432(M$^+$), 312 (100%). UV λ$_{max}$ nm: 263.

Example 48

Preparation of 1α,3β-dihydroxy-20(R)-(4-hydroxy-4-methylpentylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (3.9 mg, 0.00561 mmol), 1-bromo-4-methyl-4-triethylsilyloxypentane (8.3 mg, 0.0281 mmol), tetrahydrofuran (0.5 ml) and 1M KOH solution in methanol (0.5 ml) were reacted and worked up, and then the residue was purified by preparative thin layer chromatography (0.25 mm×1, hexane:dichloromethane:ethyl acetate=160:40:1, developed once) to give 3.1 mg of a product, to which were added tetrahydrofuran (1 ml) and 1M tetra-n-butylammonium fluoride solution in tetrahydrofuran (0.5 ml). By the same procedure as in Example 9, the mixed solution was reacted (1.5 hours) and worked up, and then the residue was purified by preparative thin layer chromatography (0.25 mm×1, hexane:ethyl acetate:ethanol= 12:8:1, developed twice) to give the title compound as a colorless oil (0.614 mg, 24%).

IR(neat): 3400, 2920, 1450, 1370, 1270, 1200, 1050 cm$^{-1}$. $^1$H NMR δ: 0.74(s, 3H), 1.22(s, 6H), 1.45(d, J=6.9 Hz, 3H), 3.36(g, J=6.9 Hz, 1H), 4.18–4.30(m, 1H), 4.39–4.50(m, 1H), 5.01(brs, 1H), 5.34(brs, 1H), 5.57(brs, 1H), 6.11(d, J=11.2 Hz, 1H), 6.37(d, J=11.2 Hz, 1H). MS m/z: 428(M$^+$-H$_2$O), 312(100%). UV λ$_{max}$ nm: 264.

Example 49

Preparation of 1α,3β-dihydroxy-20(R)-(5-hydroxy-5-methylhexylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (3.8 mg, 0.00547 mmol), 6-bromo-2-methyl-2-hexanol (5.3 mg, 0.0274 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 3.1 mg of a product, to which were added tetrahydrofuran (1 ml) and 1M tetra-n-butylammonium fluoride solution in tetrahydrofuran (0.3 ml). By the same procedure as in Example 9, the mixed solution was reacted (1.5 hours) and worked up, and then the residue was purified by preparative thin layer chromatography (0.25 mm×1, hexane:ethyl acetate:ethanol=12:8:1, developed three times) to give the title compound as a colorless oil (1.34 mg, 60%).

IR(neat): 3400, 2920, 1450, 1370, 1200, 1060 cm$^{-1}$. $^1$H NMR δ: 0.73(s, 3H), 1.21(s, 6H), 1.45(d, J=6.8 Hz, 3H), 3.34(q, J=6.8 Hz, 1H), 4.28–4.32(m, 1H), 4.38–4.51(m, 1H), 5.01(brs, 1H), 5.34(brs, 1H), 5.56(brs, 1H), 6.10(d, J=11.2 Hz, 1H), 6.38(d, J=11.2 Hz, 1H). MS m/z: 442($M^+$-$H_2O$), 312(100%). UV $\lambda_{max}$ nm: 264.

Example 50

Preparation of 1α,3β-dihydroxy-20(R)-(2-hydroxy-2-methylpropylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (3.9 mg, 0.00561 mmol), isobutylene oxide (2.0 mg, 0.0281 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 2.2 mg of a product, to which were added tetrahydrofuran (1 ml) and 1M tetra-n-butylammonium fluoride solution in tetrahydrofuran (0.3 ml). By the same procedure as in Example 9, the mixed solution was reacted (1.5 hours) and worked up, and then the residue was purified by preparative thin layer chromatography (0.25 mm×1, hexane:ethyl acetate:ethanol=12:8:1, developed three times) to give the title compound as a colorless oil (0.929 mg, 40%).

IR(neat): 3400, 2920, 1450, 1370, 1200, 1145, 1055 $cm^{-1}$. $^1$H NMR δ: 0.73(s, 3H), 1.26(s, 3H), 1.27(s, 3H), 1.46(d, J=6.9 Hz, 3H), 3.39(q, J=6.9 Hz, 1H), 4.18–4.29(m, 1H), 4.41–4.50(m, 1H), 5.01(brs, 1H), 5.34(brs, 1H), 5.60(brs, 1H), 6.10(d, J=11.2 Hz, 1H), 6.37(d, J=11.2 Hz, 1H). MS m/z: 418($M^+$), 91(100%). UV $\lambda_{max}$ nm: 264.

Example 51

Preparation of 1α,3β-dihydroxy-20(R)-(3-ethyl-3-hydroxypentylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (4.0 mg, 0.00575 mmol), 5-bromo-3-ethyl-3-pentanol (5.6 mg, 0.0288 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 3.0 mg of a product, to which were added tetrahydrofuran (1 ml) and 1M tetra-n-butylammonium fluoride solution in tetrahydrofuran (0.3 ml). By the same procedure as in Example 9, the mixed solution was reacted (1.5 hours) and worked up, and then the residue was purified by preparative thin layer chromatography (0.25 mm×1, hexane:ethyl acetate:ethanol=12:8:1, developed three times) to give the title compound as a colorless oil (1.48 mg, 56%).

IR(neat): 3400, 2920, 1465, 1370, 1200, 1060 $cm^{-1}$. $^1$H NMR δ: 0.74(s, 3H), 0.86(t, J=7.4 Hz, 6H), 1.40–1.53(m, 7H), 3.39(q, J=6.9 Hz, 1H), 4.18–4.30(m, 1H), 4.38–4.51(m, 1H), 5.01(brs, 1H), 5.34(brs, 1H), 5.58(brs, 1H), 6.10(d, J=11.2 Hz, 1H), 6.37(d, J=11.2 Hz, 1H). MS m/z: 460($M^+$), 312(100%). UV $\lambda_{max}$ nm: 264.

Example 52

Preparation of 1α,3β-dihydroxy-20(R)-(4-ethyl-4-hydroxyhexylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (5.0 mg, 0.00719 mmol), 6-bromo-3-ethyl-3-hexanol (7.5 mg, 0.0360 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 4.2 mg of a product, to which were added tetrahydrofuran (0.5 ml) and 1M tetra-n-butylammonium fluoride solution in tetrahydrofuran (0.3 ml). By the same procedure as in Example 9, the mixed solution was reacted (1.5 hours) and worked up, and then the residue was purified by preparative thin layer chromatography (0.25 mm×1, hexane:ethyl acetate:ethanol=12:8:1, developed three times) to give the title compound as a colorless oil (1.14 mg, 33%).

IR(neat): 3400, 2920, 1455, 1370, 1250, 1140, 1050 $cm^{-1}$. $^1$H NMR δ: 0.74(s, 3H), 0.92(t, J=6.9 Hz, 6H), 3.39(q, J=6.8 Hz, 1H), 4.18–4.32(m, 1H), 4.39–4.52(m, 1H), 5.01(brs, 1H), 5.34(brs, 1H), 5.58(brs, 1H), 6.11(d, J=11.2 Hz, 1H), 6.38(d, J=11.2 Hz, 1H). MS m/z: 456($M^+$-$H_2O$), 312(100%). UV $\lambda_{max}$ nm: 264.

Example 53

Preparation of 1α,3β-dihydroxy-20(R)-(4-hydroxy-4-methyl-2-pentynylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (4.3 mg, 0.00619 mmol), 5-bromo-2-methyl-3-pentyn-2-ol (5.5 mg, 0.0309 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 3.3 mg of a product, to which were added tetrahydrofuran (0.5 ml) and 1M tetra-n-butylammonium fluoride solution in tetrahydrofuran (0.3 ml). By the same procedure as in Example 33, the mixed solution was reacted (2 days) and worked up, and then the residue was purified by preparative thin layer chromatography (0.25 mm×1, hexane:ethyl acetate:ethanol=12:8:1, developed three times) to give the title compound as a colorless oil (1.17 mg, 43%).

IR(neat): 3400, 2920, 1455, 1370, 1250, 1170, 1055 $cm^{-1}$. $^1$H NMR δ: 0.74(s, 3H), 1.45(d, J=6.8 Hz, 3H), 1.48(s, 6H), 3.20(d, J=16.6 Hz, 1H), 3.30(d, J=16.6 Hz, 1H), 3.56(q, J=6.8 Hz, 1H), 4.18–4.32(m, 1H), 4.37–4.52(m, 1H), 5.01(brs, 1H), 5.34(brs, 1H), 5.64(brs, 1H), 6.10(d, J=11.2 Hz, 1H), 6.38(d, J=11.2 Hz, 1H). MS m/z: 442 ($M^+$), 312 (100%). UV $\lambda_{max}$ nm: 264.

Example 54

Preparation of 1α,3β-dihydroxy-20(R)-{(E)-4-hydroxy-4-methyl-2-pentenylthio}-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (5.0 mg, 0.00719 mmol), (E)-5-bromo-2-methyl-3-penten-2-ol (6.4 mg, 0.0360 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 4.8 mg of a product, to which were added tetrahydrofuran (0.5 ml) and 1M tetra-n-butylammonium fluoride solution in tetrahydrofuran (0.3 ml). By the same procedure as in Example 33, the mixed solution was reacted (2 days) and worked up, and then the residue was purified by preparative thin layer chromatography (0.25 mm×1, hexane:ethyl acetate:ethanol=12:8:1, developed twice) to give the title compound as a colorless oil (1.88 mg, 59%).

IR(neat): 3400, 2920, 1450, 1370, 1205, 1140, 1050 $cm^{-1}$. $^1$H NMR δ: 0.73(s, 3H), 1.33(s, 6H), 1.44(d, J=6.8 Hz, 3H), 3.02–3.22(m, 2H), 3.33(q, J=6.8 Hz, 1H), 4.16–4.31(m, 1H), 4.39–4.52(m, 1H), 5.01(brs, 1H), 5.34(brs, 1H), 5.59(brs, 1H), 5.63–5.79(m, 2H), 6.10(d, J=11.2 Hz, 1H), 6.38(d, J=11.2 Hz, 1H). MS m/z: 426 (M$^+$-H$_2$O), 352(100%). UV $\lambda_{max}$ nm: 264.

Example 55
Preparation of 1α,3β-dihydroxy-20(R)-{(Z)-4-hydroxy-4-methyl-2-pentenylthio}-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (4.8 mg, 0.00690 mmol), (Z)-1-bromo-4-methyl-4-triethylsilyloxy-2-pentene (10.1 mg, 0.0345 mmol), tetrahydrofuran (0.5 ml) and 1M KOH solution in methanol (0.5 ml) were reacted and worked up, and then the residue was purified by preparative thin layer chromatography (0.25 mm×1, hexane:dichloromethane:ethyl acetate=160:40:1, developed once) to give 4.2 mg of a product, to which were added tetrahydrofuran (0.5 ml) and 1M tetra-n-butylammonium fluoride solution in tetrahydrofuran (0.3 ml). By the same procedure as in Example 33, the mixed solution was reacted (2 days) and worked up, and then the residue was purified by preparative thin layer chromatography (0.25 mm×1, hexane:ethyl acetate:ethanol=12:8:1, developed twice) to give the title compound as a colorless oil (1.87 mg, 61%).

IR(neat): 3400, 2920, 1450, 1370, 1200, 1140, 1055 cm$^{-1}$. $^1$H NMR δ: 0.73(s, 3H), 1.36(s, 6H), 1.48(d, J=6.9 Hz, 3H), 3.32–3.61(m, 3H), 4.17–4.33(m, 1H), 4.37–4.52(m, 1H), 5.01(brs, 1H), 5.34(brs, 1H), 5.37–5.63(m, 3H), 6.10(d, J=11.2 Hz, 1H), 6.37(d, J=11.2 Hz, 1H). MS m/z: 444(M$^+$), 294(100%). UV $\lambda_{max}$ nm: 264.

Example 56
Preparation of 1α,3β-dihydroxy-20(R)-(4-ethyl-4-hydroxy-2-hexynylthio)-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (4.3 mg, 0.00619 mmol), 6-bromo-3-ethyl-4-hexyn-3-ol (6.4 mg, 0.0309 mmol), tetrahydrofuran (0.5 ml) and 1M KOH solution in methanol (0.5 ml) were reacted and worked up, and then the residue was purified by preparative thin layer chromatography (0.25 mm×1, hexane ethyl acetate=3:1, developed once) to give 4.2 mg of a product, to which were added tetrahydrofuran (0.5 ml) and 1M tetra-n-butylammonium fluoride solution in tetrahydrofuran (0.3 ml). By the same procedure as in Example 33, the mixed solution was reacted (2 days) and worked up, and then the residue was purified by preparative thin layer chromatography (0.25 mm×1, hexane:ethyl acetate:ethanol=12:8:1, developed three times) to give the title compound as a colorless oil (1.17 mg, 43%).

IR(neat): 3400, 2920, 1455, 1370, 1240, 1150, 1055 cm$^{-1}$. $^1$H NMR δ: 0.74(s, 3H), 1.03(t, J=7.3 Hz, 6H), 1.49(d, J=6.8 Hz, 3H), 1.66(q, J=7.3 Hz, 4H), 3.23(d, J=16.6 Hz, 1H), 3.29(d, J=16.6 Hz, 1H), 3.59(q, J=6.8 Hz, 1H), 4.18–4.33(m, 1H), 4.39–4.53(m, 1H), 5.01(brs, 1H), 5.34(brs, 1H), 5.64(brs, 1H), 6.11(d, J=11.2 Hz, 1H), 6.34(d, J=11.2 Hz, 1H). MS m/z: 470 (M$^+$), 312 (100%). UV $\lambda_{max}$ nm: 264.

Example 57
Preparation of 1α,3β-dihydroxy-20(R)-{(E)-4-ethyl-4-hydroxy- 2-hexenylthio}-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (5.0 mg, 0.00719 mmol), (E)-6-bromo-3-ethyl-4-hexen-3-ol (7.5 mg, 0.0360 mmol), tetrahydrofuran (0.5 ml) and 1M KOH solution in methanol (0.5 ml) were reacted and worked up, and then the residue was purified by preparative thin layer chromatography (0.25 mm×1, hexane:ethyl acetate=3:1, developed once) to give 4.6 mg of a product, to which were added tetrahydrofuran (0.5 ml) and 1M tetra-n-butylammonium fluoride solution in tetrahydrofuran (0.3 ml). By the same procedure as in Example 33, the mixed solution was reacted (2 days) and worked up, and then the residue was purified by preparative thin layer chromatography (0.25 mm×1, hexane:ethyl acetate:ethanol=12:8:1, developed twice) to give the title compound as a colorless oil (2.40 mg, 71%).

IR(neat): 3400, 2920, 1450, 1370, 1220, 1140, 1055 cm$^{-1}$. $^1$H NMR δ: 0.73(s, 3H), 0.87(t, J=7.3 Hz, 6H), 1.44(d, J=6.8 Hz, 3H), 1.54(q, J=7.3 Hz, 4H), 3.04–3.27(m, 2H), 3.35(q, J=6.8 Hz, 1H), 4.26–4.32(m, 1H), 4.39–4.53(m, 1H), 5.01(brs, 1H), 5.34(brs, 1H), 5.45–5.78(m, 3H), 6.10(d, J=11.2 Hz, 1H), 6.38(d, J=11.2 Hz, 1H). MS m/z: 454(M$^+$-H$_2$O), 380(100%). UV $\lambda_{max}$ nm: 264.

Example 58
Preparation of 1α,3β-dihydroxy-20(R)-{(Z)-4-ethyl-4-hydroxy-2-hexenylthio}-9,10-secopregna-5,7,10(19),16-tetraene Under the same conditions as in Example 3, 1α,3β-bis(tert-butyldimethylsilyloxy)-20(R)-phenoxycarbonylthio-9,10-secopregna-5,7,10(19),16-tetraene (5.0 mg, 0.00719 mmol), (Z)-1-bromo-4-ethyl-4-triethylsilyloxy-2-hexene (11.6 mg, 0.0360 mmol), tetrahydrofuran (0.5 ml) and 1M KOH solution in methanol (0.5 ml) were reacted and worked up, and then the residue was purified by preparative thin layer chromatography (0.25 mm×1, hexane:dichloromethane:ethyl acetate=160:40:1, developed once) to give 4.2 mg of a product, to which were added tetrahydrofuran (0.5 ml) and 1M tetra-n-butylammonium fluoride solution in tetrahydrofuran (0.3 ml). By the same procedure as in Example 33, the mixed solution was reacted (2 days) and worked up, and then the residue was purified by preparative thin layer chromatography (0.25 mm×1, hexane:ethyl acetate:ethanol=12:8:1, developed three times) to give the title compound as a colorless oil (1.74 mg, 51%).

IR(neat): 3400, 2925, 1450, 1365, 1210, 1055 cm$^{-1}$. $^1$H NMR δ: 0.72(s, 3H), 0.91(t, J=7.3 Hz, 6H), 1.48(d, J=6.8 Hz, 3H), 1.52(q, J=7.3 Hz, 4H), 3.32–3.64(m, 3H), 4.16–4.32(m, 1H), 4.39–4.51(m, 1H), 5.01(brs, 1H), 5.25–5.37(m, 2H), 5.50–5.69(m, 2H), 6.10(d, J=11.2 Hz, 1H), 6.38(d, J=11.2 Hz, 1H). MS m/z: 454(M$^+$-H$_2$O), 312 (100%). UV $\lambda_{max}$ nm: 263.

Example 59
Preparation of 1α,3β-bis(tert-butyldimethylsilyloxy)-17α, 20α-epoxypregna-5,7-diene PTAD adduct A mixed solution of 1α,3β-bis(tert-butyldimethylsilyloxy) pregna-5,7,17(Z)-triene PTAD adduct (1.00 g, 1.39 mmol) and sodium bicarbonate (290 mg, 3.48 mmol) in dichloromethane (20 ml) was cooled at 0° C. and combined with 70% m-chloroperbenzoic acid (412 mg, 1.67 mmol). The reaction mixture was stirred at the same temperature for 0.5 hour, then diluted with dichloromethane, washed with saturated aqueous sodium bicarbonate solution, saturated aqueous sodium hydrogensulfite solution, saturated aqueous sodium bicarbonate solution and brine successively, and dried over magnesium sulfate. The solvent was distilled off under reduced pressure and the resulting residue was purified by column chromatography (hexane:ethyl acetate=5:1) to give the title compound as a colorless solid (920 mg, 90%).

$^1$H-NMR δ: 0.08(s, 3H), 0.09(s, 3H), 0.11(s, 3H), 0.15(s, 3H), 0.89(s, 9H), 0.91(s, 12H), 1.01(s, 3H), 1.41(d, 3H,

J=5.6 Hz), 3.00(q, 1H, J=5.6 Hz), 3.11–3.28(m, 1H), 3.85 (brs, 1H), 4.69–4.85(m, 1H), 6.13(d, 1H, J=8.3 Hz), 6.28(d, 1H, J=7.9 Hz), 7.15(dd, 1H, J=7.3, 7.6 Hz), 7.28(dd, 2H, J=7.6, 7.9 Hz), 7.38(d, 2H, J=7.6 Hz). UV $\lambda_{max}$ nm: 260.

Example 60

Preparation of 1α,3β-bis(tert-butyldimethylsilyloxy)-17α,20α-epoxypregna-5,7-diene In 1,3-dimethyl-2-imidazolidinone (60 ml) was dissolved 1α,3β-bis(tert-butyldimethylsilyloxy)-17α,20α-epoxypregna-5,7-diene PTAD adduct (613 mg, 0.835 mmol) and heated with stirring at 140° C. for 5 hours. The reaction solution was taken into water, extracted with ethyl acetate and washed with brine, then dried over anhydrous magnesium sulfate. The solvent was distilled off under reduced pressure and the resulting residue was purified by column chromatography (hexane:ethyl acetate=20:1) to give the title compound as a colorless solid (328 mg, 70%).

$^1$H-NMR δ: 0.04(s, 9H), 0.08(s, 3H), 0.81(s, 3H), 0.86(s, 18H), 0.88(s, 3H), 1.36(d, 3H, J=5.6 Hz), 2.95(q, 1H, J=5.6 Hz), 3.67(brs, 1H), 3.95–4.10(m, 1H), 5.33–5.44(m, 1H), 5.57(d, 1H, J=5.3 Hz). UV $\lambda_{max}$ nm: 269, 281, 293.

Example 61

Preparation of 1α,3β-bis(tert-butyldimethylsilyloxy)-20(S)-hydroxypregna-5,7,16-triene A solution of 1.5 M lithium diisopropylamide solution in cyclohexane (4.7 ml, 7.05 mmol) in toluene (3 ml) was cooled at 0° C. and combined with 0.95 M diethylaluminium chloride solution in hexane (4.95 ml, 4.70 mmol). The reaction solution was stirred at the same temperature for 0.5 hour, then stirred with a solution of 1α,3β-bis(tert-butyldimethylsilyloxy)-17α,20α-epoxypregna-5,7-diene (328 mg, 0.587 mmol) in toluene (5 ml) at the same temperature for 3 hours, combined with saturated aqueous sodium bicarbonate solution and ethyl acetate and filtered through Celite. The organic layer was washed with brine and dried over magnesium sulfate, and the solvent was distilled off under reduced pressure and the resulting residue was purified by column chromatography (hexane:ethyl acetate= 10:1) to give the title compound as a colorless solid (277 mg, 84%).

$^1$H-NMR δ: 0.05(s, 3H), 0.07(s, 6H), 0.11(s, 3H), 0.88(s, 21H), 0.95(s, 3H), 1.36(d, 3H, J=6.3 Hz), 3.71(brs, 1H), 3.97–4.12(m, 1H), 4.39(q, 1H, J=6.3 Hz), 5.35–5.44(m, 1H), 5.61(d, 1H, J=5.3 Hz), 5.67(s, 1H). UV $\lambda_{max}$ nm: 270, 281, 293.

Example 62

Preparation of 1α,3β-bis(tert-butyldimethylsilyloxy)-20(S)-(3-hydroxy-3-methylbutyloxy)pregna-5,7,16-triene After a mixed solution of 1α,3β-bis(tert-butyldimethylsilyloxy)-20(S)-hydroxypregna-5,7,16-triene (97 mg, 0.175mmol), sodium hydride (50 mg, 2.08 mmol) and 4-bromo-2,3-epoxy-2-methylbutane (145 mg, 0.877 mmol) in tetrahydrofuran (2 ml) was heated under reflux for 12 hours, 1M lithium tri-s-butylborohydride solution in tetrahydrofuran (1.8 ml, 1.80 mmol) was added and the mixed solution was heated under reflux for 45 minutes. The reaction solution was stirred with 3N aqueous sodium hydroxide solution and 30% aqueous hydrogen peroxide at room temperature for 30 minutes, then diluted with ethyl acetate, washed with brine and dried over magnesium sulfate. The solvent was distilled off under reduced pressure and the resulting residue was purified by column chromatography (hexane:ethyl acetate=10:1) to give the title compound as a colorless oil (113 mg, 100%).

IR(neat): 3500, 2960, 2860, 1463, 1375, 1260, 1105 cm$^{-1}$.
$^1$H-NMR δ: 0.05(s, 3H), 0.07(s, 6H), 0.11(s, 3H), 0.88(s, 21H), 0.94(s, 3H), 1.23(s, 3H), 1.24(s, 3H), 1.31(d, 3H, J=6.6 Hz), 3.47–3.59(m, 1H), 3.59–3.78(m, 1H), 3.70(brs, 1H), 3.93(q, 1H, J=6.6 Hz), 3.98–4.12(m, 1H), 5.34–5.45(m, 1H), 5.57–5.70(m, 2H). UV $\lambda_{max}$ nm: 269, 281, 293.

Example 63

Preparation of 1α,3β-dihydroxy-20(S)-(3-hydroxy-3-methylbutyloxy)pregna-5,7,16-triene A solution of 1α,3β-bis(tert-butyldimethylsilyloxy)-20 (S)-(3-hydroxy-3-methylbutyloxy)pregna-5,7,16-triene (27 mg, 0.0419 mmol) in tetrahydrofuran (1 ml) was combined with 1M tetra-n-butylammonium fluoride solution in tetrahydrofuran (0.25 ml, 0.25 mmol), and stirred at room temperature for 20 hours, then with heating under reflux for 2 hours. The reaction solution was diluted with ethyl acetate and washed with saturated aqueous sodium bicarbonate solution and brine successively, and the organic layer was dried over magnesium sulfate. The solvent was distilled off under reduced pressure and the resulting residue was purified by preparative thin layer chromatography (0.5 mm×1 and 0.25 mm×1, dichloromethane:ethanol 20:1, developed twice) to give the title compound as a colorless oil (17.3 mg, 99%).

IR(neat): 3420, 2940, 1735, 1660, 1460, 1365, 1270, 1150, 1055 cm$^{-1}$. $^1$H-NMR δ: 0.88(s, 3H), 0.96(s, 3H), 1.22(s, 3H), 1.23(s, 3H), 1.30(d, 3H, J=6.6 Hz), 3.45–3.58 (m, 1H), 3.58–3.72(m, 2H), 3.76(brs, 1H), 3.94(q, 1H, J=6.6 Hz), 3.98–4.14(m, 1H), 5.37–5.48(m, 1H), 5.62(s, 1H), 5.72(d, 1H, J=3.6 Hz). UV $\lambda_{max}$ nm: 270, 281, 293.

Example 64

Preparation of 1α,3β-dihydroxy-20(S)-(3-hydroxy-3-methylbutyloxy)-9,10-secopregna-5,7,10(19),16-tetraene Using 1α,3β-dihydroxy-20(S)-(3-hydroxy-3-methylbutyloxy)pregna-5,7,16-triene (11 mg, 0.0264 mmol) and ethanol (200 ml), the reaction was performed by the same procedure as in Example 15 (irradiation for 1 minute and 50 seconds, and heating under reflux for 2 hours), and then the solvent was distilled off under reduced pressure and the resulting residue was purified by preparative thin layer chromatography (0.25 mm×1, dichloromethane:ethyl acetate=20:1, developed twice, then 0.25 mm×0.5, hexane:ethyl acetate:ethanol=10:5:1, developed three times) to give the title compound as a colorless oil (0.890 mg, 8.1%).

IR(neat): 3400, 2980, 2940, 1450, 1370, 1160, 1060 cm$^{-1}$.
$^1$H-NMR δ: 0.78(s, 3H), 1.23(s, 3H), 1.24(s, 3H), 1.31(d, 3H, J=6.6 Hz), 3.47–3.58(m, 1H), 3.63(s, 1H), 3.61–3.73(m, 1H), 3.91(q, 1H, J=6.6 Hz), 4.18–4.30(m, 1H), 4.39–4.51(m, 1H), 5.01(s, 1H), 5.34(s, 1H), 5.59(brs, 1H), 6.10(d, 1H, J=11.6 Hz), 6.37(d, 1H, J=11.6 Hz). UV $\lambda_{max}$ nm: 263.

Example 65

Preparation of 1α,3β-bis(tert-butyldimethylsilyloxy)-20-oxopregna-5,7,16-triene

A suspension of 1α,3β-bis(tert-butyldimethylsilyloxy)-20 (S)-hydroxypregna-5,7,16-triene (600 mg, 1.07 mmol), pyridinium dichromate (610 mg, 1.61 mmol) and Florisil (3 g) in dichloromethane (10 ml) was stirred at room temperature for 1.5 hours, then ultrasonicated for 2.5 hours. The solvent was distilled off under reduced pressure and the resulting residue was diluted with diethyl ether and filtered through Celite. The solvent was distilled off under reduced pressure and the resulting residue was purified by column chromatography (hexane:ethyl acetate=15:1) to give the title compound as a colorless solid (343 mg, 57%).

IR(KBr): 2920, 2850, 1655, 1585, 1460, 1370, 1250, 1225, 1100, 1075, 1060 cm$^{-1}$. $^1$H-NMR δ: 0.06(s, 6H), 0.07(s, 3H), 0.11(s, 3H), 0.87(s, 9H), 0.89(s, 12H), 0.95(s,

3H), 2.28(s, 3H), 3.72(brs, 1H), 3.95–4.15(m, 1H), 5.36–5.44(m, 1H), 5.57–5.67(m, 1H), 6.74(brs, 1H). MS m/z: 556(M$^+$), 367(100%). UV $\lambda_{max}$ nm: 238, 270, 281, 293.

Example 66
Preparation of 1α,3β-bis(tert-butyldimethylsilyloxy)-20-oxopregna-5,7,16-triene A solution of 1α,3β-bis(tert-butyldimethylsilyloxy)-20(S)-hydroxypregna-5,7,16-triene (50.0 mg, 0.0894 mmol) and 4-methylmorpholine-N-oxide (15.7 mg, 0.134 mmol) in dichloromethane (1 ml) was stirred with powdered molecular sieve 4A at room temperature for 10 minutes. This was combined with tetra-n-butylammonium perruthenate (1.6 mg, 0.00447 mmol) and stirred at room temperature for 30 minutes. The reaction solution was filtered and then diluted with dichloromethane, and the organic layer was washed with saturated aqueous sodium bicarbonate solution, brine and saturated aqueous copper sulfate solution successively and dried over magnesium sulfate. The solvent was distilled off under reduced pressure and the resulting residue was purified by preparative thin layer chromatography (0.5 mm×1, hexane:ethyl acetate=5:1, developed once) to give the title compound as a colorless solid (37.1 mg, 74%).

Example 67
Preparation of 1α,3β-bis(tert-butyldimethylsilyloxy)-20(R)-hydroxypregna-5,7,16-triene To a solution of 1α,3β-bis(tert-butyldimethylsilyloxy)-20-oxopregna-5,7,16-triene (93 mg, 0.167 mmol) and cerium (III) chloride heptahydrate (93 mg, 0.251 mmol) in methanol (1.5 ml) and tetrahydrofuran (6 ml) cooled at 0° C. was gradually added sodium borohydride (32 mg, 0.835 mmol). The reaction solution was stirred at room temperature for one hour, then concentrated under reduced pressure and the residue was taken into water and extracted with ethyl acetate. The organic layer was washed with brine and then dried over magnesium sulfate, and the solvent was distilled off under reduced pressure. The resulting residue was purified by preparative thin layer chromatography (0.5 mm×2, hexane:ethyl acetate=10:1, developed three times) to give the title compound as a colorless solid (68.2 mg, 73%) and 1α,3β-bis(tert-butyldimethylsilyloxy)-20(S)-hydroxypregna-5,7,16-triene (17.0 mg, 18%).

Title compound: $^1$H-NMR δ: 0.05(s, 3H), 0.07(s, 6H), 0.11(s, 3H), 0.85(s, 3H), 0.89(s, 18H), 0.95(s, 3H), 1.37(d, 3H, J=6.6 Hz), 3.70(brs, 1H), 3.96–4.12(m, 1H), 4.31–4.44 (m, 1H), 5.31–5.43(m, 1H), 5.61(d, 1H, J=5.3 Hz), 5.66(brs, 1H). UV $\lambda_{max}$ nm: 270, 281, 293.

Example 68
Preparation of 1α,3β-bis(tert-butyldimethylsilyloxy)-20(R)-(3-hydroxy-3-methylbutyloxy)pregna-5,7,16-triene A mixed solution of 1α,3β-bis(tert-butyldimethylsilyloxy)-20(R)-hydroxypregna-5,7,16-triene (51 mg, 0.0911 mmol), sodium hydride (50 mg, 2.08 mmol) and 4-bromo- 2,3-epoxy-2-methylbutane (75 mg, 0.455 mmol) in tetrahydrofuran (2 ml) was heated under reflux for 1.5 hours and combined with 1M lithium tri-s-butylborohydride solution in tetrahydrofuran (0.9 ml, 0.900 mmol), and the mixed solution was heated under reflux for 20 minutes. The reaction solution was stirred with 3N aqueous sodium hydroxide solution and 30% aqueous hydrogen peroxide at room temperature for 30 minutes, then diluted with ethyl acetate, washed with brine and dried over magnesium sulfate. The solvent was distilled off under reduced pressure and the resulting residue was purified by preparative thin layer chromatography (0.5 mm×1, hexane:ethyl acetate=10:1, developed twice) to give the title compound as a colorless oil (48.6 mg, 83%).

IR(neat): 3500, 2950, 2870, 1470, 1380, 1260 cm$^{-1}$. $^1$H-NMR δ: 0.05(s, 3H), 0.06(s, 3H), 0.07(s, 3H), 0.11(s, 3H), 0.85(s, 3H), 0.88(s, 18H), 0.94(s, 3H), 1.23(s, 3H), 1.24(s, 3H), 1.32(d, 3H, J=6.6 Hz), 1.73(t, 2H, J=5.6 Hz), 3.53(s, 1H), 3.57–3.70(m, 2H), 3.70(brs, 1H), 3.93–4.11(m, 2H), 5.31–5.42(m, 1H), 5.60(d, 1H, J=5.6 Hz), 5.64(s, 1H). UV $\lambda_{max}$ nm: 270, 281, 293.

Example 69
Preparation of 1α,3β-dihydroxy-20(R)-(3-hydroxy-3-methylbutyloxy)pregna-5,7,16-triene A solution of 1α,3β-bis(tert-butyldimethylsilyloxy)-20(R)-(3-hydroxy-3-methylbutyloxy)pregna-5,7,16-triene (50 mg, 0.0775 mmol) in tetrahydrofuran (1 ml) was combined with 1M tetra-n-butylammonium fluoride solution in tetrahydrofuran (0.5 ml) and stirred at room temperature for 12 hours, then with heating under reflux for 5 hours. The reaction solution was diluted with ethyl acetate and washed with saturated aqueous sodium bicarbonate solution and brine successively, and the organic layer was dried over magnesium sulfate. The solvent was distilled off under reduced pressure and the resulting residue was purified by preparative thin layer chromatography (0.5 mm×2, dichloromethane:ethanol=20:1, developed twice) to give the title compound as a colorless oil (23.8 mg, 74%) and recovered raw materials (6 mg, 12%).

IR(neat): 3420, 2970, 2940, 1460, 1370, 1160, 1088, 1060 cm$^{-1}$. $^1$H-NMR δ: 0.84(s, 3H), 0.97(s, 3H), 1.23(s, 3H), 1.24(s, 3H), 1.73(d, 3H, J=6.6 Hz), 3.59–3.72(m, 3H), 3.77(brs, 1H), 4.00(q, 1H, J=6.6 Hz), 4.06–4.20(m, 1H), 5.41–5.51(m, 1H), 5.65(s, 1H), 5.73(d, 1H, J=4.0 Hz). UV $\lambda_{max}$ nm: 270, 281, 292.

Example 70
Preparation of 1α,3β-dihydroxy-20(R)-(3-hydroxy-3-methylbutyloxy)-9,10-secopregna-5,7,10(19),16-tetraene Using 1α,3β-dihydroxy-20(R)-(3-hydroxy-3-methylbutyloxy)pregna-5,7,16-triene (12.2 mg, 0.0293 mmol) and ethanol (200 ml), the reaction was performed by the same procedure as in Example 15 (irradiation for 1 minute and 30 seconds, and heating under reflux for 2 hours), and then the solvent was distilled off under reduced pressure and the resulting residue was purified by preparative thin layer chromatography (0.25 mm×1, dichloromethane:ethanol=10:1, developed once, then 0.25 mm×0.5, hexane:ethyl acetate:ethanol=10:5:1, developed three times) to give the title compound as a colorless oil (1.11 mg, 9.1%).

IR(neat): 3380, 2940, 2850, 1370, 1160, 1055 cm$^{-1}$. $^1$H-NMR δ: 0.75(s, 3H), 1.23(s, 3H), 1.24(s, 3H), 1.32(d, 3H, J=6.6 Hz), 1.75(t, 2H, J=5.9 Hz), 3.58(s, 1H), 3.65(t, 2H, J=5.9 Hz), 3.97(q, 1H, J=6.6 Hz), 4.20–4.25(m, 1H), 4.40–4.51(m, 1H), 5.00(s, 1H), 5.33(s, 1H), 5.62(s, 1H), 6.10(d, 1H, J=11.6 Hz), 6.37(d, 1H, J=11.6 Hz). UV $\lambda_{max}$ nm: 264.

Example 71
Preparation of 1α,3β-dihydroxy-20(S)-(2-ethyl-2-hydroxybutylthio)-9,10-secopregna-5,7,10(19),16-tetraene Under the same conditions as in Example 3, 1α,3β-bis(tert-butyldimethylsilyloxy)-20(S)-phenoxycarbonylthio-9,10-secopregna-5,7,10(19),16-tetraene (6.8 mg, 0.00978 mmol), 1,2-epoxy-2-ethylbutane (9.8 mg, 0.0978 mmol), tetrahydrofuran (0.5 ml) and 1M KOH solution in methanol (0.5 ml) were reacted and then concentrated under reduced pressure. The residue was diluted with ethyl acetate, washed with water and brine successively and dried over magnesium sulfate. The solvent was removed under reduced pressure and the resulting residue was purified by preparative thin layer chromatography (0.25 mm×1, hexane:ethyl acetate=4:1, developed once) to give a fraction containing 1α,3β-bis(tert-butyldimethylsilyloxy)-20(S)-(2-ethyl-2-hydroxybutylthio)-9,10-secopregna-5,7,10(19),16-tetraene. This was reacted with tetrahydrofuran (2 ml) and 1M tetra-n-butylammonium fluoride solution in tetrahydrofuran (1 ml) (60° C., 1.5 hours) and worked up by the same procedure as in Example 9, and then the residue was purified by preparative thin layer chromatography (0.25 mm×1, hexane:ethyl acetate:ethanol=12:8:1, developed three times) to give the title compound as a colorless oil (2.05 mg, 47%).

IR(neat): 3369, 2964, 2929, 2879, 2848, 1446, 1369, 1055 cm$^{-1}$. $^1$H-NMR δ: 0.84(s, 3H), 1.42(d, J=7.3 Hz, 3H), 2.76–2.87(m, 1H), 3.43(q, J=6.8 Hz, 1H), 4.18–4.30(m, 1H), 4.38–4.50(m, 1H), 5.01(brs, 1H), 5.34(brs, 1H), 5.62(brs, 1H), 6.10(d, J=11.2 Hz, 1H), 6.37(d, J=11.2 Hz, 1H). UV λ$_{max}$ nm: 263.

Example 72
Preparation of 1α,3β-dihydroxy-20(R)-(2-ethyl-2-hydroxybutylthio)-9,10-secopregna-5,7,10(19),16-tetraene Under the same conditions as in Example 71, 1α,3β-bis(tert-butyldimethylsilyloxy)-20(R)-phenoxycarbonylthio-9,10-secopregna-5,7,10(19),16-tetraene (6.9 mg, 0.00993 mmol), 1,2-epoxy-2-ethylbutane (9.9 mg, 0.0993 mmol), tetrahydrofuran (0.5 ml) and 1M KOH solution in methanol (0.5 ml) were subjected to alkylation reaction and worked up, and then the residue was purified by preparative thin layer chromatography (0.25 mm×1, hexane:ethyl acetate=4:1, developed once) to give a fraction containing 1α,3β-bis(tert-butyldimethylsilyloxy)-20(R)-(2-ethyl-2-hydroxybutylthio)-9,10-secopregna-5,7,10(19),16-tetraene. This was reacted with tetrahydrofuran (2 ml) and 1M tetra-n-butylammonium fluoride solution in tetrahydrofuran (1 ml) (60° C., 1.5 hours) and worked up by the same procedure as in Example 9, and then the residue was purified by preparative thin layer chromatography (0.25 mm×1, hexane:ethyl acetate:ethanol=12:8:1, developed three times) to give the title compound as a colorless oil (2.64 mg, 59%).

IR(neat): 3369, 2929, 2909, 2879, 2848, 1446, 1371, 1055 cm$^{-1}$. $^1$H-NMR δ: 0.73(s, 3H), 0.87(t, J=7.4 Hz, 3H), 0.88(t, J=7.4 Hz, 3H), 1.46(d, J=6.9 Hz, 3H), 2.77–2.87(m, 1H), 3.35(q, J=6.9 Hz, 1H), 4.18–4.31(m, 1H), 4.39–4.01(m, 1H), 5.01(brs, 1H), 5.34(brs, 1H), 5.59(brs, 1H), 6.10(d, J=11.2 Hz, 1H), 6.37(d, J=11.2 Hz, 1H). UV λ$_{max}$ nm: 263.

Example 73
Preparation of 1α,3β-dihydroxy-20(S)-{2(S)-hydroxy-3-methylbutylthio}-9,10-secopregna-5,7,10(19),16-tetraene Under the same conditions as in Example 71, 1α,3β-bis(tert-butyldimethylsilyloxy)-20(S)-phenoxycarbonylthio-9,10-secopregna-5,7,10(19),16-tetraene (5.7 mg, 0.00820 mmol), (S)-(+)-1,2-epoxy-3-methylbutane (3.53 mg, 0.0410 mmol), tetrahydrofuran (0.5 ml) and 1M KOH solution in methanol (0.5 ml) were subjected to alkylation reaction and worked up, and then the residue was purified by preparative thin layer chromatography (0.25 mm×1, hexane:ethyl acetate=3:1, developed once) to give a fraction containing 1α,3β-bis(tert-butyldimethylsilyloxy)-20(S)-{2(S)-hydroxy-3-methylbutylthio}-9,10-secopregna-5,7,10(19),16-tetraene. This was reacted with tetrahydrofuran (0.5 ml) and 1M tetra-n-butylammonium fluoride solution in tetrahydrofuran (0.3 ml) (60° C., 2 hours) and worked up by the same procedure as in Example 9, and then the residue was purified by preparative thin layer chromatography (0.25 mm×1, hexane:ethyl acetate:ethanol=12:8:1, developed three times) to give the title compound as a colorless oil (1.36 mg, 38%).

IR(neat): 3400, 2950, 2920, 2860, 2845, 1450, 1370, 1050 cm$^{-1}$. $^1$H-NMR δ: 0.85(s, 3H), 0.93(d, J=7.4 Hz, 3H), 0.96(d, J=7.4 Hz, 3H), 1.43(d, J=6.9 Hz, 3H), 2.53–2.66(m, 1H), 2.73(dd, J=13.4, 3.2 Hz, 1H), 2.76–2.88(m, 1H), 3.32–3.54(m, 2H), 4.16–4.30(m, 1H), 4.38–4.51(m, 1H), 5.01(brs, 1H), 5.34(brs, 1H), 5.64(brs, 1H), 6.10(d, J=11.2 Hz, 1H), 6.37(d, J=11.2 Hz, 1H). UV λ$_{max}$ nm: 263.

Example 74
Preparation of 1α,3β-dihydroxy-20(S)-{2(R)-hydroxy-3-methylbutylthio}-9,10-secopregna-5,7,10(19),16-tetraene Under the same conditions as in Example 71, 1α,3β-bis(tert-butyldimethylsilyloxy)-20(S)-phenoxycarbonylthio-9,10-secopregna-5,7,10(19),16-tetraene (5.1 mg, 0.00734 mmol), (R)-(−)-1,2-epoxy-3-methylbutane (3.16 mg, 0.0367 mmol), tetrahydrofuran (0.5 ml) and 1M KOH solution in methanol (0.5 ml) were subjected to alkylation reaction and worked up, and then the residue was purified by preparative thin layer chromatography (0.25 mm×1, hexane:ethyl acetate=3:1, developed once) to give a fraction containing 1α,3β-bis(tert-butyldimethylsilyloxy)-20(S)-{2(R)-hydroxy-3-methylbutylthio}-9,10-secopregna-5,7,10(19),16-tetraene. This was reacted with tetrahydrofuran (0.5 ml) and 1M tetra-n-butylammonium fluoride solution in tetrahydrofuran (0.3 ml) (60° C., 2 hours) and worked up by the same procedure as in Example 9, and then the residue was purified by preparative thin layer chromatography (0.25 mm×1, hexane:ethyl acetate:ethanol=12:8:1, developed three times) to give the title compound as a colorless oil (1.34 mg, 42%).

IR(neat), 3400, 2958, 2929, 2850, 1446, 1369, 1254, 1213, 1053 cm$^{-1}$. $^1$H-NMR δ: 0.81(s, 3H), 0.92(d, J=6.8 Hz, 3H), 0.96(d, J=6.8 Hz, 3H), 1.41(d, J=6.8 Hz, 3H), 2.56–2.66(m, 1H), 2.70(dd, J=13.4, 2.8 Hz, 1H), 2.76–2.88(m, 1H), 3.31–3.42(m, 1H), 3.51(q, J=6.8 Hz, 1H), 4.18–4.30(m, 1H), 4.39–4.50(m, 1H), 5.01(brs, 1H), 5.34(brs, 1H), 5.61(brs, 1H), 6.10(d, J=11.2 Hz, 1H), 6.37(d, J=11.2 Hz, 1H). UV λ$_{max}$ nm: 264.

Example 75
Preparation of 1α,3β-dihydroxy-20(R)-{2(S)-hydroxy-3-methylbutylthio}-9,10-secopregna-5,7,10(19),16-tetraene Under the same conditions as in Example 71, 1α,3β-bis(tert-butyldimethylsilyloxy)-20(R)-phenoxycarbonylthio-9,10-secopregna-5,7,10(19),16-tetraene (7.1 mg, 0.0102 mmol), (S)-(+)-1,2-epoxy-3-methylbutane (4.4 mg, 0.0510 mmol), tetrahydrofuran (0.5 ml) and 1M KOH solution in methanol (0.5 ml) were subjected to alkylation reaction and worked up, and then the residue was purified by preparative thin layer chromatography (0.25 mm×1, hexane:ethyl acetate=4:1, developed once) to give a fraction containing 1α,3β-bis(tert-butyldimethylsilyloxy)-20(R)-{2(S)-hydroxy-3-methylbutylthio}-9,10-secopregna-5,7,10(19),16-tetraene. This was reacted with tetrahydrofuran (0.5 ml) and 1M tetra-n-butylammonium fluoride solution in tetrahydrofuran (0.3 ml) (60° C., 2 hours) and worked up by the same procedure as in Example 9, and then the residue was purified by preparative thin layer chromatography (0.25 mm×1, hexane:ethyl acetate:ethanol=12:8:1, developed three times) to give the title compound as a colorless oil (1.24 mg, 28%).

IR(neat), 3367, 2956, 2929, 2850, 1446, 1369, 1215, 1055 cm$^{-1}$. $^1$H-NMR δ: 0.75(s, 3H), 0.93(d, J=6.9 Hz, 3H), 0.96(d, J=6.9 Hz, 3H), 1.46(d, J=6.9 Hz, 3H), 2.56–2.66(m, 1H), 2.74(dd, J=13.2, 3.0 Hz, 1H), 2.78–2.88(m, 1H), 3.32–3.48(m, 2H), 4.16–4.29(m, 1H), 4.38–4.50(m, 1H), 5.01(brs, 1H), 5.34(brs, 1H), 5.60(brs, 1H), 6.10(d, J=11.2 Hz, 1H), 6.37(d, J=11.2 Hz, 1H). UV λ$_{max}$ nm: 263.

Example 76
Preparation of 1α,3β-dihydroxy-20(R)-{2(R)-hydroxy-3-methylbutylthio}-9,10-secopregna-5,7,10(19),16-tetraene Under the same conditions as in Example 71, 1α,3β-bis(tert-butyldimethylsilyloxy)-20(R)-phenoxycarbonylthio-9,10-secopregna-5,7,10(19),16-tetraene (6.7 mg, 0.00964 mmol), (R)-(−)-1,2-epoxy-3-methylbutane (4.2 mg, 0.0482 mmol), tetrahydrofuran (0.5 ml) and 1M KOH solution in methanol (0.5 ml) were subjected to alkylation reaction and worked up, and then the residue was purified by preparative thin layer chromatography (0.25 mm×1, hexane:ethyl acetate=4:1, developed once) to give a fraction containing 1α,3β-bis(tert-butyldimethylsilyloxy)-20(R)-{2(R)-hydroxy-3-methylbutylthio}-9,10-secopregna-5,7,10(19),16-tetraene. This was reacted with tetrahydrofuran (0.5 ml) and 1M tetra-n-butylammonium fluoride solution in tetrahydrofuran (0.3 ml) (60° C., 2 hours) and worked up by the same procedure as in Example 9, and then the residue was purified by preparative thin layer chromatography (0.25 mm×1, hexane:ethyl acetate:ethanol=12:8:1, developed three times) to give the title compound as a colorless oil (0.754 mg, 18%).

IR(neat), 3340, 2922, 2846, 1456, 1369, 1290, 1238, 1043 cm$^{-1}$. $^1$H-NMR δ: 0.72(s, 3H), 0.94(d, J=6.9 Hz, 3H), 0.97(d, J=6.9 Hz, 3H), 1.47(d, J=6.9 Hz, 3H), 2.56–2.68(m, 1H), 2.75–2.88(m, 2H), 3.32–3.45(m, 2H), 4.18–4.30(m, 1H), 4.39–4.50(m, 1H), 5.01(brs, 1H), 5.34(brs, 1H), 5.61 (brs, 1H), 6.10(d, J=11.2 Hz, 1H), 6.37(d, J=11.2 Hz, 1H). UV $\lambda_{max}$ nm: 263.

Example 77
Preparation of 1α,3β-bis(tert-butyldimethylsilyloxy)-20(S)-{3-ethyl-2(S)-hydroxypentylthio}pregna-5,7,16-triene and 1α,3β-bis(tert-butyldimethylsilyloxy)-20(S)-{3-ethyl-2(R)-hydroxypentylthio}pregna-5,7,16-triene Under the same conditions as in Example 71, 1α,3β-bis(tert-butyldimethylsilyloxy)-20(S)-phenoxycarbonylthio-9,10-secopregna-5,7,10(19),16-tetraene (151.7 mg, 0.220 mmol), 1,2-epoxy-3-ethylpentane (503 mg, 4.40 mmol), tetrahydrofuran (1 ml) and 1M KOH solution in methanol (1 ml) were subjected to alkylation reaction and worked up, and then the residue was purified by preparative thin layer chromatography (0.5 mm×3, hexane:ethyl acetate=4:1, developed once) to give 1α,3β-bis(tert-butyldimethylsilyloxy)-20(S)-(3-ethyl-2-hydroxypentylthio)pregna-5,7,16-triene (diastreomer mixture). This was dissolved in dichloromethane (2 ml) and stirred with 4-dimethylaminopyridine (117 mg, 0.956 mmol) and (1R)-(+)-camphanic chloride (104 mg, 0.478 mmol) at room temperature for 15 minutes, and then the solvent was distilled off under reduced pressure. The residue was diluted with ethyl acetate, washed with ice-cooled 0.5 N hydrochloric acid, saturated aqueous sodium bicarbonate solution and brine successively and dried over magnesium sulfate. The solvent was removed under reduced pressure and the residue was purified by preparative thin layer chromatography (0.5 mm×4, hexane:benzene:ethyl acetate=10:20:1, developed three times) to separate low-polarity and high-polarity components. Each component was then dissolved in tetrahydrofuran (3 ml) and stirred with 1 M sodium methoxide solution in methanol (1 ml) at room temperature for 2 hours, and the solvent was distilled off under reduced pressure. The residue was diluted with ethyl acetate, washed with water and brine successively and dried over magnesium sulfate. The solvent was removed under reduced pressure and the resulting residue was purified by preparative thin layer chromatography (0.5 mm×2, hexane:ethyl acetate=4:1, developed once) to give 1α,3β-bis(tert-butyldimethylsilyloxy)-20(S)-{3-ethyl-2(S)-hydroxypentyl-thio}pregna-5,7,16-triene as a colorless oil (57.9 mg, 44%) and 1α,3β-bis(tert-butyldimethylsilyloxy)-20(S)-{3-ethyl-2(R)-hydroxypentylthio}pregna-5,7,16-triene as a colorless oil (56.7 mg, 43%).

1α,3β-bis(tert-butyldimethylsilyloxy)-20(S)-{3-ethyl-2(S)-hydroxypentylthio}pregna-5,7,16-triene:

IR(neat): 2897, 2856, 1462, 1371, 1254, 1099, 1082 cm$^{-1}$. $^1$H-NMR δ: 0.05(s, 3H), 0.06(s, 6H), 0.11(s, 3H), 0.88(s, 18H), 1.44(d, J=6.9 Hz, 3H), 2.47(dd, J=13.4, 9.6 Hz, 1H), 2.72(dd, J=13.4, 3.0 Hz, 1H), 2.79–2.91(m, 1H), 3.49(q, J=6.7 Hz, 1H), 3.60–3.73(m, 2H), 3.95–4.13(m, 1H), 5.34–5.42(m, 1H), 5.56–5,62(m, 1H), 5.66(brs, 1H). MS m/z: 557(M$^+$-OSi $^t$BuMe$_2$), 500(100%). UV $\lambda_{max}$ nm: 270, 281, 293.

1α,3β-bis(tert-butyldimethylsilyloxy)-20(S)-{3-ethyl-2(R)-hydroxypentylthio}pregna-5,7,16-triene:

IR(neat): 2956, 2929, 2856, 1462, 1371, 1254, 1099, 1082 cm$^{-1}$. $^1$H-NMR δ: 0.06(s, 3H), 0.07(s, 6H), 0.11(s, 3H), 0.89(s, 18H), 1.43(d, J=6.9 Hz, 3H), 2.68(dd, J=13.2, 3.0 Hz, 1H), 2.78–2.92(m, 1H), 3.53(q, J=6.8 Hz, 1H), 3.56–3.66(m, 1H), 3.71(brs, 1H), 3.95–4.12(m, 1H), 5.31–5.44(m, 1H), 5.52–5.68(m, 2H). MS m/z: 557(M$^+$-Osi $^t$BuMe$_2$), 500 (100%). UV $\lambda_{max}$ nm: 270, 281, 293.

Example 78
Preparation of 1α,3β-dihydroxy-20(S)-{3-ethyl-2(S)-hydroxypentylthio}pregna-5,7,16-triene By the same procedure as in Example 9, 1α,3β-bis(tert-butyldimethylsilyloxy)-20(S)-{3-ethyl-2(S)-hydroxypentylthio}pregna-5,7,16-triene (55.3 mg, 0.0802 mmol), tetrahydrofuran (3 ml) and 1M tetra-n-butylammonium fluoride solution in tetrahydrofuran (2 ml) were reacted (heating under reflux for 5 hours) and worked up, and then the residue was purified by preparative thin layer chromatography (0.5 mm×2, dichloromethane:ethanol=9:1, developed once) to give the title compound as a white solid (35.5 mg, 96%).

IR(KBr): 3390, 2950, 2920, 2870, 1460, 1365, 1045, 1030, 1020 cm$^{-1}$. $^1$H NMR (CDCl$_3$/CD$_3$OD) δ: 0.91(t, J=7.3 Hz, 6H), 0.94(s, 3H), 0.97(s, 3H), 1.44(d, J=6.9 Hz, 3H), 2.68(dd, J=13.4, 3.5 Hz, 1H), 2.78–2.90(m, 1H), 3.43–3.73 (m, 2H), 3.75(brs, 1H), 3.92–4.08(m, 1H), 5.40–5.49(m, 1H), 5.66(brs, 1H), 5.68–5.76(m, 1H). MS m/z: 460(M$^+$), 315(100%). UV $\lambda_{max}$ nm: 270, 281, 293.

Example 79
Preparation of 1α,3β-dihydroxy-20(S)-{3-ethyl-2(R)-hydroxypentylthio}pregna-5,7,16-triene By the same procedure as in Example 9, 1α,3β-bis(tert-butyldimethylsilyloxy)-20(S)-{3-ethyl-2(R)-hydroxypentyl-thio}pregna-5,7,16-triene (54.9 mg, 0.0797 mmol), tetrahydrofuran (3 ml) and 1M tetra-n-butylammonium fluoride solution in tetrahydrofuran (2 ml) were reacted (heating under reflux for 5 hours) and worked up, and then the residue was purified by preparative thin layer chromatography (0.5 mm×2, dichloromethane:ethanol=9:1, developed once) to give the title compound as a colorless oil (37.9 mg, 100%).

IR(neat): 3400, 2962, 2929, 2873, 1460, 1369, 1055, 1030 cm$^{-1}$. $^1$H-NMR δ: 0.90(t, J=7.3 Hz, 6H), 0.92(s, 3H), 0.98(s, 3H), 1.43(d, J=6.9 Hz, 3H), 2.68(dd, J=13.5, 3.0 Hz, 1H), 2.75–2.87(m, 1H), 3.55(q, J=6.9 Hz, 1H), 3.56–3.67(m, 1H), 3.79(brs, 1H), 3.99–4.16(m, 1H), 5.41–5.50(m, 1H), 5.63 (brs, 1H), 5.70–5.79(m, 1H). MS m/z: 460 (M$^+$), 313 (100%). UV $\lambda_{max}$ nm: 270, 281, 293.

Example 80
Preparation of 1α,3β-dihydroxy-20(S)-{3-ethyl-2(S)-hydroxypentylthio}-9,10-secopregna-5,7,10(19),16-tetraene Using 1α,3β-dihydroxy-20(S)-{3-ethyl-2(S)-hydroxypentylthio}pregna-5,7,16-triene (33.0 mg, 0.0716 mmol) and ethanol (200 ml), the reaction (irradiation for 3.25 minutes and heating under reflux for 2 hours) and work up were performed by the same procedure as in Example 15, and then the residue was purified by preparative thin layer chromatography (0.5 mm×1, dichloromethane:ethyl acetate:ethanol=14:6:1, developed twice, then 0.25 mm×1, hexane:ethyl acetate:ethanol=10:10:1, developed three times) to give the title compound as a colorless oil (1.81 mg, 5.5%).

IR(neat): 3367, 2960, 2873, 1456, 1369, 1055 cm$^{-1}$. $^1$H NMR δ: 0.85(s, 3H), 0.90(t, J=7.3 Hz, 6H), 1.43(d, J=6.9 Hz, 3H), 2.47(dd, J=13.3, 9.6 Hz, 1H), 2.55–2.68(m, 1H), 2.71(dd, J=13.3, 3.0 Hz, 1H), 2.78–2.89(m, 1H), 3.47(q, J=6.8 Hz, 1H), 3.60–3.72(m, 1H), 4.19–4.31(m, 1H), 4.40–4.51(m, 1H), 5.01(brs, 1H), 5.34(brs, 1H), 5.64(brs, 1H), 6.10(d, J=11.2 Hz, 1H), 6.37(d, J=11.2 Hz, 1H). MS m/z: 460(M$^+$), 312(100%). UV λ$_{max}$ nm: 263.

Example 81

Preparation of 1α,3β-dihydroxy-20(S)-{3-ethyl-2(R)-hydroxypentylthio}-9,10-secopregna-5,7,10(19),16-tetraene Using 1α,3β-dihydroxy-20(S)-{3-ethyl-2(R)-hydroxypentylthio}pregna-5,7,16-triene (34.1 mg, 0.0740 mmol) and ethanol (200 ml), the reaction (irradiation for 3.25 minutes and heating under reflux for 2 hours) and work up were performed by the same procedure as in Example 15, and then the residue was purified by preparative thin layer chromatography (0.5 mm×1, dichloromethane:ethyl acetate:ethanol=10:10:1, developed twice, then 0.25 mm×1, dichloromethane:ethanol=18:1, developed three times) to give the title compound as a colorless oil (2.13 mg, 6.2%).

IR(neat): 3369, 2960, 2929, 2873, 1446, 1369, 1055 cm$^{-1}$. $^1$H NMR δ: 0.82(s, 3H), 0.90(t, J=7.1 Hz, 6H), 1.42(d, J=6.9 Hz, 3H), 2.75–2.89(m, 1H), 3.51(q, J=6.9 Hz, 1H), 3.57–3.68(m, 1H), 4.18–4.31(m, 1H), 4.39–4.50(m, 1H), 5.01(brs, 1H), 5.34(brs, 1H), 5.60(brs, 1H), 6.11(d, J=11.2 Hz, 1H), 6.37(d, J=11.2 Hz, 1H). MS m/z: 460(M$^+$), 312 (100%). UV λ$_{max}$ nm: 263.

Example 82

Preparation of 1α,3β-dihydroxy-20(R)-{3-ethyl-2(R)-hydroxypentylthio}-9,10-secopregna-5,7,10(19),16-tetraene and 1α,3β-dihydroxy-20(R)-{3-ethyl-2(S)-hydroxypentylthio}-9,10-secopregna-5,7,10(19),16-tetraene By the same procedure as in Example 71, 1α,3β-bis(tert-butyldimethylsilyloxy)-20(R)-phenoxycarbonylthio-9,10-secopregna-5,7,10(19),16-tetraene (24.5 mg, 0.0352 mmol), 1,2-epoxy-3-ethylpentane (80.4 mg, 0.704 mmol), tetrahydrofuran (1 ml) and 1M KOH solution in methanol (1 ml) were subjected to alkylation reaction (room temperature, one hour) and worked up, and then the residue was purified by preparative thin layer chromatography (0.5 mm×1, hexane:ethyl acetate=4:1, developed once) to give 1α,3β-bis (tert-butyldimethylsilyloxy)-20(R)-(3-ethyl-2-hydroxypentylthio)-9,10-secopregna-5,7,10(19),16-tetraene (diastreomer mixture, 18.5 mg). An aliquot of 17.2 mg was dissolved in dichloromethane (1 ml) and stirred with 4-dimethylaminopyridine (15.3 mg, 0.125 mmol) and (1S)-(−)-camphanic chloride (13.5 mg, 0.0625 mmol) at room temperature for 15 minutes, and then the solvent was distilled off under reduced pressure. The residue was diluted with ethyl acetate, washed with ice-cooled 0.5 N hydrochloric acid, saturated aqueous sodium bicarbonate solution and brine successively and dried over magnesium sulfate. The solvent was removed under reduced pressure and the residue was purified by preparative thin layer chromatography (0.5 mm×1, hexane benzene:ethyl acetate=10:20:1, developed twice) to separate low-polarity and high-polarity components. Each component was then dissolved in tetrahydrofuran (1 ml) and stirred with 1 M sodium methoxide solution in methanol (0.5 ml) at room temperature for 2 hours, and the solvent was distilled off under reduced pressure. The residue was diluted with ethyl acetate, washed with water and brine successively and dried over magnesium sulfate. The solvent was removed under reduced pressure and the resulting residue was purified by preparative thin layer chromatography (0.5 mm×1, hexane:ethyl acetate=4:1, developed once) to give 1α,3β-bis(tert-butyldimethylsilyloxy)-20(R)-{3-ethyl-2(R)-hydroxypentyl-thio}-9,10-secopregna-5,7,10(19),16-tetraene and 1α,3β-bis(tert-butyldimethylsilyloxy)-20(R)-{3-ethyl-2(S)-hydroxypentylthio}-9,10-secopregna-5,7,10(19),16-tetraene. Each compound was reacted with tetrahydrofuran (1 ml) and 1M tetra-n-butylammonium fluoride solution in tetrahydrofuran (0.5 ml) (60° C., 2 hours) and worked up by the same procedure as in Example 9, and then the residue was purified by preparative thin layer chromatography (0.25 mm×1, hexane:ethyl acetate:ethanol= 12:8:1, developed three times) to give 1α,3β-dihydroxy-20 (R)-{3-ethyl-2(R)-hydroxypentylthio}-9,10-secopregna-5,7,10(19),16-tetraene as a colorless oil (3.09 mg, 20%) and 1α,3β-dihydroxy-20(R)-{3-ethyl-2(S)-hydroxypentylthio}-9,10-secopregna-5,7,10(19),16-tetraene as a colorless oil (2.95 mg, 20%).

1α,3β-dihydroxy-20(R)-{3-ethyl-2(R)-hydroxypentylthio}-9,10-secopregna-5,7,10(19),16-tetraene:

IR(neat): 3361, 2960, 2929, 2873, 1446, 1371, 1290, 1217, 1055 cm$^{-1}$. $^1$H NMR δ: 0.72(s, 3H), 0.91(t, J=7.1 Hz, 6H), 1.47(d, J=6.9 Hz, 3H), 2.54–2.67(m, 1H), 2.72–2.90(m, 2H), 3.37(q, J=6.9 Hz, 1H), 3.58–3.70(m, 1H), 4.18–4.29(m, 1H), 4.38–4.50(m, 1H), 5.01(brs, 1H), 5.34(brs, 1H), 5.61 (brs, 1H), 6.10(d, J=11.2 Hz, 1H), 6.37(d, J=11.2 Hz, 1H). MS m/z: 460(M$^+$), 312(100%). UV λ$_{max}$ nm: 263.

1α,3β-dihydroxy-20(R)-{3-ethyl-2(S)-hydroxypentylthio}-9,10-secopregna-5,7,10(19),16-tetraene:

IR(neat): 3369, 2960, 2929, 2873, 1448, 1371, 1290, 1211, 1055 cm$^{-1}$. $^1$H NMR δ: 0.75(s, 3H), 0.90(t, J=7.1 Hz, 6H), 1.46(d, J=6.9 Hz, 3H), 2.48(dd, J=13.5, 9.6 Hz, 1H), 2.55–2.66(m, 1H), 2.72(dd, J=13.5, 3.1 Hz, 1H), 2.76–2.88 (m, 1H), 3.41(q, J=6.9 Hz, 1H), 3.57–3.70(m, 1H), 4.18–4.30(m, 1H), 4.38–4.50(m, 1H), 5.01(brs, 1H), 5.34 (brs, 1H), 5.60(brs, 1H), 6.10(d, J=11.2 Hz, 1H), 6.37(d, J=11.2 Hz, 1H). MS m/z: 460(M$^+$), 312(100%). UV λ$_{max}$ nm: 263.

Example 83

Preparation of 1α,3β-bis(tert-butyldimethylsilyloxy)-20(S)-(4-methyl-4-triethylsilyloxy-2-pentynyloxy)pregna-5,7,16-triene A solution of 1α,3β-bis(tert-butyldimethylsilyloxy)-20 (S)-hydroxypregna-5,7,16-triene (60.0 mg, 0.107 mmol), sodium hydride (60%, 17.1 mg, 0.428 mmol), 15-crown-5 (10 μl) and 1-bromo-4-methyl-4-triethylsilyloxy-2-pentyne (109 mg, 0.375 mmol) in tetrahydrofuran (1 ml) was stirred at 60° C. for 2 hours. The solution was cooled to room temperature and then taken into water and extracted with ethyl acetate. The extract was washed with brine and dried over magnesium sulfate, and the solvent was distilled off under reduced pressure. The resulting residue was purified by preparative thin layer chromatography (0.5 mm×2, hexane:ethyl acetate=40:1, developed once) to give the title compound as a colorless oil (82.4 mg, 99%).

IR(neat): 2950, 2875, 1460, 1370, 1250, 1160, 1090, 1040 cm$^{-1}$. $^1$H NMR δ: 0.06(s, 3H), 0.07(s, 6H), 0.11(s, 3H), 0.67(q, J=7.8 Hz, 6H), 0.89(s, 18 H), 0.96(t, J=7.8 Hz, 9H), 1.32(d, J=6.5 Hz, 3H), 1.46(s, 6H), 3.70(brs, 1H), 3.76–3.83 (m, 1H), 3.94–4.39(m, 3H), 5.35–5.44(m, 1H), 5.56–5.66 (m, 2H). UV λ$_{max}$ nm: 270, 281, 293.

Example 84
Preparation of 1α,3β-bis(tert-butyldimethylsilyloxy)-20(S)-{(E)-(4-methyl-4-triethylsilyloxy-2-pentenyloxy)}pregna-5,7,16-triene Under the same conditions as in Example 83, 1α,3β-bis(tert-butyldimethylsilyloxy)-20(S)-hydroxypregna-5,7,16-triene (60.0 mg, 0.107 mmol), sodium hydride (60%, 17.1 mg, 0.428 mmol), 15-crown-5 (10 μl) and (E)-1-bromo-4-methyl-4-triethylsilyloxy-2-pentene (116 mg, 0.375 mmol) were reacted in tetrahydrofuran (1 ml) and worked up, and then the residue was purified by preparative thin layer chromatography (0.5 mm×2, hexane:ethyl acetate=40:1, developed once) to give the title compound as a colorless oil (85.9 mg, 99%).

IR(neat): 2950, 2850, 1460, 1370, 1250, 1150, 1040 cm$^{-1}$. $^1$H NMR δ: 0.06(s, 3H), 0.07(s, 6H), 0.11(s, 3H), 0.57(q, J=7.8 Hz, 6H), 0.89(s, 18 H), 0.94(t, J=7.8 Hz, 9H), 1.31(s, 6H), 3.72(brs, 1H), 3.79–4.18(m, 4H), 5.37–5.45(m, 1H), 5.57–5.83(m, 4H). UV λ$_{max}$ nm: 270, 281, 293.

Example 85
Preparation of 1α,3β-bis(tert-butyldimethylsilyloxy)-20(S)-{(Z)-(4-methyl-4-triethylsilyloxy-2-pentenyloxy)}pregna-5,7,16-triene Under the same conditions as in Example 83, 1α,3β-bis(tert-butyldimethylsilyloxy)-20(S)-hydroxypregna-5,7,16-triene (60.0 mg, 0.107 mmol), sodium hydride (60%, 17.1 mg, 0.428 mmol), 15-crown-5 (10 μl) and (Z)-1-bromo-4-methyl-4-triethylsilyloxy-2-pentene (125 mg, 0.428 mmol) were reacted in tetrahydrofuran (1 ml) and worked up, and then the residue was purified by preparative thin layer chromatography (0.5 mm×2, hexane:ethyl acetate=30:1, developed once) to give the title compound as a colorless oil (80.7 mg, 98%).

IR(neat): 2950, 2850, 1460, 1370, 1255, 1170, 1100, 1040 cm$^{-1}$. $^1$H NMR δ: 0.05(s, 3H), 0.07(s, 6H), 0.11(s, 3H), 0.58(q, J=7.8 Hz, 6H), 0.88(s, 18 H), 0.94(t, J=7.8 Hz, 9H), 1.32(s, 6H), 3.71(brs, 1H), 3.93–4.14(m, 2H), 4.16–4.36(m, 2H), 5.29–5.44(m, 3H), 5.57–5.66(m, 2H). UV λ$_{max}$ nm: 270, 281, 293.

Example 86
Preparation of 1α,3β-bis(tert-butyldimethylsilyloxy)-20(S)-(4-ethyl-4-triethylsilyloxy-2-hexynyloxy)pregna-5,7,16-triene Under the same conditions as in Example 83, 1α,3β-bis(tert-butyldimethylsilyloxy)-20(S)-hydroxypregna-5,7,16-triene (60.0 mg, 0.107 mmol), sodium hydride (60%, 21.0 mg, 0.525 mmol), 15-crown-5 (10 μl) and 1-bromo-4-ethyl-4-triethylsilyloxy-2-hexyne (134 mg, 0.420 mmol) were reacted in tetrahydrofuran (1 ml) and worked up, and then the residue was purified by preparative thin layer chromatography (0.5 mm×2, hexane:ethyl acetate=40:1, developed once) to give the title compound as a colorless oil (79.0 mg, 92%).

IR(neat): 2950, 2850, 1460, 1375, 1255, 1080, 1010 cm$^{-1}$. $^1$H NMR δ: 0.06(s, 3H), 0.07(s, 6H), 0.11(s, 3H), 0.67(q, J=7.8 Hz, 6H), 0.89(s, 18 H), 1.32(d, J=6.4 Hz, 3H), 3.72(brs, 1H), 3.95–4.32(m, 4H), 5.36–5.44(m, 1H), 5.58–5.68(m, 2H). MS m/z: 796(M), 278(100%). UV λ$_{max}$ nm: 270, 281, 293.

Example 87
Preparation of 1α,3β-bis(tert-butyldimethylsilyloxy)-20(S)-{(E)-(4-ethyl-4-triethylsilyloxy-2-hexenyloxy)}pregna-5,7,16-triene Under the same conditions as in Example 83, 1α,3β-bis(tert-butyldimethylsilyloxy)-20(S)-hydroxypregna-5,7,16-triene (60.0 mg, 0.107 mmol), sodium hydride (60%, 17.1 mg, 0.428 mmol), 15-crown-5 (10 μl) and (E)-1-bromo-4-ethyl-4-triethylsilyloxy-2-hexene (134 mg, 0.420 mmol) were reacted in tetrahydrofuran (1 ml) and worked up, and then the residue was purified by preparative thin layer chromatography (0.5 mm×2, hexane:ethyl acetate=40:1, developed once) to give the title compound as a colorless oil (86.0 mg, 100%).

IR(neat): 2950, 2850, 1460, 1375, 1255, 1100, 1000 cm$^{-1}$. $^1$H NMR δ: 0.06(s, 3H), 0.07(s, 6H), 0.11(s, 3H), 0.58(q, J=7.8 Hz, 6H), 0.89(s, 18 H), 1.31(d, J=6.6 Hz, 3H), 3.71(brs, 1H), 3.70–4.19(m, 4H), 5.37–5.45(m, 1H), 5.49–5.76(m, 4H). UV λ$_{max}$ nm: 270, 281, 293.

Example 88
Preparation of 1α,3β-bis(tert-butyldimethylsilyloxy)-20(S)-{(Z)-(4-ethyl-4-triethylsilyloxy-2-hexenyloxy)}pregna-5,7,16-triene Under the same conditions as in Example 83, 1α,3β-bis(tert-butyldimethylsilyloxy)-20(S)-hydroxypregna-5,7,16-triene (60.0 mg, 0.107 mmol), sodium hydride (60%, 17.1 mg, 0.428 mmol), 15-crown-5 (10 μl) and (Z)-1-bromo-4-ethyl-4-triethylsilyloxy-2-hexene (103 mg, 0.321 mmol) were reacted in tetrahydrofuran (1 ml) and worked up, and then the residue was purified by preparative thin layer chromatography (0.5 mm×2, hexane:ethyl acetate=40:1, developed once) to give the title compound as a colorless oil (83.6 mg, 98%).

IR(neat): 2950, 2850, 1460, 1370, 1250, 1100, 1000 cm$^{-1}$. $^1$H NMR δ: 0.06(s, 3H), 0.07(s, 6H), 0.11(s, 3H), 0.60(q, J=7.5 Hz, 6H), 0.89(s, 18H), 1.32(d, J=6.6 Hz, 3H), 3.71 (brs, 1H), 3.89–4.47 (m, 4H), 5.09–5.20(m, 1H), 5.35–5.66 (m, 4H). MS m/z: 798(M$^+$), 277(100%). UV λ$_{max}$ nm: 270, 281, 293.

Example 89
Preparation of 1α,3β-bis(tert-butyldimethylsilyloxy)-20(R)-(4-methyl-4-triethylsilyloxy-2-pentynyloxy)pregna-5,7,16-triene Under the same conditions as in Example 83, 1α,3β-bis(tert-butyldimethylsilyloxy)-20(R)-hydroxypregna-5,7,16-triene (60.0 mg, 0.107 mmol), sodium hydride (60%, 17.1 mg, 0.428 mmol), 15-crown-5 (10 μl) and 1-bromo-4-methyl-4-triethylsilyloxy-2-pentyne (109 mg, 0.375 mmol) were reacted in tetrahydrofuran (1 ml) and worked up, and then the residue was purified by preparative thin layer chromatography (0.5 mm×2, hexane:ethyl acetate=40:1, developed once) to give the title compound as a colorless oil (76.4 mg, 93%).

IR(neat): 2950, 2850, 1465, 1375, 1250, 1160, 1090, 1040 cm$^{-1}$. $^1$H NMR δ: 0.06(s, 3H), 0.07(s, 6H), 0.11(s, 3H), 0.67(g, J=7.8 Hz, 6H), 0.85(s, 3H), 0.89(s, 18H), 0.95(s, 3H), 0.96(t, J=7.8 Hz, 9H), 1.33(d, J=6.6 Hz, 3H), 1,48(s, 6H), 5 3.71(brs, 1H), 3.93–4.32(m, 4H), 5.36–5.45(m, 1H), 5.58–5.66(m, 1H), 5.60(brs, 1H). UV λ$_{max}$ nm: 270, 281, 293.

Example 90
Preparation of 1α,3β-bis(tert-butyldimethylsilyloxy)-20(R)-{(E)-(4-methyl-4-triethylsilyloxy-2-pentenyloxy)}pregna-5,7,16-triene Under the same conditions as in Example 83, 1α,3β-bis(tert-butyldimethylsilyloxy)-20(R)-hydroxypregna-5,7,16-triene (60.0 mg, 0.107 mmol), sodium hydride (60%, 17.1 mg, 0.428 mmol), 15-crown-5 (10 μl) and (E)-1-bromo-4-methyl-4-triethylsilyloxy-2-pentene (116 mg, 0.375 mmol) were reacted in tetrahydrofuran (1 ml) and worked up, and then the residue was purified by preparative thin layer chromatography (0.5 mm×2, hexane:ethyl acetate=30:1, developed once) to give the title compound as a colorless oil (73.4 mg, 89%).

IR(neat): 2950, 2850, 1460, 1370, 1250, 1150, 1095, 1040 cm$^{-1}$. $^1$H NMR δ: 0.06(s, 3H), 0.07(s, 6H), 0.11(s, 3H), 0.58(q, J=7.8 Hz, 6H), 0.85(s, 3H), 0.88(s, 9H), 0.89(s, 9H), 0.94(t, J=7.8 Hz, 9H), 0.94(s, 3H), 1.30(s, 6H), 1.33(d, J=5.1 Hz, 3H), 3.71(brs, 1H), 3.83–4.16(m, 4H), 5.35–5.45(m, 1H), 5.57–5.88(m, 4H). UV $λ_{max}$ nm: 270, 281, 293.

Example 91

Preparation of 1α,3β-bis(tert-butyldimethylsilyloxy)-20(R)-{(Z)-(4-methyl-4-triethylsilyloxy-2-pentenyloxy)}pregna-5,7,16-triene Under the same conditions as in Example 83, 1α,3β-bis(tert-butyldimethylsilyloxy)-20(R)-hydroxypregna-5,7,16-triene (60.0 mg, 0.107 mmol), sodium hydride (60%, 17.1 mg, 0.428 mmol), 15-crown-5 (10 μl) and (Z)-1-bromo-4-methyl-4-triethylsilyloxy-2-pentene (125 mg, 0.428 mmol) were reacted in tetrahydrofuran (1 ml) and worked up, and then the residue was purified by preparative thin layer chromatography (0.5 mm×2, hexane:ethyl acetate=30:1, developed once) to give the title compound as a colorless oil (70.3 mg, 85%).

IR(neat): 2950, 2850, 1460, 1375, 1255, 1170, 1100, 1040 cm$^{-1}$. $^1$H NMR δ: 0.06(s, 3H), 0.07(s, 6H), 0.11(s, 3H), 0.59(q, J=7.9 Hz, 6H), 0.86(s, 3H), 0.88(s, 9H), 0.89(s, 9H), 0.95(t, J=7.9 Hz, 9H), 0.95(s, 3H), 1.32(s, 6H), 1.33(d, J=4.9 Hz, 3H), 3.71(brs, 1H), 3.96–4.13(m, 2H), 4.23–4.38(m, 2H), 5.29–5.47(m, 3H), 5.58–5.68(m, 2H). UV $λ_{max}$ nm: 270, 281, 293.

Example 92

Preparation of 1α,3β-bis(tert-butyldimethylsilyloxy)-20(R)-(4-ethyl-4-triethylsilyloxy-2-hexynyloxy)pregna-5,7,16-triene Under the same conditions as in Example 83, 1α,3β-bis(tert-butyldimethylsilyloxy)-20(R)-hydroxypregna-5,7,16-triene (58.9 mg, 0.105 mmol), sodium hydride (60%, 21.0 mg, 0.525 mmol), 15-crown-5 (10 μl) and 1-bromo-4-ethyl-4-triethylsilyloxy-2-hexyne (134 mg, 0.420 mmol) were reacted in tetrahydrofuran (1 ml) and worked up, and then the residue was purified by preparative thin layer chromatography (0.5 mm×2, hexane:ethyl acetate=19:1, developed once) to give the title compound as a colorless oil (60.2 mg, 72%).

IR(neat): 2950, 2850, 1460, 1370, 1250, 1085 cm$^{-1}$. $^1$H NMR δ: 0.06(s, 3H), 0.07(s, 6H), 0.11(s, 3H), 0.67(q, J=7.3 Hz, 6H), 0.88(s, 9H), 0.89(s, 9H), 1.33(d, J=6.6 Hz, 3H), 3.71(brs, 1H), 3.97–4.35(m, 4H), 5.35–5.44(m, 1H), 5.58–5.64(m, 1H), 5.67(brs, 1H). MS m/z: 796(M), 301 (100%). UV $λ_{max}$ nm: 270, 281, 293.

Example 93

Preparation of 1α,3β-bis(tert-butyldimethylsilyloxy)-20(R)-{(E)-(4-ethyl-4-triethylsilyloxy-2-hexenyloxy)}pregna-5,7,16-triene Under the same conditions as in Example 83, 1α,3β-bis(tert-butyldimethylsilyloxy)-20(R)-hydroxypregna-5,7,16-triene (60.0 mg, 0.107 mmol), sodium hydride (60%, 17.1 mg, 0.428 mmol), 15-crown-5 (10 μl) and (E)-1-bromo-4-ethyl-4-triethylsilyloxy-2-hexene (134 mg, 0.420 mmol) were reacted in tetrahydrofuran (1 ml) and worked up, and then the residue was purified by preparative thin layer chromatography (0.5 mm×2, hexane:ethyl acetate=40:1, developed once) to give the title compound as a colorless oil (62.4 mg, 73%).

IR(neat): 2950, 2870, 1460, 1375, 1255, 1070 cm$^{-1}$. $^1$H NMR δ: 0.06(s, 3H), 0.07(s, 6H), 0.11(s, 3H), 0.58(q, J=7.8 Hz, 6H), 0.88(s, 9H), 0.89(s, 9H), 1.32(d, J=6.6 Hz, 3H), 3.71(brs, 1H), 3.88–4.14(m, 4H), 5.36–5.44(m, 1H), 5.54–5.76(m, 4H). MS m/z: 798(M$^+$), 609(100%). UV $λ_{max}$ nm: 270, 281, 293.

Example 94

Preparation of 1α,3β-bis(tert-butyldimethylsilyloxy)-20(R)-{(Z)-(4-ethyl-4-triethylsilyloxy-2-hexenyloxy)}pregna-5,7,16-triene Under the same conditions as in Example 83, 1α,3β-bis(tert-butyldimethylsilyloxy)-20(R)-hydroxypregna-5,7,16-triene (60.0 mg, 0.107 mmol), sodium hydride (60%, 17.1 mg, 0.428 mmol), 15-crown-5 (10 μl) and (Z)-1-bromo-4-ethyl-4-triethylsilyloxy-2-hexene (103 mg, 0.321 mmol) were reacted in tetrahydrofuran (1 ml) and worked up, and then the residue was purified by preparative thin layer chromatography (0.5 mm×2, hexane:ethyl acetate=40:1, developed once) to give the title compound as a colorless oil (84.6 mg, 99%).

IR(neat): 2950, 2850, 1460, 1375, 1255, 1100, 1070 cm$^{-1}$. $^1$H NMR δ: 0.05(s, 3H), 0.06(s, 6H), 0.11(s, 3H), 0.61(q, J=7.8 Hz, 6H), 0.88(s, 9H), 0.89(s, 9H), 1.32(d, J=6.6 Hz, 3H), 3.71(brs, 1H), 4.15–4.24(m, 2H), 4.23–4.38(m, 2H), 5.13(dt, J=12.5, 2.2 Hz, 1H), 5.35–5.42(m, 1H), 5.50(dt, J=12.2, 5.0 Hz, 1H), 5.59–5.69(m, 2H). MS m/z: 798(M$^+$), 610(100%). UV $λ_{max}$ nm: 270, 281, 293.

Example 95

Preparation of 1α,3β-dihydroxy-20(S)-(4-hydroxy-4-methyl-2-pentynyloxy)pregna-5,7,16-triene By the same procedure as in Example 9, 1α,3β-bis(tert-butyldimethylsilyloxy)-20(S)-(4-methyl-4-triethylsilyloxy-2-pentynyloxy)pregna-5,7,16-triene (80.0 mg, 0.104 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a pale yellow oil (14.0 mg, 32%).

IR(neat): 3400, 2980, 2940, 2850, 1450, 1370, 1230, 1170, 1060 cm$^{-1}$. $^1$H NMR δ: 0.90(s, 3H), 0.99(s, 3H), 1.33(d, J=6.4 Hz, 3H), 1.52(s, 6H), 3.79(brs, 1H), 3.98–4.23 (m, 4H), 5.43–5.50(m, 1H), 5.66(brs, 1H), 5.70–5.80(m, 1H). UV $λ_{max}$ nm: 270, 281, 293.

Example 96

Preparation of 1α,3β-dihydroxy-20(S)-{(E)-(4-hydroxy-4-methyl-2-pentenyloxy)}pregna-5,7,16-triene By the same procedure as in Example 9, 1α,3β-bis(tert-butyldimethylsilyloxy)-20(S)-{(E)-(4-methyl-4-triethylsilyloxy-2-pentenyloxy)}pregna-5,7,16-triene (83.0 mg, 0.108 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a pale yellow oil (15.9 mg, 34%).

IR(neat): 3400, 2950, 2850, 1460, 1370, 1230, 1150, 1050 cm$^{-1}$. $^1$H NMR δ: 0.89(s, 3H), 0.99(s, 3H), 1.33(s, 6H), 3.71–4.12(m, 5H), 5.42–5.51(m, 1H), 5.63(brs, 1H), 5.66–5.92(m, 3H). UV $\lambda_{max}$ nm: 270, 281, 293.

Example 97
Preparation of 1α,3β-dihydroxy-20(S)-{(Z)-(4-hydroxy-4-methyl-2-pentenyloxy)}pregna-5,7,16-triene By the same procedure as in Example 9, 1α,3β-bis(tert-butyldimethylsilyloxy)-20(S)-{(Z)-(4-methyl-4-triethylsilyloxy-2-pentenyloxy)}pregna-5,7,16-triene (78.0 mg, 0.101 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a colorless oil (32.0 mg, 74%).

IR(neat): 3400, 2960, 2850, 1460, 1375, 1260, 1150, 1050 cm$^{-1}$. $^1$H NMR δ: 0.89(s, 3H), 0.97(s, 3H), 1.34(s, 6H), 3.76(brs, 1H), 3.96–4.24(m, 4H), 5.35–5.51(m, 2H), 5.59–5.78(m, 3H). UV $\lambda_{max}$ nm: 270, 281, 293.

Example 98
Preparation of 1α,3β-dihydroxy-20(S)-(4-ethyl-4-hydroxy-2-hexynyloxy)pregna-5,7,16-triene By the same procedure as in Example 9, 1α,3β-bis(tert-butyldimethylsilyloxy)-20(S)-(4-ethyl-4-triethylsilyloxy-2-hexynyloxy)pregna-5,7,16-triene (79.0 mg, 0.0991 mmol), tetrahydrofuran (3 ml) and 1M tetra-n-butylammonium fluoride solution in tetrahydrofuran (2 ml) were reacted (heating under reflux for 5.5 hours) and worked up, and the residue was purified by preparative thin layer chromatography (0.5 mm×1, dichloromethane:ethyl acetate:ethanol=20:80:1, developed once) to give the title compound as a colorless oil (43.5 mg, 96%).

IR(neat): 3400, 2960, 2930, 2850, 1460, 1370, 1260, 1195, 1150, 1050 cm$^{-1}$. $^1$H NMR δ: 0.90(s, 3H), 0.99(s, 3H), 1.03(t, J=7.8 Hz, 6H), 1.33(d, J=6.6 Hz, 3H), 3.79(brs, 1H), 4.02–4.31(m, 4H), 5.43–5.52(m, 1H), 5.66(brs, 1H), 5.72–5.80(m, 1H). MS m/z: 454(M$^+$), 263(100%). UV $\lambda_{max}$ nm: 270, 281, 293.

Example 99
Preparation of 1α,3β-dihydroxy-20(S)-{(E)-(4-ethyl-4-hydroxy-2-hexenyloxy)}pregna-5,7,16-triene By the same procedure as in Example 9, 1α,3β-bis(tert-butyldimethylsilyloxy)-20(S)-{(E)-(4-ethyl-4-triethylsilyloxy-2-hexenyloxy)}pregna-5,7,16-triene (84.0 mg, 0.105 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a colorless oil (37.3 mg, 78%).

IR(neat): 3400, 2960, 2925, 2850, 1460, 1371, 1255, 1200, 1150, 1055 cm$^{-1}$. $^1$H NMR δ: 0.87(t, J=7.4 Hz, 6H), 0.89(s, 3H), 0.98(s, 3H), 1.32(d, J=6.6 Hz, 3H), 1.55(q, J=7.4 Hz, 4H), 3.78(brs, 1H), 3.86(dd, J=12.6, 5.3 Hz, 1H), 3.94–4.09(m, 3H), 5.41–5.51(m, 1H), 5.58–5.73(m, 4H). UV $\lambda_{max}$ nm: 270, 281, 293.

Example 100
Preparation of 1α,3β-dihydroxy-20(S)-{(Z)-(4-ethyl-4-hydroxy-2-hexenyloxy)}pregna-5,7,16-triene By the same procedure as in Example 9, 1α,3β-bis(tert-butyldimethylsilyloxy)-20(S)-{(Z)-(4-ethyl-4-triethylsilyloxy-2-hexenyloxy)}pregna-5,7,16-triene (81.3 mg, 0.102 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a pale yellow oil (44.0 mg, 94%).

IR(neat): 3400, 2965, 2930, 2850, 1460, 1370, 1275, 1150, 1050 cm$^{-1}$. $^1$H NMR δ: 0.89(s, 3H), 0.90(t, J=7.4 Hz, 6H), 0.98(s, 3H), 1.33(d, J=6.6 Hz, 3H), 1.54(q, J=7.4 Hz, 4H), 3.78(brs, 1H), 3.98–4.24(m, 4H), 5.37–5.49(m, 2H), 5.54–5.68(m, 2H), 5.71–5.78(m, 1H). UV $\lambda_{max}$ nm: 270, 281, 293.

Example 101
Preparation of 1α,3β-dihydroxy-20(R)-(4-hydroxy-4-methyl-2-pentynyloxy)pregna-5,7,16-triene By the same procedure as in Example 9, 1α,3β-bis(tert-butyldimethylsilyloxy)-20(R)-(4-methyl-4-triethylsilyloxy-2-pentynyloxy)pregna-5,7,16-triene (74.1 mg, 0.0963 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a pale yellow oil (21.0 mg, 51%).

IR(neat): 3400, 2970, 2920, 2850, 1450, 1370, 1230, 1160, 1050 cm$^{-1}$. $^1$H NMR δ: 0.85(s, 3H), 0.97(s, 3H), 1.35(d, J=6.4 Hz, 3H), 1.52(s, 6H), 3.78(m, 1H), 5.41–5.50 (m, 1H), 5.64–5.78(m, 2H). UV $\lambda_{max}$ nm: 270, 281, 293.

Example 102
Preparation of 1α,3β-dihydroxy-20(R)-{(E)-(4-hydroxy-4-methyl-2-pentenyloxy)}pregna-5,7,16-triene By the same procedure as in Example 9, 1α,3β-bis(tert-butyldimethylsilyloxy)-20(R)-{(E)-(4-methyl-4-triethylsilyloxy-2-pentenyloxy)}pregna-5,7,16-triene (71.0 mg, 0.0920 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a colorless oil (34.0 mg, 86%).

IR(neat): 3400, 2960, 2925, 2850, 1460, 1370, 1240, 1150, 1055 cm$^{-1}$. $^1$H NMR δ: 0.85(s, 3H), 0.97(s, 3H), 1.32(s, 6H), 3.77(brs, 1H), 3.85–4.16(m, 4H), 5.40–5.50(m, 1H), 5.61–5.91(m, 4H). UV $\lambda_{max}$ nm: 270, 281, 293.

Example 103
Preparation of 1α,3β-dihydroxy-20(R)-{(Z)-(4-hydroxy-4-methyl-2-pentenyloxy)}pregna-5,7,16-triene By the same procedure as in Example 9, 1α,3β-bis(tert-butyldimethylsilyloxy)-20(R)-{(Z)-(4-methyl-4-triethylsilyloxy-2-pentenyloxy)}pregna-5,7,16-triene (67.9 mg, 0.0880 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a white solid (32.0 mg, 85%).

IR(KBr): 3400, 2960, 2920, 2850, 1460, 1370, 1200, 1170, 1135, 1080, 1060, 1035 cm$^{-1}$. $^1$H NMR(CDCl$_3$/CD$_3$OD) δ: 0.86(s, 3H), 0.96(s, 3H), 1.33(s, 6H), 1.37(d, J=6.6 Hz, 3H), 3.74(brs, 1H), 3.90–4.27(m, 4H), 5.36–5.50 (m, 2H), 5.55–5.76(m, 3H). UV $\lambda_{max}$ nm: 270, 281, 293.

Example 104
Preparation of 1α,3β-dihydroxy-20(R)-(4-ethyl-4-hydroxy-2-hexynyloxy)pregna-5,7,16-triene By the same procedure as in Example 9, 1α,3β-bis(tert-butyldimethylsilyloxy)-20(R)-(4-ethyl-4-triethylsilyloxy-2-hexynyloxy)pregna-5,7,16-triene (58.2 mg, 0.0730 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol= 20:80:1, developed once) to give the title compound as a colorless oil (33.5 mg, 100%).

IR(neat): 3400, 2960, 2930, 2850, 1460, 1370, 1325, 1260, 1195, 1150, 1060, 1035 cm$^{-1}$. $^1$H NMR δ: 0.85(s, 3H), 0.98(s, 3H), 1.03(t, J=7.4 Hz, 6H), 1.34(d, J=6.6 Hz, 3H), 3.78(brs, 1H), 4.00–4.32(m, 4H), 5.41–5.50(m, 1H), 5.68 (brs, 1H), 5.71–5.80(m, 1H). UV λ$_{max}$ nm: 270, 281, 293.

Example 105
Preparation of 1α,3β-dihydroxy-20(R)-{(E)-(4-ethyl-4-hydroxy-2-hexenyloxy)}pregna-5,7,16-triene By the same procedure as in Example 9, 1α,3β-bis(tert-butyldimethylsilyloxy)-20(R)-{(E)-(4-ethyl-4-triethylsilyloxy-2-hexenyloxy)}pregna-5,7,16-triene (60.3 mg, 0.0754 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a pale yellow oil (14.5 mg, 42%).

IR(neat): 3400, 2960, 2930, 2850, 1460, 1375, 1330, 1270, 1150, 1060, 1035 cm$^{-1}$. $^1$H NMR δ: 0.86(s, 3H), 0.86(t, J=7.3 Hz, 6H), 0.98(s, 3H), 1.33(d, J=6.6 Hz, 3H), 1.55(q, J=7.6 Hz, 4H), 3.78(brs, 1H), 3.91–4.20(m, 4H), 5.42–5.52(m, 1H), 5.58–5.82(m, 4H). UV λ$_{max}$ nm: 270, 281, 293.

Example 106
Preparation of 1α,3β-dihydroxy-20(R)-{(Z)-(4-ethyl-4-hydroxy-2-hexenyloxy)}pregna-5,7,16-triene By the same procedure as in Example 9, 1α,3β-bis(tert-butyldimethylsilyloxy)-20(R)-{(Z)-(4-ethyl-4-triethylsilyloxy-2-hexenyloxy)}pregna-5,7,16-triene (82.0 mg, 0.103 mmol), tetrahydrofuran (3 ml) and 1M tetra-n-butylammonium fluoride solution in tetrahydrofuran (2 ml) were reacted (heating under reflux for 5.5 hours) and worked up, and then the residue was purified by preparative thin layer chromatography (0.5 mm×1, dichloromethane:ethyl acetate:ethanol=20:80:1, developed once) to give the title compound as a white solid (46.1 mg, 98%).

IR(KBr): 3400, 2960, 2930, 2850, 1460, 1370, 1325, 1270, 1250, 1200, 1150, 1060, cm$^{-1}$. $^1$H NMR δ: 0.86(s, 3H), 0.90(t, J=7.4 Hz, 6H), 0.98(s, 3H), 1.36(d, J=6.4 Hz, 3H), 1.54(q, J=7.4 Hz, 4H), 3.77(brs, 1H), 3.99–4.22(m, 4H), 5.35–5.49(m, 2H), 5.55–5.70(m, 2H), 5.71–5.79(m, 1H). UV λ$_{max}$ nm: 270, 281, 293.

Example 107
Preparation of 1α,3β-dihydroxy-20(S)-(4-hydroxy-4-methyl-2-pentynyloxy)-9,10-secopregna-5,7,10(19),16-tetraene Using 1α,3β-dihydroxy-20(S)-(4-hydroxy-4-methyl-2-pentynyloxy)pregna-5,7,16-triene (13.0 mg, 0.0305 mmol) and ethanol (200 ml), the reaction (irradiation for 2.5 minutes and heating under reflux for 1.5 hours) and work up were performed by the same procedure as in Example 15, and then the residue was purified by preparative thin layer chromatography (0.5 mm×1, hexane:ethyl acetate:ethanol= 8:12:1, developed twice, 0.25 mm×1, dichloromethane:ethyl acetate:ethanol=10:10:1, developed twice, then dichloromethane:ethanol=19:1, developed three times) to give the title compound as a colorless oil (0.758 mg, 5.8%).

IR(neat): 3369, 2929, 2852, 1442, 1369, 1234, 1167, 1060 cm$^{-1}$. $^1$H NMR δ: 0.79(s, 3H), 1.33(d, J=6.6 Hz, 3H), 1.52(s, 6H), 4.03(d, J=15.4 Hz, 1H), 4.14(m, 1H), 4.15(d, J=15.4 Hz, 1H), 4.19–4.30(m,$_1$H), 4.41–4.51(m, 1H), 5.02(brs, 1H), 5.34(brs, 1H), 5.62(brs, 1H), 6.11(d, J=11.2 Hz, 1H), 6.38(d, J=11.2 Hz, 1H). MS m/z: 367(M$^+$—C(CH$_3$)$_2$OH), 129 (100%). UV λ$_{max}$ nm: 264.

Example 108
Preparation of 1α,3β-dihydroxy-20(S)-{(E)-(4-hydroxy-4-methyl-2-pentenyloxy)}-9,10-secopregna-5,7,10(19),16-tetraene Using 1α,3β-dihydroxy-20(S)-{(E)-(4-hydroxy-4-methyl-2-pentenyloxy)}pregna-5,7,16-triene (14.5 mg, 0.0338 mmol) and ethanol (200 ml), the reaction (irradiation for 2.5 minutes and heating under reflux for 2 hours) was performed by the same procedure as in Example 15, and then the residue was purified by preparative thin layer chromatography (0.5 mm×1, dichloromethane:ethyl acetate:ethanol=10:10:1, developed twice, then 0.25 mm×1, dichloromethane:ethanol=18:1, developed three times) to give the title compound as a colorless oil (1.41 mg, 9.7%).

IR(neat): 3400, 2929, 2850, 1446, 1369, 1220, 1153, 1101, 1055 cm$^{-1}$. $^1$H NMR δ: 0.79(s, 3H), 1.33(s, 6H), 3.81(dd, J=6.3, 5.6 Hz, 1H), 3.89–4.04(m, 2H), 4.17–4.30 (m, 1H), 4.38–4.50(m, 1H), 5.02(brs, 1H), 5.34(brs, 1H), 5.59(brs, 1H), 6.11(d, J=11.2 Hz, 1H), 6.27(d, J=11.2 Hz, 1H). MS m/z: 410(M$^+$-H$_2$O), 134(100%). UV λ$_{max}$ nm: 264.

Example 109
Preparation of 1α,3β-dihydroxy-20(S)-{(Z)-(4-hydroxy-4-methyl-2-pentenyloxy)}-9,10-secopregna-5,7,10(19),16-tetraene Using 1α,3β-dihydroxy-20(S)-{(Z)-(4-hydroxy-4-methyl-2-pentenyloxy)}pregna-5,7,16-triene (30.0 mg, 0.0700 mmol) and ethanol (200 ml), the reaction (irradiation for 3.5 minutes and heating under reflux for 2 hours) was performed by the same procedure as in Example 15, and then the residue was purified by preparative thin layer chromatography (0.5 mm×1, hexane:ethyl acetate:ethanol 8:12:1, developed twice, then 0.25 mm×1, dichloromethane:ethanol=16:1, developed three times) to give the title compound as a colorless oil (3.04 mg, 10%).

IR(neat): 3369, 2972, 2929, 2850, 1446, 1371, 1169, 1055 cm$^{-1}$. $^1$H NMR δ: 0.78(s, 3H), 1.34(s, 6H), 2.54–2.68(m, 1H), 2.75–2.88(m, 1H), 3.95–4.30(m, 4H), 4.38–4.50(m, 1H), 5.01(brs, 1H), 5.34(brs, 1H), 5.44(dt, J=12.2, 5.6 Hz, 1H), 5.58–5.70 (m, 2H), 6.11 (d, J=11.2 Hz, 1H), 6.37 (d, J=11.2 Hz, 1H). UV λ$_{max}$ nm: 263.

Example 110
Preparation of 1α,3β-dihydroxy-20(S)-(4-ethyl-4-hydroxy-2-hexynyloxy)-9,10-secopregna-5,7,10(19),16-tetraene Using 1α,3β-dihydroxy-20(S)-(4-ethyl-4-hydroxy-2-hexynyloxy)pregna-5,7,16-triene (40.0 mg, 0.0880 mmol) and ethanol (200 ml), the reaction (irradiation for 2.5 minutes and heating under reflux for 2 hours) was performed by the same procedure as in Example 15, and then the residue was purified by preparative thin layer chromatography (0.5 mm×1, hexane:ethyl acetate:ethanol=8:12:1, developed twice, then 0.25 mm×1, dichloromethane:ethanol= 19:1, developed three times) to give the title compound as a colorless oil (2.76 mg, 6.9%).

IR(neat): 3369, 2970, 2931, 2850, 1442, 1369, 1263, 1182, 1146, 1057 cm$^{-1}$. $^1$H NMR δ: 0.79(s, 3H), 1.03(t, J=7.4 Hz, 6H), 1.32(d, J=6.3 Hz, 3H), 2.55–2.65(m, 1H), 2.77–2.88(m, 1H), 4.06(d, J=15.5 Hz, 1H), 4.14–4.31(m, 3H), 4.38–4.53(m, 1H), 5.02(brs, 1H), 5.34(brs, 1H), 5.61(brs, 1H), 6.11(d, J=11.2 Hz, 1H), 6.38(d, J=11.2 Hz, 1H). UV $\lambda_{max}$ nm: 264.

Example 111

Preparation of 1α,3β-dihydroxy-20(S)-{(E)-(4-ethyl-4-hydroxy-2-hexenyloxy)}-9,10-secopregna-5,7,10(19),16-tetraene Using 1α,3β-dihydroxy-20(S)-{(E)-(4-ethyl-4-hydroxy-2-hexenyloxy)}pregna-5,7,16-triene (35.0 mg, 0.0766 mmol) and ethanol (200 ml), the reaction (irradiation for 3.5 minutes and heating under reflux for 2 hours) was performed by the same procedure as in Example 15, and then the residue was purified by preparative thin layer chromatography (0.5 mm×1, hexane:ethyl acetate:ethanol=8:12:1, developed twice, then 0.25 mm×1, dichloromethane:ethanol=16:1, developed three times) to give the title compound as a colorless oil (3.94 mg, 11%).

IR(neat): 3400, 2968; 2931, 2850, 1446, 1369, 1101, 1055 cm$^{-1}$. $^1$H NMR δ: 0.79(s, 3H), 0.86(t, J=7.4 Hz, 6H), 2.55–2.68(m, 1H), 2.77–2.89(m, 1H), 3.86(dd, J=12.4, 5.4 Hz, 1H), 3.93–4.06(m, 2H), 4.18–4.31(m, 1H), 4.39–4.52 (m, 1H), 5.02(brs, 1H), 5.34(brs, 1H), 5.58(brs, 1H), 6.11(d, J=11.2 Hz, 1H), 6.38(d, J=11.2 Hz, 1H). MS m/z: 456(M$^+$), 134(100%). UV $\lambda_{max}$ nm: 263.

Example 112

Preparation of 1α,3β-dihydroxy-20(S)-{(Z)-(4-ethyl-4-hydroxy-2-hexenyloxy)}-9,10-secopregna-5,7,10(19),16-tetraene Using 1α,3β-dihydroxy-20(S)-{(z)-(4-ethyl-4-hydroxy-2-hexenyloxy)}pregna-5,7,16-triene (41.0 mg, 0.0898 mmol) and ethanol (200 ml), the reaction (irradiation for 3.75 minutes and heating under reflux for 2 hours) was performed by the same procedure as in Example 15, and then the residue was purified by preparative thin layer chromatography (0.5 mm×1, hexane:ethyl acetate:ethanol= 8:12:1, developed twice, then 0.25 mm×1, dichloromethane:ethanol=16:1, developed three times) to give the title compound as a colorless oil (1.58 mg, 3.9%).

IR(neat): 3400, 2968, 2929, 2850, 1448, 1371, 1055 cm$^{-1}$. $^1$H NMR δ: 0.78(s, 3H), 0.90(t, J=7.4 Hz, 3H), 0.91(t, J=7.4 Hz, 3H), 1.34(d, J=6.3 Hz, 3H), 2.55–2.65(m, 1H), 2.78–2.88(m, 1H), 3.95–4.31(m, 4H), 4.39–4.51(m, 1H), 5.01(brs, 1H), 5.34(brs, 1H), 5.42(d, J=12.5 Hz, 1H), 5.55–5.69(m, 2H), 6.11(d, J=11.2 Hz, 1H), 6.38(d, J=11.2 Hz, 1H). UV $\lambda_{max}$ nm: 263.

Example 113

Preparation of 1α,3β-dihydroxy-20(R)-(4-hydroxy-4-methyl- 2-pentynyloxy)-9,10-secopregna-5,7,10(19),16-tetraene Using 1α,3β-dihydroxy-20(R)-(4-hydroxy-4-methyl-2-pentynyloxy)pregna-5,7,16-triene (20.0 mg, 0.0469 mmol) and ethanol (200 ml), the reaction (irradiation for 3 minutes and heating under reflux for 2 hours) was performed by the same procedure as in Example 15, and then the residue was purified by preparative thin layer chromatography (0.5 mm×1, hexane:ethyl acetate:ethanol=8:12:1, developed twice, 0.25 mm×1, dichloromethane:ethyl acetate:ethanol= 10:10:1, developed twice, then dichloromethane:ethanol= 19:1, developed three times) to give the title compound as a colorless oil (1.19 mg, 5.9%).

IR(neat): 3400, 2976, 2929, 2852, 1444, 1373, 1234, 1167, 1063 cm$^{-1}$. $^1$H NMR δ: 0.75(s, 3H), 1.33(d, J=6.3 Hz, 3H), 1.52 (s, 6H), 2.55–2.66(m, 1H), 2.76–2.86(m, 1H), 4.03–4.31(m, 4H), 4.40–4.50(m, 1H), 5.01(brs, 1H), 5.34 (brs, 1H), 5.56(brs, 1H), 6.11(d, J=11.2 Hz, 1H), 6.37(d, J=11.2 Hz, 1H). UV $\lambda_{max}$ nm: 264.

Example 114

Preparation of 1α,3β-dihydroxy-20(R)-{(E)-(4-hydroxy-4-methyl-2-pentenyloxy)}-9,10-secopregna-5,7,10(19),16-tetraene Using 1α,3β-dihydroxy-20(S)-{(E)-(4-hydroxy-4-methyl-2-pentenyloxy)}pregna-5,7,16-triene (31.8 mg, 0.0742 mmol) and ethanol (200 ml), the reaction (irradiation for 3.5 minutes and heating under reflux for 2 hours) was performed by the same procedure as in Example 15, and then the residue was purified by preparative thin layer chromatography (0.5 mm×1, hexane:ethyl acetate:ethanol= 10:10:1, developed twice, then 0.25 mm×1, dichloromethane:ethanol=18:1, developed three times) to give the title compound as a colorless oil (3.03 mg, 9.5%).

IR(neat): 3390, 2972, 2931, 2850, 1448, 1371, 1217, 1153, 1095, 1057 cm$^{-1}$. $^1$H NMR δ: 0.75(s, 3H), 1.33(s, 6H), 2.56–2.68(m, 1H), 2.78–2.88(m, 1H), 3.85–4.08(m, 3H), 4.18–4.30(m, 1H), 4.39–5.00(m, 1H), 5.01(brs, 1H), 5.34 (brs, 1H), 5.62(brs, 1H), 5.73(dt, J=15.8, 5.3 Hz, 1H), 5.85(d, J=15.8 Hz, 1H), 6.11(d, J=11.2 Hz, 1H), 6.38(d, J=11.2 Hz, 1H). UV $\lambda_{max}$ nm: 263.

Example 115

Preparation of 1α,3β-dihydroxy-20(R)-{(Z)-(4-hydroxy-4-methyl-2-pentenyloxy)}-9,10-secopregna-5,7,10(19),16-tetraene Using 1α,3β-dihydroxy-20(R)-{(Z)-(4-hydroxy-4-methyl-2-pentenyloxy)}pregna-5,7,16-triene (30.0 mg, 0.0700 mmol) and ethanol (200 ml), the reaction (irradiation for 3.5 minutes and heating under reflux for 2 hours) was performed by the same procedure as in Example 15, and then the residue was purified by preparative thin layer chromatography (0.5 mm×1, hexane:ethyl acetate:ethanol= 8:12:1, developed twice, then 0.25 mm×1, dichloromethane:ethanol=16:1, developed three times) to give the title compound as a colorless oil (3.04 mg, 10%).

IR(neat): 3350, 2972, 2929, 2850, 1448, 1371, 1167, 1063 cm$^{-1}$. $^1$H NMR δ: 0.75(s, 3H), 1.34(s, 6H), 2.55–2.67(m, 1H), 2.75–2.87(m, 1H), 4.06(q, J=6.3 Hz, 1H), 4.11–4.30(m, 3H), 4.38–4.50(m, 1H), 5.01(brs, 1H), 5.34(brs, 1H), 5.45 (dt, J=12.5, 5.3 Hz, 1H), 5.58(m, 2H), 6.01(d, J=11.2 Hz, 1H), 6.37(d, J=11.2 Hz, 1H). UV $\lambda_{max}$ nm: 263.

Example 116

Preparation of 1α,3β-dihydroxy-20(R)-(4-ethyl-4-hydroxy-2-hexynyloxy)-9,10-secopregna-5,7,10(19),16-tetraene Using 1α,3β-dihydroxy-20(R)-(4-ethyl-4-hydroxy-2-hexynyloxy)pregna-5,7,16-triene (30.8 mg, 0.0677 mmol) and ethanol (200 ml), the reaction (irradiation for 3.5 minutes and heating under reflux for 2 hours) was performed by the same procedure as in Example 15, and then the residue was purified by preparative thin layer chromatography (0.5 mm×1, hexane:ethyl acetate:ethanol=8:12:1, developed twice, then 0.25 mm×1, dichloromethane:ethanol= 19:1, developed three times) to give the title compound as a colorless oil (1.83 mg, 5.9%).

IR(neat): 3390, 2970, 2933, 2852, 1450, 1371, 1265, 1146, 1061 cm$^{-1}$. $^1$H NMR δ: 0.75(s, 3H), 1.03(t, J=7.4 Hz, 6H), 1.33(d, J=6.6 Hz, 3H), 2.56–2.65(m, 1H), 2.75–2.85(m, 1H), 4.08–4.29(m, 4H), 4.39–4.53(m, 1H), 5.01(brs, 1H), 5.34(brs, 1H), 5.64(brs, 1H), 6.10(d, J=11.2 Hz, 1H), 6.38(d, J=11.2 Hz, 1H). UV $\lambda_{max}$ nm: 264.

Example 117

Preparation of 1α,3β-hydroxy-20(R)-{(E)-(4-ethyl-4-hydroxy-2-hexenyloxy)}-9,10-secopregna-5,7,10(19),16-tetraene Using 1α,3β-dihydroxy-20(R)-{(E)-(4-ethyl-4-hydroxy-2-hexenyloxy)}pregna-5,7,16-triene (13.0 mg, 0.0285 mmol) and ethanol (200 ml), the reaction (irradiation for 2.5 minutes and heating under reflux for 2 hours) was performed by the same procedure as in Example 15, and then the residue was purified by preparative thin layer chromatography (0.5 mm×1, hexane:ethyl acetate:ethanol=8:12:1, developed twice, then 0.25 mm×1, dichloromethane:ethanol=16:1, developed three times) to give the title compound as a colorless oil (0.888 mg, 6.8%).

IR(neat): 3378, 2964, 2925, 2852, 1452, 1385, 1057 cm$^{-1}$. $^1$H NMR δ: 0.75(s, 3H), 0.86(t, J=7.4 Hz, 6H), 1.32(d, J=6.6 Hz, 3H), 2.55–2.66(m, 1H), 2.76–2.87(m, 1H), 3.90–4.10 (m, 3H), 4.18–4.31(m, 1H), 4.39–4.51(m, 1H), 5.02(brs, 1H), 5.34(brs, 1H), 5.57–5.81(m, 3H), 6.11(d, J=11.2 Hz, 1H), 6.38(d, J=11.2 Hz, 1H). UV λ$_{max}$ nm: 263.

Example 118

Preparation of 1α,3β-dihydroxy-20(R)-{(Z)-(4-ethyl-4-hydroxy-2-hexenyloxy)}-9,10-secopregna-5,7,10(19),16-tetraene Using 1α,3β-dihydroxy-20(R)-{(Z)-(4-ethyl-4-hydroxy-2-hexenyloxy)}pregna-5,7,16-triene (42.1 mg, 0.0922 mmol) and ethanol (200 ml), the reaction (irradiation for 3.75 minutes and heating under reflux for 2 hours) was performed by the same procedure as in Example 15, and then the residue was purified by preparative thin layer chromatography (0.5 mm×1, hexane:ethyl acetate:ethanol=8:12:1, developed twice, then 0.25 mm×1, dichloromethane:ethanol=16:1, developed three times) to give the title compound as a colorless oil (2.09 mg, 5.0%).

IR(neat): 3400, 2968, 2931, 2852, 1456, 1371, 1059 cm$^{-1}$. $^1$H NMR δ: 0.75(s, 3H), 0.90(t, J=7.4 Hz, 6H), 1.34(d, J=6.6 Hz, 3H), 2.55–2.66(m, 1H), 2.73–2.89(m, 1H), 3.98–4.31 (m, 4H), 4.39–4.51(m, 1H), 5.01(brs, 1H), 5.34(brs, 1H), 5.41(d, J=12.5 Hz, 1H), 5.55–5.71(m, 2H), 6.10(d, J=11.2 Hz, 1H), 6.37(d, J=11.2 Hz, 1H). UV λ$_{max}$ nm: 263.

Example 119

Preparation of 1α,3β-dihydroxy-20(S)-{2(S)-hydroxy-3-methylbutyloxy}pregna-5,7,16-triene To a solution of 1α,3β-bis(tert-butyldimethylsilyloxy)-20 (S)-hydroxypregna-5,7,16-triene (97.9 mg, 0.175 mmol), potassium t-butoxide (230 mg, 2.05 mmol) and dibenzo-18-crown-6 (45.0 mg, 0.125 mmol) in toluene (6 ml) was added (S)-(+)-1,2-epoxy-3-methylbutane (0.18 ml, 1.72 mmol) at room temperature and the mixted solution was stirred at 106° C. for one hour. The reaction solution was diluted with diethyl ether and washed with brine, and then the organic layer was dried over magnesium sulfate. The solvent was distilled off under reduced pressure and the resulting residue was separated by preparative thin layer chromatography (0.5 mm×4, hexane:dichloromethane:ethyl acetate=45:5:2, developed three times) to give a fraction containing 1α,3β-bis(tert-butyldimethylsilyloxy)-20(S)-{2(S)-hydroxy-3-methylbutyloxy}pregna-5,7,16-triene (67.5 mg). An aliquot of 52.6 mg was dissolved in tetrahydrofuran (1.5 ml) and stirred with 1M tetra-n-butylammonium fluoride solution in tetrahydrofuran (0.5 ml) under the condition of an outer temperature of 71° C. for 10 hours. After completion of the reaction, the reaction solution was diluted with ethyl acetate and washed with 1N hydrochloric acid, saturated aqueous sodium bicarbonate solution and brine successively, and the organic layer was dried over magnesium sulfate. The solvent was distilled off under reduced pressure and the resulting residue was purified by preparative thin layer chromatography (0.25 mm×2, dichloromethane:ethanol=15:1, developed twice) to give the title compound as a colorless oil (20.6 mg, 36%).

IR(neat): 3416, 2924, 1462, 1370, 1056, 1196 cm$^{-1}$. $^1$H NMR δ: 0.88(s, 3H), 0.90(d, J=6.9 Hz, 3H), 0.97(s, 3H), 1.31(d, J=6.6 Hz, 3H), 2.72–2.86(m, 1H), 3.10–3.24(m, 1H), 3.39–3.53(m, 2H), 3.77(brs, 1H), 3.96(q, J=6.6 Hz, 1H), 4.00–4.16(m, 1H), 5.40–5.49(m, 1H), 5.60(s, 1H), 5.68–5.80(m, 1H). MS m/z: 312(M$^+$-HOCH$_2$CH(OH) $^i$Pr), 223(100%). UV λ$_{max}$ nm: 269, 281, 292.

Example 120

Preparation of 1α,3β-dihydroxy-20(S)-{2(R)-hydroxy-3-methylbutyloxy}pregna-5,7,16-triene Using 1α,3β-bis(tert-butyldimethylsilyloxy)-20(S)-hydroxypregna-5,7,16-triene (71.5 mg, 0.128 mmol), potassium t-butoxide (170 mg, 1.52 mmol), dibenzo-18-crown-6 (32.0 mg, 0.0888 mmol), toluene (4.5 ml) and (R)-(−)-1,2-epoxy-3-methylbutane (0.13 ml, 1.24 mmol), alkylation reaction (108° C., 1 hour) and work up were performed by the same procedure as in Example 119, and then the residue was separated by preparative thin layer chromatography (0.5 mm×3, hexane:dichloromethane:ethyl acetate=45:5:2, developed three times) to give a fraction containing 1α,3β-bis(tert-butyldimethylsilyloxy)-20(S)-{2(R)-hydroxy-3-methylbutyloxy}pregna-5,7,16-triene (26.8 mg). This was deprotected with tetrahydrofuran (1 ml) and 1M tetra-n-butylammonium fluoride solution in tetrahydrofuran (0.4 ml) (reaction temperature 74° C., reaction period 12 hours) and worked up by the same procedure as in Example 119, and then the residue was purified by preparative thin layer chromatography (0.25 mm×1, dichloromethane:ethanol=15:1, developed twice) to give the title compound as a colorless oil (12.0 mg, 23%).

IR(neat): 3420, 2924, 1460, 1368, 1056 cm$^{-1}$. $^1$H NMR δ: 0.89(s, 3H), 0.89(d, J=6.6 Hz, 3H), 0.98(s, 3H), 1.32(d, J=6.6 Hz, 3H), 2.49–2.62(m, 1H), 2.72–2.87(m, 1H), 3.26–3.54(m, 3H), 3.77(brs, 1H), 3.93–4.18(m, 2H), 5.41–5.50(m, 1H), 5.63(s, 1H), 5.70–5.80(m, 1H). MS m/z: 312(M$^+$-HOCH$_2$CH(OH) $^i$Pr, 100%). UV λ$_{max}$ nm: 269, 280, 292.

Example 121

Preparation of 1α,3β-dihydroxy-20(R)-{2(S)-hydroxy-3-methylbutyloxy}pregna-5,7,16-triene Using 1α,3β-bis(tert-butyldimethylsilyloxy)-20(R)-hydroxypregna-5,7,16-triene (79.0 mg, 0.141 mmol), potassium t-butoxide (190 mg, 1.69 mmol), dibenzo-18-crown-6 (25.0 mg, 0.0694 mmol), toluene (4.5 ml) and (S)-(+)-1,2-epoxy-3-methylbutane (0.15 ml, 1.43 mmol), alkylation reaction (108° C., 1 hour) and work up were performed by the same procedure as in Example 119, and then the residue was separated by preparative thin layer chromatography (0.5 mm×3, hexane:dichloromethane:ethyl acetate=45:5:2, developed three times) to give a fraction containing 1α,3β-bis(tert-butyldimethylsilyloxy)-20(R)-{2(S)-hydroxy-3-methylbutyloxy}pregna-5,7,16-triene (27.8 mg). This was deprotected with tetrahydrofuran (1 ml) and 1M tetra-n-butylammonium fluoride solution in tetrahydrofuran (0.25 ml) (reaction temperature 76° C., reaction period 13 hours) and worked up by the same procedure as in Example 119, and then the residue was purified by preparative thin layer chromatography (0.25 mm×1, dichloromethane:ethanol=15:1, developed twice) to give the title compound as a colorless oil (11.0 mg, 19%).

IR(neat): 3416, 3036, 2928, 1462, 1370, 1270, 1196, 1056 cm$^{-1}$. $^1$H NMR δ: 0.84(s, 3H), 0.90(d, J=6.9 Hz, 3H), 0.97(s, 3H), 1.34(d, J=6.6 Hz, 3H), 2.72–2.88(m, 1H), 3.19–3.34(m, 1H), 3.40–3.60(m, 2H), 3.77(brs, 1H), 3.93–4.16(m, 2H), 5.40–5.50 (m, 1H), 5.67 (s, 1H), 5.71–5.80 (m, 1H). MS m/z: 312 (M$^+$-HOCH$_2$CH(OH) $^i$Pr, 100%). UV λ$_{max}$ nm: 270, 281, 293.

Example 122
Preparation of 1α,3β-dihydroxy-20(R)-{2(R)-hydroxy-3-methylbutyloxy}pregna-5,7,16-triene Using 1α,3β-bis(tert-butyldimethylsilyloxy)-20(R)-hydroxypregna-5,7,16-triene (69.7 mg, 0.125 mmol), potassium t-butoxide (170 mg, 1.52 mmol), dibenzo-18-crown-6 (22.0 mg, 0.0610 mmol), toluene (4 ml) and (R)-(−)-1,2-epoxy-3-methylbutane (0.13 ml, 1.24 mmol), alkylation reaction (109° C., 1 hour) and work up were performed by the same procedure as in Example 119, and then the residue was separated by preparative thin layer chromatography (0.5 mm×3, hexane:dichloromethane:ethyl acetate=45:5:2, developed three times) to give a fraction containing 1α,3β-bis(tert-butyldimethylsilyloxy)-20(R)-{2(R)-hydroxy-3-methylbutyloxy}pregna-5,7,16-triene (23.6 mg). An aliquot of 21.1 mg was deprotected with tetrahydrofuran (1 ml) and 1M tetra-n-butylammonium fluoride solution in tetrahydrofuran (0.2 ml) (reaction temperature 76° C., reaction period 13 hours) and worked up by the same procedure as in Example 119, and then the residue was purified by preparative thin layer chromatography (0.25 mm×1, dichloromethane:ethanol=15:1, developed twice) to give the title compound as a colorless oil (9.4 mg, 20%).

IR(neat): 3404, 2960, 2928, 1462, 1370, 1272, 1196, 1056 cm$^{-1}$. $^1$H NMR δ: 0.85(s, 3H), 0.90(d, J=6.9 Hz, 3H), 0.98(s, 3H), 1.33(d, J=6.3 Hz, 3H), 2.49–2.61(m, 1H), 2.74–2.87(m, 1H), 3.21–3.35(m, 1H), 3.39–3.56(m, 2H), 3.78(brs, 1H), 3.93–4.15(m, 2H), 5.40–5.50(m, 1H), 5.65(s, 1H), 5.70–5.81(m, 1H). MS m/z: 312(M$^+$-HOCH$_2$CH(OH) $^i$Pr, 100%). UV λ$_{max}$ nm: 269, 281, 293.

Example 123
Preparation of 1α,3β-dihydroxy-20(S)-{2(S)-hydroxy-3-methylbutyloxy}-9,10-secopregna-5,7,10(19),16-tetraene Using 1α,3β-dihydroxy-20(S)-{2(S)-hydroxy-3-methylbutyloxy}pregna-5,7,16-triene (9.7 mg, 0.0233 mmol) and ethanol (200 ml), the reaction was performed by the same procedure as in Example 15 (irradiation for 1 minute and 40 seconds, and heating under reflux for 2 hours), and then the residue was purified by preparative thin layer chromatography (0.25 mm×1, dichloromethane:ethanol=20:1, developed twice, then 0.25 mm×0.5, hexane:ethyl acetate:ethanol=10:5:1, developed twice) to give the title compound as a colorless oil (1.06 mg, 11%).

IR(neat): 3400, 2928, 1444, 1368, 1056 cm$^{-1}$. $^1$H NMR δ: 0.78(s, 3H), 0.90(d, J=6.9 Hz, 3H), 0.96(d, J=6.9 Hz, 3H), 1.31(d, J=6.6 Hz, 3H), 2.53–2.68(m, 1H), 2.76–2.90(m, 1H), 3.09–3.24(m, 1H), 3.40–3.55(m, 2H), 3.88–4.01(m, 1H), 4.18–4.30(m, 1H), 4.40–4.50(m, 1H), 5.01(s, 1H), 5.34(s, 1H), 5.57(s, 1H), 6.10(d, J=11.4 Hz, 1H), 6.37(d, J=11.4 Hz, 1H). MS m/z: 312(M$^+$-HOCH$_2$CH(OH) $^i$Pr), 149(100%). UV λ$_{max}$ nm: 262.

Example 124
Preparation of 1α,3β-dihydroxy-20(S)-{2(R)-hydroxy-3-methylbutyloxy}-9,10-secopregna-5,7,10(12),16-tetraene Using 1α,3β-dihydroxy-20(S)-{2(R)-hydroxy-3-methylbutyloxy}pregna-5,7,16-triene (12.0 mg, 0.0288 mmol) and ethanol (200 ml), the reaction was performed by the same procedure as in Example 15 (irradiation for 1 minute and 40 seconds, and heating under reflux for 2 hours), and then the residue was purified by preparative thin layer chromatography (0.25 mm×1, hexane:ethyl acetate:ethanol 10:5:1, developed once, then 0.25 mm×0.5, dichloromethane:ethanol=30:1, developed twice, then dichloromethane:ethanol=10:1, developed twice) to give the title compound as a colorless oil (1.45 mg, 12%).

IR(neat): 3400, 2928, 1444, 1370, 1056 cm$^{-1}$. $^1$H NMR δ: 0.78(s, 3H), 0.89(d, J=6.9 Hz, 3H), 0.97(d, J=6.9 Hz, 3H), 1.31(d, J=6.6 Hz, 3H), 2.54–2.67(m, 1H), 2.74–2.90(m, 1H), 3.25–3.53(m, 3H), 3.95(q, J=6.6 Hz, 1H), 4.19–4.32(m, 1H), 4.38–4.51(m, 1H), 5.01(s, 1H), 5.34(s, 1H), 5.58(s, 1H), 6.11(d, J=11.4 Hz, 1H), 6.37(d, J=11.4 Hz, 1H). MS m/z: 312(M$^+$-HOCH$_2$CH(OH) $^i$Pr), 149 (100%). UV λ$_{max}$ nm: 263.

Example 125
Preparation of 1α,3β-dihydroxy-20(R)-{2(S)-hydroxy-3-methylbutyloxy}-9,16-secopregna-5,7,10(19),16-tetraene Using 1α,3β-dihydroxy-20(R)-{2(S)-hydroxy-3-methylbutyloxy}pregna-5,7,16-triene (9.9 mg, 0.0238 mmol) and ethanol (200 ml), the reaction was performed by the same procedure as in Example 15 (irradiation for 1 minute and 40 seconds, and heating under reflux for 2 hours), and then the residue was purified by preparative thin layer chromatography (0.25 mm×1, hexane ethyl acetate:ethanol=10:5:1, developed twice, then 0.25 mm×0.5, dichloromethane:ethanol=15:1, developed twice) to give the title compound as a colorless oil (0.786 mg, 7.9%).

IR(neat): 3392, 2928, 1452, 1370, 1264, 1056 cm$^{-1}$. $^1$H NMR δ: 0.74(s, 3H), 0.90(d, J=6.6 Hz, 3H), 0.97(d, J=6.6 Hz, 3H), 1.33(d, J=6.3 Hz, 3H), 2.55–2.68(m, 1H), 2.77–2.90(m, 1H), 3.21–3.34(m, 1H), 3.41–3.56(m, 2H), 3.98(q, J=6.3 Hz, 1H), 4.18–4.31(m, 1H), 4.38–4.51(m, 1H), 5.01(s, 1H), 5.34(s, 1H), 5.63(s, 1H), 6.10(d, J=11.4 Hz, 1H), 6.37(d, J=11.4 Hz, 1H). MS m/z: 312(M$^+$-HOCH$_2$CH(OH) $^i$Pr), 149(100%). UV λ$_{max}$ nm: 262.

Example 126
Preparation of 1α,3β-dihydroxy-20(R)-{2(R)-hydroxy-3-methylbutyloxy}-9,10-secopregna-5,7,10(19),16-tetraene Using 1α,3β-dihydroxy-20(R)-{2(R)-hydroxy-3-methylbutyloxy}pregna-5,7,16-triene (8.5 mg, 0.0204 mmol) and ethanol (200 ml), the reaction was performed by the same procedure as in Example 15 (irradiation for 1 minute and 40 seconds, and heating under reflux for 2 hours), and then the residue was purified by preparative thin layer chromatography (0.25 mm×1, dichloromethane:ethanol=15:1, developed twice, then 0.25 mm×0.5, hexane:ethyl acetate:ethanol=10:5:1, developed twice) to give the title compound as a colorless oil (0.400 mg, 4.7%).

IR(neat): 3416, 2924, 1452, 1370, 1262, 1066 cm$^{-1}$. $^1$H NMR δ: 0.75 (s, 3H), 0.91(d, J=6.6 Hz, 3H), 0.97(d, J=6.6 Hz, 3H), 1.32(d, J=6.3 Hz, 3H), 2.55–2.67(m, 1H), 2.77–2.88(m, 1H), 3.21–3.33(m, 1H), 3.36–3.57(m, 2H), 3.92–4.06(m, 1H), 4.19–4.30(m, 1H), 4.40–4.50(m, 1H), 5.01(s, 1H), 5.34(s, 1H), 5.60(s, 1H), 6.10(d, J=11.4 Hz, 1H), 6.37(d, J=11.4 Hz, 1H). UV λ$_{max}$ nm: 260.

The following test examples report activities of Compound 1 (1α,3β-dihydroxy-20(S)-(3-hydroxy-3-methylbutylthio)-9,10-secopregna-5,7,10(19),16-tetraene), Compound 2 (1α,3β-dihydroxy-20(R)-(3-hydroxy-3-methylbutylthio)-9,10-secopregna-5,7,10(19),16-tetraene), Compound 3 (1α,3β-dihydroxy-20(R)-(4-hydroxy-4-methyl-2-pentynylthio)-9,10-secopregna-5,7,10(19),16-tetraene), Compound 4 (1α,3β-dihydroxy-20(R)-(4-ethyl-4-hydroxy-2-hexynylthio)- 9,10-secopregna-5,7,10(19),16-tetraene), Compound 5 (1α,3β-dihydroxy-20(R)-{(E)-4-hydroxy-4-methyl-2-pentenylthio}-9,10-secopregna-5,7,10(19),16-tetraene) and Compound 6 (1α,3β-dihydroxy-20(R)-((E)-4-ethyl-4-hydroxy-2-hexenylthio)-9,10-secopregna-5,7,10(19),16-tetraene).

Test example 1

Figure 2:
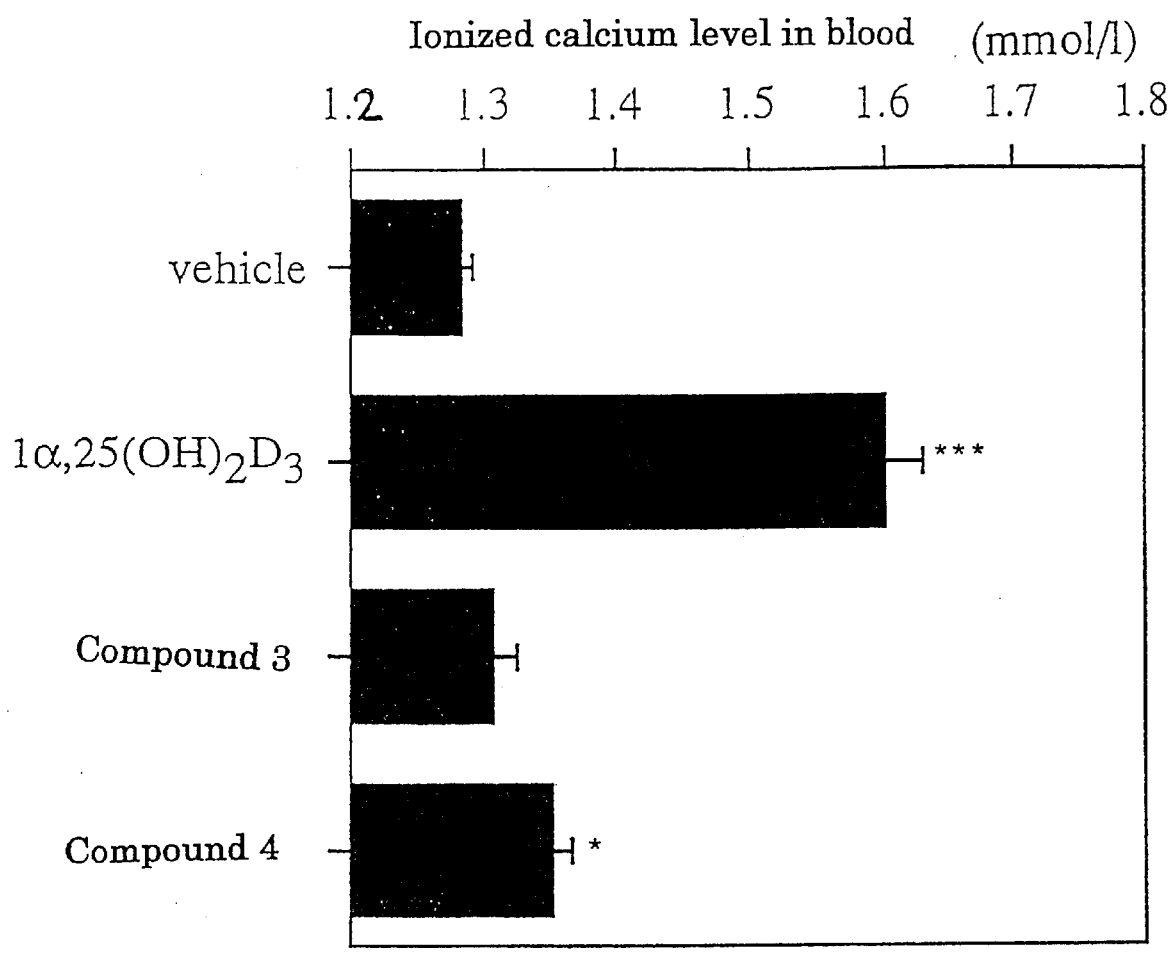
FIG. 2 is a graph showing assay results of the ionized calcium level in blood after administration of an activated vitamin $D_3$ or vitamin $D_3$ derivatives.
Figure 3:
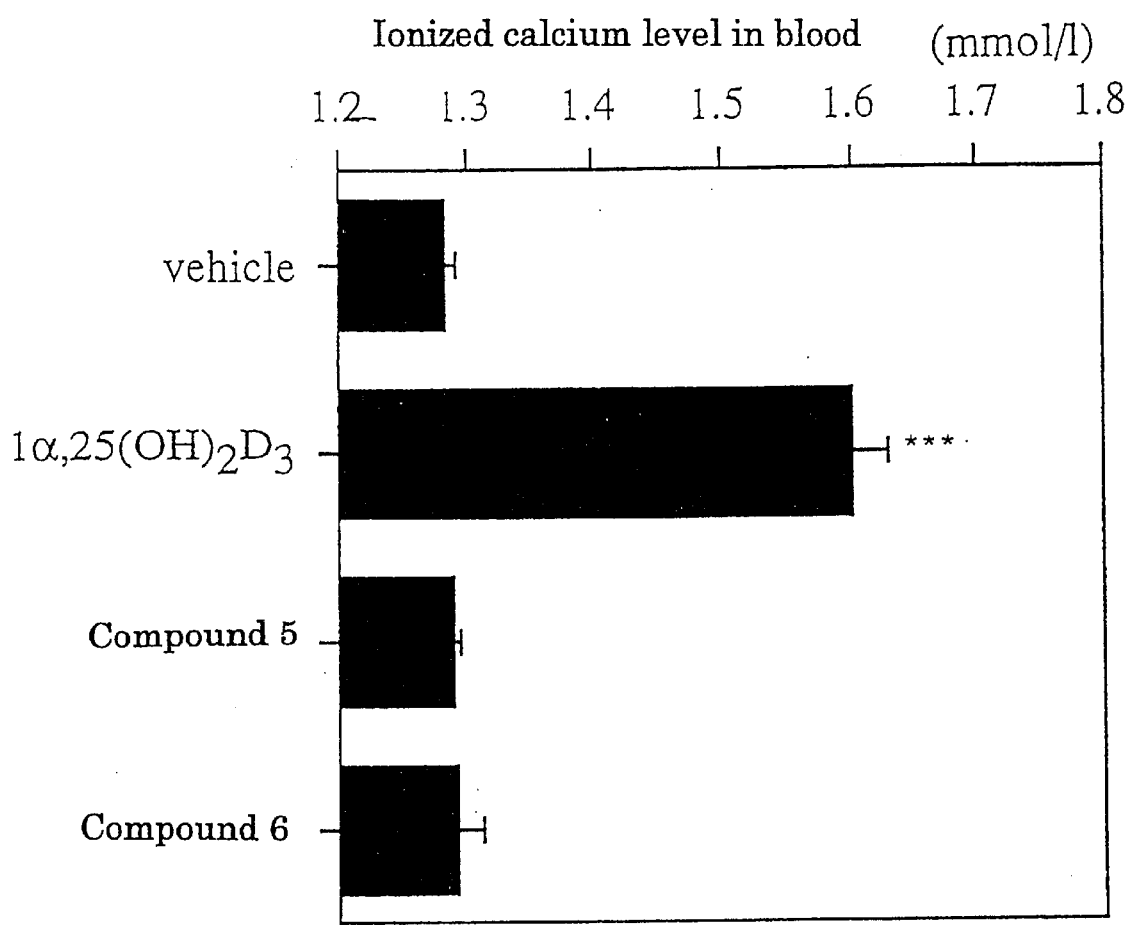
FIG. 3 is a graph showing assay results of the ionized calcium level in blood after administration of an activated vitamin $D_3$ or vitamin $D_3$ derivatives.

At hour 24 after an activated vitamin D$_3$ or each vitamin D$_3$ derivative dissolved in phosphate buffer was intravenously administered to 8-week old male ddY mice at a dose of 30 μg/kg, the ionized calcium level in blood was determined. Experiments were run on 5 examples for each group and the results were expressed as average±standard deviation. The calcemic activity of the activated vitamin $D_3$ and each vitamin $D_3$ derivative was evaluated in comparison with that of a control group to which had been administered the same amount of phosphate buffer alone. The results are shown in FIGS. 1 to 3. The significance of differences was determined using Dunnett's T test, and the symbols *,  and * in the figures mean significant differences at the probability levels of 5%, 1% and 0.1%. respectively.

Test Example 2

Figure 4:
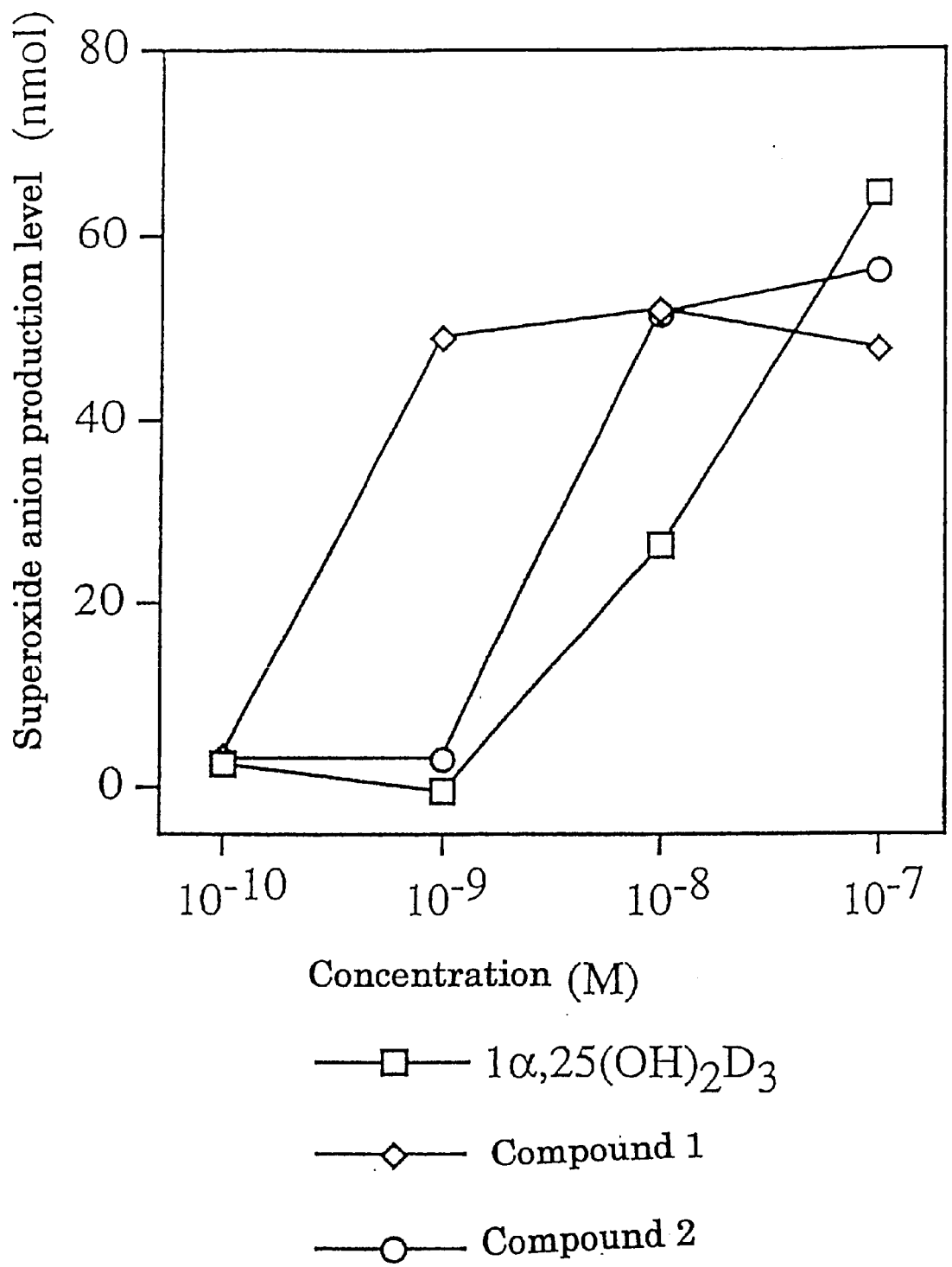
FIG. 4 is a graph showing evaluation test results of the differentiation-inducing activity of an activated vitamin $D_3$ or vitamin $D_3$ derivatives.
Figure 5:
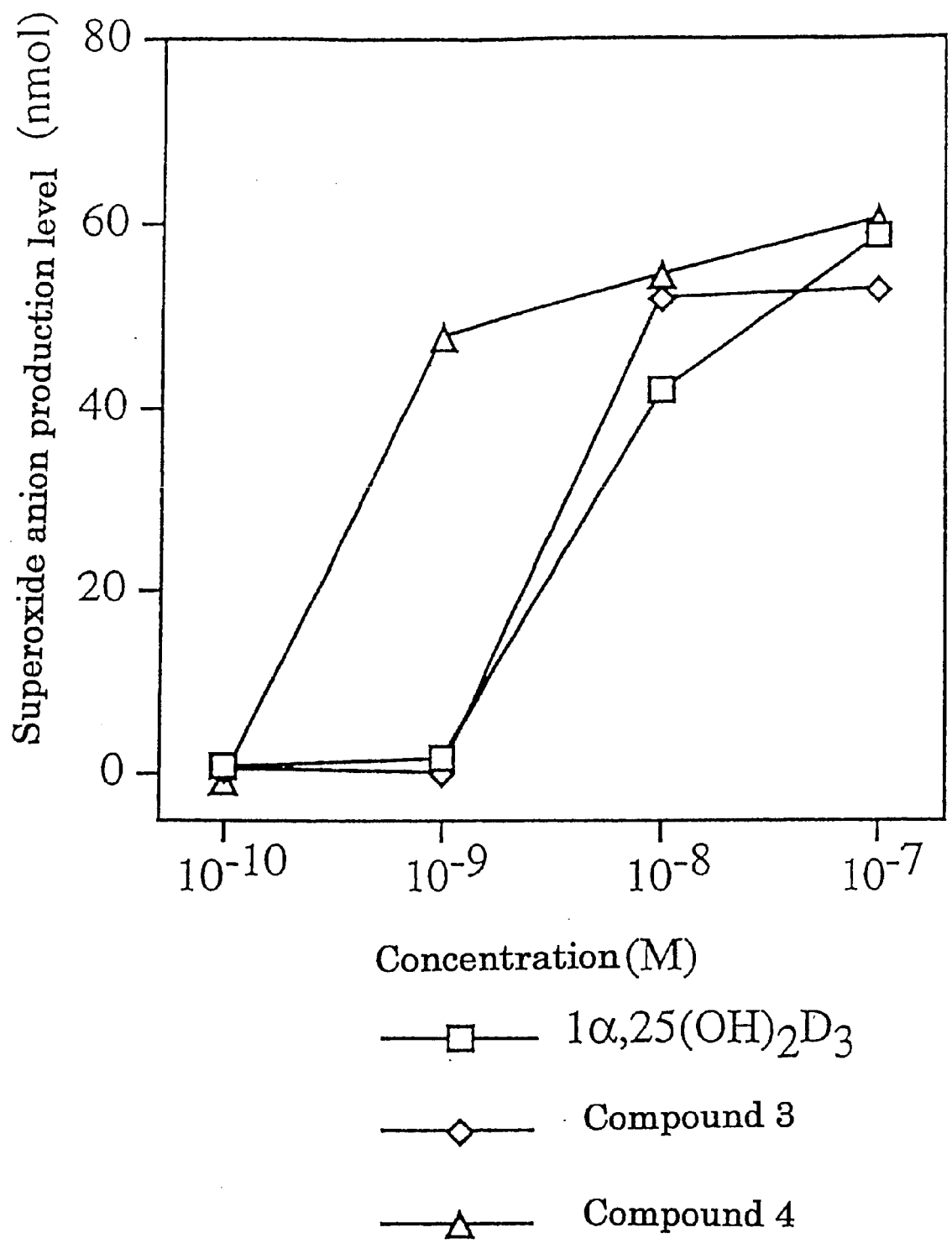
FIG. 5 is a graph showing evaluation test results of the differentiation-inducing activity of an activated vitamin $D_3$ or vitamin $D_3$ derivatives.
Figure 6:
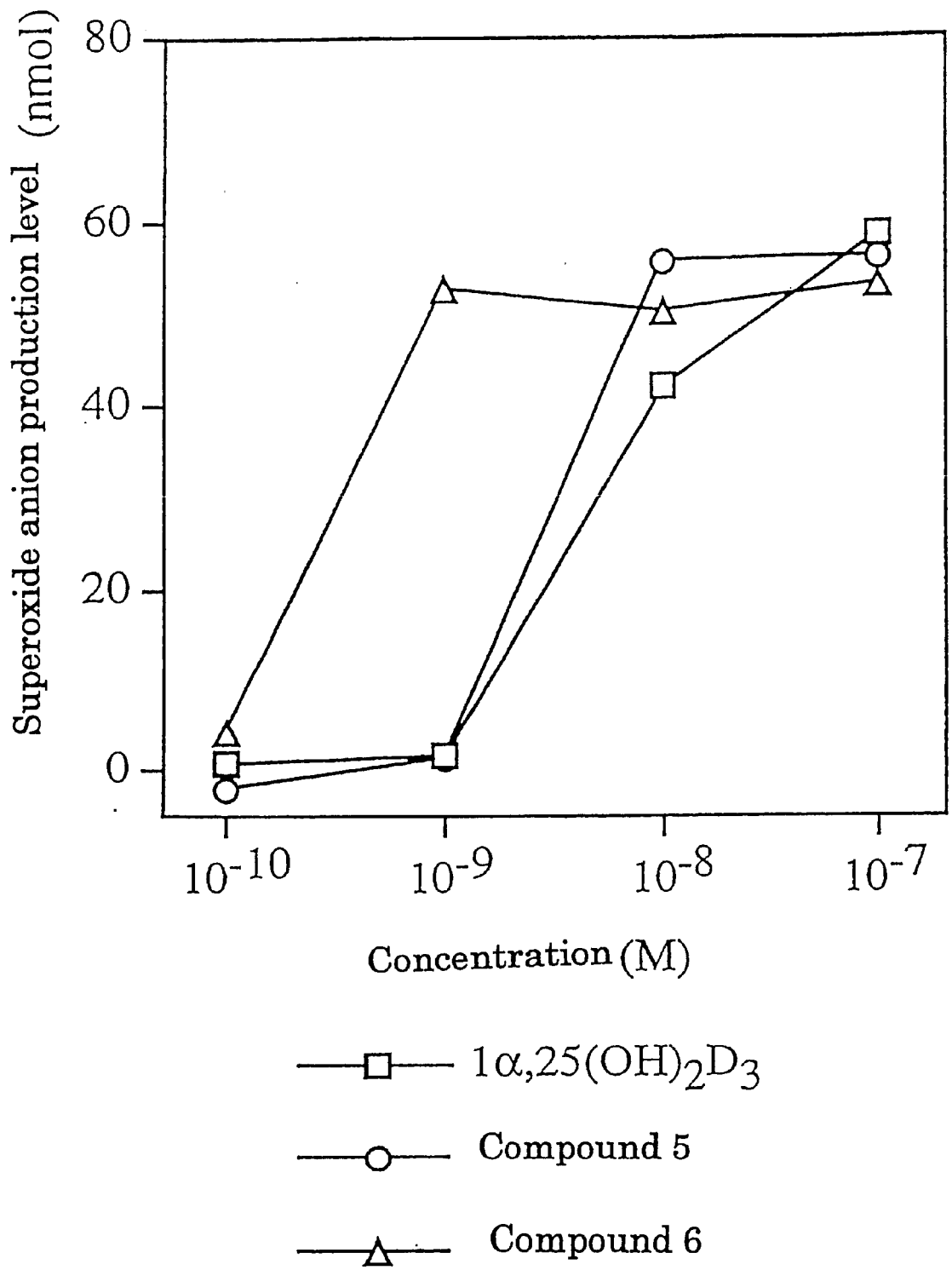
FIG. 6 is a graph showing evaluation test results of the differentiation-inducing activity of an activated vitamin $D_3$ or vitamin $D_3$ derivatives.

HL-60 cells were subcultured in RPMI-1640 medium containing 10% fetal bovine serum and 20 μg/ml gentamicin under 5% $CO_2$ at 37° C. Differentiation-inducing activity was evaluated as follows. At first, a 24-well plate was inoculated with $10^5$ cells on the medium containing each test compound at various concentrations and incubated for 4 days under the above incubation conditions. Then, the amount of superoxide produced by stimulation of phorbol myristate acetate (PMA) was determined as cytochrome C-reducing ability. Namely, culture supernatants were removed by suction and then the cells treated with each test compound were suspended in 1.5 ml of the reaction mixture (80 μM ferricytochrome C, 500 ng/ml PMA) and incubated at 37° C. for one hour. Then, the absorbance of the culture supernatants was determined at OD 550–540 using a Hitachi dual-wavelength spectrophotometer. The results are shown in FIGS. 4 to 6. The concentration of reduced cytochrome C was calculated by using a molar absorption coefficient of $19.1 \times 10^3$ $cm^{-1}$.

INDUSTRIAL APPLICABILITY

Compounds of general formula (1) of the present invention are useful as pharmaceutical agents such as antitumor agents or antirheumatic agents with weak hypercalcemic activity.

What is claimed is:

1. A compound of general formula (4):

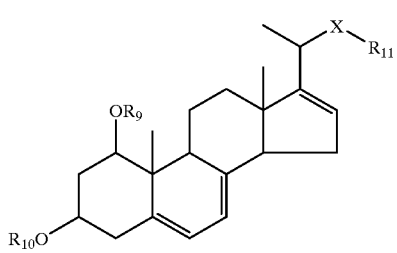

(4)

wherein
X represents an oxygen or sulfur atom,
$R_{11}$ represents
(i) a saturated C1–C15 aliphatic hydrocarbon group or unsaturated C2–C15 aliphatic hydrocarbon group which may be substituted by a hydroxyl group or a protected hydroxyl group, (ii) a —$COR_{12}$ group where $R_{12}$ represents an alkyl, aryl or alkoxy group, or

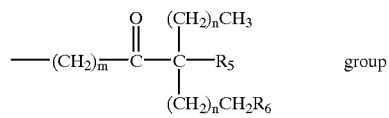

(iii)

group wherein $R_5$ and $R_6$ each represent a hydrogen atom or a hydroxyl group, m represents an integer of 1 to 4, and n represents an integer of 0 to 2, $R_2$ represents —$OR_9$ or a hydrogen atom, and $R_9$ and $R_{10}$ may by the same or different and each represents a hydrogen atom or a protecting group.

2. The compound of claim 1, wherein $R_{11}$ is a saturated C1–C15 aliphatic hydrocarbon group which may be substituted by a hydroxyl group.

3. The compound of claim 1, wherein $R_{11}$ is an unsaturated C2–C15 aliphatic hydrocarbon group which may be substituted by a hydroxyl group.

4. The compound of claim 1, wherein $R_{11}$ is a group (2):

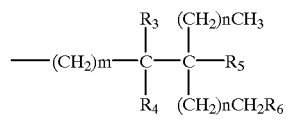

(2)

wherein $R_3$ and $R_4$ may be the same or different and each represent a hydrogen atom or a hydroxyl group, or are combined to represent=O, provided that $R_3$ and $R_4$ cannot be a hydroxyl group simultaneously, $R_5$ and $R_6$ each represent a hydrogen atom or a hydroxyl group, but $R_6$ cannot be a hydroxyl group simultaneously with $R_3$ or $R_4$, m represents an integer of 1 to 4, and n represents an integer of 0 to 2; or a group (3):

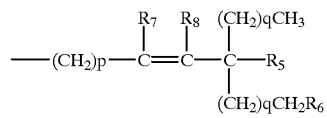

(3)

wherein $R_5$ and $R_6$ may be the same or different and each represent a hydrogen atom or a hydroxyl group, $R_7$ and $R_8$ each represent a hydrogen atom or are combined to represent a covalent bond, p represents an integer of 1 to 3, and q represents an integer of 0 to 2.

5. The compound of claim 1, wherein $R_{11}$ is a 3-hydroxy-3-methylbutyl group.

* * * * *